(12) United States Patent
Liang et al.

(10) Patent No.: US 10,907,219 B2
(45) Date of Patent: Feb. 2, 2021

(54) COMPOSITIONS AND METHODS FOR CONTROLLING CELLULAR FUNCTION

(71) Applicants: STC.UNM, Albuquerque, NM (US); Fu-Sen Liang, Albuquerque, NM (US); Wei Wang, Albuquerque, NM (US)

(72) Inventors: Fu-Sen Liang, Albuquerque, NM (US); Wei Wang, Albuquerque, NM (US)

(73) Assignee: UNM Rainforest Innovations, Albuquerque, NM (US)

( * ) Notice: Subject to any disclaimer, the term of this patent is extended or adjusted under 35 U.S.C. 154(b) by 0 days.

(21) Appl. No.: 15/119,506

(22) PCT Filed: Feb. 18, 2015

(86) PCT No.: PCT/US2015/016280
§ 371 (c)(1),
(2) Date: Aug. 17, 2016

(87) PCT Pub. No.: WO2015/126884
PCT Pub. Date: Aug. 27, 2015

(65) Prior Publication Data
US 2017/0226595 A1    Aug. 10, 2017

Related U.S. Application Data

(60) Provisional application No. 61/941,091, filed on Feb. 18, 2014, provisional application No. 62/091,181, filed on Dec. 12, 2014.

(51) Int. Cl.
*C12Q 1/68* (2018.01)
*C12Q 1/6897* (2018.01)

(52) U.S. Cl.
CPC ........ *C12Q 1/6897* (2013.01); *C12N 2510/00* (2013.01)

(58) Field of Classification Search
CPC .................................................. C12Q 1/6897
See application file for complete search history.

(56) References Cited

U.S. PATENT DOCUMENTS

| 2014/0364588 | A1* | 12/2014 | Haugwitz | ............... | C12P 21/02 |
| | | | | | 530/350 |
| 2015/0291966 | A1* | 10/2015 | Zhang | .................... | C12N 15/63 |
| | | | | | 435/320.1 |
| 2017/0226595 | A1 | 8/2017 | Liang et al. | | |

FOREIGN PATENT DOCUMENTS

| WO | WO 2013/188406 A1 | 12/2013 |
| WO | WO 2015/126884 A1 | 8/2015 |

OTHER PUBLICATIONS

Liang et al in "Engineering the ABA plant stress pathway for regulation of induced proximity" (Science Signaling, 2011, vol. 4, Issue 164, pp. 1-9).*
Boatright et al in "Activation of caspases-8 and -10 by FLIPL" (Biochem, J, 2004, vol. 382, pp. 651-657).*
Fegan et al in "Chemically Controlled Protein Assembly: Techniques and Applications" (Chem. Rev. 2010, vol. 110, pp. 3315-3336).*
Liang et al in "Engineering the ABA plant stress pathway for regulation of induced proximity" (Science Signaling, 2011, vol. 4, Issue 164, pp. 1-9). (Year: 2011).*
Umeda et al in "A Photocleavable Rapamycin Conjugate for Spatiotemporal Control of Small GTPase Activity" (JACS Communications, published online Dec. 13, 2010). (Year: 2010).*
Ando et al, "Development and Applications of Fluorogenic Probes for Mercury (II) Based on Vinyl Ether Oxymercuration," 2011 *J. Am. Chem. Soc.*, vol. 133: pp. 2556-2566.
Aubel et al, "Mammalian synthetic biology—from tools to therapies," 2010 *BioEssays* vol. 32: pp. 332-345.
Au-Yeung et al, "A selective reaction-based fluorescent probe for detecting cobalt in living cells," 2012 *Chem. Commun.*, vol. 48: pp. 5268-5270.
Bashor et al, "Rewiring Cells: Synthetic biology as a tool to interrogate the organizational principles of living systems," 2010 *Ann. Rev Biophys*, vol. 39: pp. 515-537.
Boissier et al, "The guanine nucleotide exchange factor Tiam1: A Janus-faced molecule in cellular signaling," 2013 *Cell. Signal.*, vol. 26: pp. 483-491.
Chan et al, "Reaction-based small-molecule fluorescent probes for chemoselective bioimaging," 2012 *Nat. Chem.*, vol. 4: pp. 973-984.
Czlapinski et al, "Conditional Glycosylation in Eukaryotic Cells Using a Biocompatible Chemical Inducer of Dimerization," 2008 *J. Am. Chem. Soc.*, vol. 130: pp. 13186-13187.
Derose et al, "Manipulating signaling at will: chemically-inducible dimerization (CID) techniques resolve problems in cell biology," 2013 *Pflugers Arch*, vol. 465: pp. 409-417.
Garner et al, "Specific fluorogenic probes for ozone in biological and atmospheric samples," 2009 *Nat. Chem.*, vol. 1: pp. 316-321.
Gestwicki et al, "Chemical Control Over Protein-Protein Interactions: Beyond Inhibitors," 2007 *Combi. Chem. High Throughput Screen*, vol. 10: pp. 667-675.
Gill et al, "Cyclosporine Treatment Reduces Oxygen Free Radical Generation and Oxidative Stress in the Brain of Hypoxia-reoxygenated Newborn Piglets," 2012 *PLoS One*, vol. 7(7): pp. e40471.
Godowski et al, "Signal Transduction and Transcriptional Regulation by Glucocorticoid Receptor-LexA Fusion Proteins" 1988 *Science*, vol. 241: pp. 812-816.

(Continued)

*Primary Examiner* — Catherine S Hibbert
(74) *Attorney, Agent, or Firm* — Mueting Raasch Group

(57) ABSTRACT

This disclosure describes compositions and methods that involve a first modular component and a second modular component. The first modular component includes a first target molecule coupled to a first dimerizing moiety. The second modular component includes a second target molecule coupled to a second dimerizing moiety. The first dimerizing moiety dimerizes with the second dimerizing moiety when the first dimerizing moiety binds a chemical induced proximity (CIP) inducer.

14 Claims, 40 Drawing Sheets

Specification includes a Sequence Listing.

(56) References Cited

OTHER PUBLICATIONS

Gossen et al, "Tight control of gene expression in mammalian cells by tetracycline-responsive promoters," 1992 *Proc. Natl. Acad. Sci. USA*, vol. 89: pp. 5547-5551.

Govan et al, "Hydrogen Peroxide Induced Activation of Gene Expression in Mammalian Cells using Boronate Estrone Derivatives," 2012 *Angew. Chem. Int. Ed.*, vol. 51: pp. 9066-9070.

Haynes et al, "Eukaryotic systems broaden the scope of synthetic biology," 2009 *J. Cell Biol.* vol. 187: pp. 589-596.

Hyslop et al, "Measurement of striatal H2O2 by microdialysis following global forebrain ischemia and reperfusion in the rat: correlation with the cytotoxic potential of H2O2 in vitro," 1995 *Brain Res.*, vol. 671: pp. 181-186.

International Preliminary Report on Patentability PCT/US2015/016280, dated Sep. 1, 2016.

International Search Report and Written Opinion PCT/US2015/016280, dated May 29, 2015.

Lee et al, "Autophagy, mitochondria and oxidative stress: cross-talk and redox signaling," 2012 *Biochem. J.*, vol. 441: pp. 523-540.

Liang et al, "Small Molecule-Induced Proximity," 2013, Chembiomolecular Science: At the Frontier of Chemistry and Biology, Springer Japan.

Liang et al, "Smart" Gene Therapy for Parkinson's Disease, Michael J Fox Foundation for Parkinson's Research 2013.

Liang, March of Dimes Foundation Research and Grants Administration.

Lippert et al, "Boronate Oxidation as a Bioorthogonal Reaction Approach for Studying the Chemistry of Hydrogen Peroxide in Living Systems," 2011 *Acc. Chem. Res.*, vol. 44(9): pp. 793-804.

Lippert et al, "Reaction Based Fluorescent Probes for Selective Imaging of Hydrogen Sulfide in Living Cells," 2011 *J. Am. Chem. Soc.*, vol. 133: pp. 10078-10080.

Liu et al, "Capture and Visualization of Hdrogen Sulfide by a Fluorescent Probe," 2011 *Angew. Chem. Int. Ed.*, vol. 50: pp. 10327-10239.

Lopez-Lazaro, "Dual role of hydrogen peroxide in cancer: Possible relevance to cancer chemoprevention and therapy," 2007 *Cancer Lett.*, vol. 252: pp. 1-8.

Lynch et al, "Direct interactions of ABA-insensitive(ABI)-clade protein phosphatase(PP)2Cs with calcium-dependent protein kinases and ABA response element-binding bZIPs may contribute to turning off ABA response," 2012 *Plant Mol Biol.*, vol. 80: pp. 647-658.

Miyamoto et al, "Rapid and orthogonal logic gating with a gibberellin-induced dimerization system" 2012 *Nat. Chem. Biol.*, vol. 8: pp. 465-470.

Miyamoto et al, "Synthesizing Biomolecule-Based Boolean Logic Gates," 2012 *ACS Synth. Biol.*, vol. 2: pp. 72-82.

Miyazono et a., "Structural basis of abscisic acid signalling," 2009 *Nature*, vol. 462: pp. 609-614.

Non-Final Office Action U.S. Appl. No. 15/119,506, dated Oct. 5, 2017.

Pederzolli et al, "N-acetylaspartic acid impairs enzymatic antioxidant defenses and enhances hydrogen peroxide concentration in rat brain," 2010 *Metab. Brain Dis.*, vol. 25: pp. 251-259.

Peng et al, "A Fluorescent Probe for Fast and Quantitative Detection of Hydrogen Sulfide in Blood," 2011 *Agnew. Chem. Int. Ed.*, vol. 50: pp. 9672-9675.

Purnick et al, "The second wave of synthetic biology: from modules to systems," 2009 *Nature*, vol. 10: pp. 410-422.

Rice, "H2O2: A Dynamic Neuromodulator," 2011 *Neuroscientist*, vol. 17(4): pp. 389-406.

Ridley et al, "Cell Migration: Integrating Signals from Front to Back," 2003 *Science*, vol. 302: pp. 1704-1709.

Ruder et al, "Synthetic Biology Moving into the Clinic," 2011 *Science* vol. 333: pp. 1248-1252.

Setsukinai et al, "Development of Novel Fluorescence Probes that can Reliably Detect Reactive Oxygen Species and Distinguish Specific Species," 2003 *J. Biol. Chem.*, vol. 278: pp. 3170-3175.

Shimada et al, "Structural basis for gibberellin recognition by its receptor GID1," 2008 *Nature*, vol. 456: pp. 520-523.

Skwarczynska et al, "Activation of NF-KB signalling by fusicoccin-induced dimerization," 2012 *PNAS*, pp. E377-E386.

Song et al, "Oxidation-Resistant Fluorogenic Probe for Mercury Based on Alkyne Oxymercuration," 2008 *J. Am. Chem. Soc.*, vol. 130: pp. 16460-16461.

Spanos et al, "Quantitation of Hydrogen Peroxide Fluctuations and Their Modulation of Dopamine Dynamics in the Rat Dorsal Striatum Using Fast-scan Cyclic Voltammetry," 2013 *ACS Chem. Neurosci.*, vol. 4: pp. 782-789.

Stone et al, "Hydrogen Peroxide: A Signaling Messenger," 2006 *Antioxid. Redox. Signal.*, vol. 8: pp. 243-270.

Taki et al, "Development of Highly Sensitive Fluorescent Probes for Detection of Intracellular Copper(1) in Living Systems," 2010 *J. Am. Chem. Soc.*, vol. 132: pp. 5938-5939.

Tigges et al, "Recent advances in mammalian synthetic biology—design of synthetic transgene control networks," 2009 *Curr. Opin. Biotechnol*, vol. 20: pp. 449-460.

Wang et al, "Patchy Particle Self-Assembly via Metal Coordination," 2013. *J. Am. Chem. Soc.* vol. 135: pp. 14064-14067.

Wright et al, "Light Control of Cellular Processes Using Photocaged Abscisic Acid," *Wiley-VCH*, full paper.

Xuan et al, "Fluorescent Probes for the Detection of Hydrogen Sulfide in Biological Systems," 2012 *Angew. Chem. Int. Ed.*, vol. 51: pp. 2282-2284.

Zeng et al, "Constructing de Novo H2O2 Signaling via Induced Protein Proximity," 2015, *ACS Chem. Biol.* vol. 10: pp. 1404-1410.

Zeng et al, "Engineering Iron Responses in Mammalian Cells by Signaled-Induced Protein Proximity," 2017, ACS Synth Biol, vol. 6: pp. 921-927.

Denny, "Prodrug Strategies in Cancer Therapy" Jun. 2001 *European Journal of Medicinal Chemistry*, 36 (2001): 577-595.

Murase et al., "Gibberellin-Induced DELLA Recognition by the Gibberellin Receptor GID1" Nov. 2008 *Nature*, 456 (2008): 459-464.

Miyazono et al, "Structural Basis of Abscisic Acid Signalling" Dec. 2009 *Nature*, 462 (2009): 609-615.

Chan et al, "Reaction-Based Small-Molecule Fluorescent Probes for Chemoselective Bioimaging" Nov. 2012 *Nature Chemistry*, 4 (2012): 973-984.

\* cited by examiner

COMPOSITIONS AND METHODS FOR CONTROLLING CELLULAR FUNCTION

CROSS-REFERENCE TO RELATED APPLICATION

This application is the § 371 U.S. National Stage of International Application No. PCT/US2015/016280, filed 18 Feb. 2015, which claims priority to U.S. Provisional Patent Application Ser. No. 61/941,091, filed Feb. 18, 2014, and U.S. Provisional Patent Application Ser. No. 62/091,181, filed Dec. 12, 2014, each of which is incorporated herein by reference.

SUMMARY

This disclosure describes, in one aspect, a composition that includes a first modular component and a second modular component. The first modular component includes a first target molecule coupled to a first dimerizing moiety. The second modular component includes a second target molecule coupled to a second dimerizing moiety. The first dimerizing moiety dimerizes with the second dimerizing moiety when the first dimerizing moiety binds a chemical induced proximity (CIP) inducer.

In some embodiments, the composition further includes an activatable inactive chemical-induced proximity inducer. In some of these embodiments, the composition can further include a compound that converts the activatable inactive chemical-induced proximity inducer to an active chemical-induced proximity inducer. In some of these embodiments, the first dimerizing moiety is bound to the active chemical-induced proximity inducer and dimerized with the second dimerizing moiety. In some of these embodiments, the compound that converts the activatable inactive chemical-induced proximity inducer to an active chemical-induced proximity inducer comprises $H_2O_2$.

In some embodiments, the chemical-induced proximity inducer can include ABA or GA.

In another aspect, this disclosure describes a cell that includes any of the compositions summarized above and a polynucleotide whose expression is modulated by a complex that includes the first modular component dimerized to the second modular component. In some embodiments, the polynucleotide can include a polynucleotide endogenous to the cell. In some embodiments, the polynucleotide can include a polynucleotide exogenous to the cell.

In another aspect, this disclosure describes a complex that includes a first modular component and a second modular component. The first modular component generally includes a first target molecule coupled to a first dimerizing moiety and an active chemical-induced proximity inducer bound to the first dimerizing moiety. The second modular component generally includes a second dimerizing moiety dimerized to the first dimerizing moiety of the first modular component and a second target molecule coupled to the second dimerizing moiety.

In yet another aspect, this disclosure describes a method that generally involves introducing any composition summarized above into a cell, introducing a activatable inactive chemical-induced proximity inducer into the cell, and contacting the cell with a compound that activates the activatable inactive chemical-induced proximity inducer. In some of these embodiments, the cell further includes a polynucleotide whose expression is modulated by a complex of the first modular component dimerized to the second modular component. In some of these embodiments, the polynucleotide can include a polynucleotide endogenous to the cell. In other embodiments, the polynucleotide can include a polynucleotide exogenous to the cell.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Figure 1:
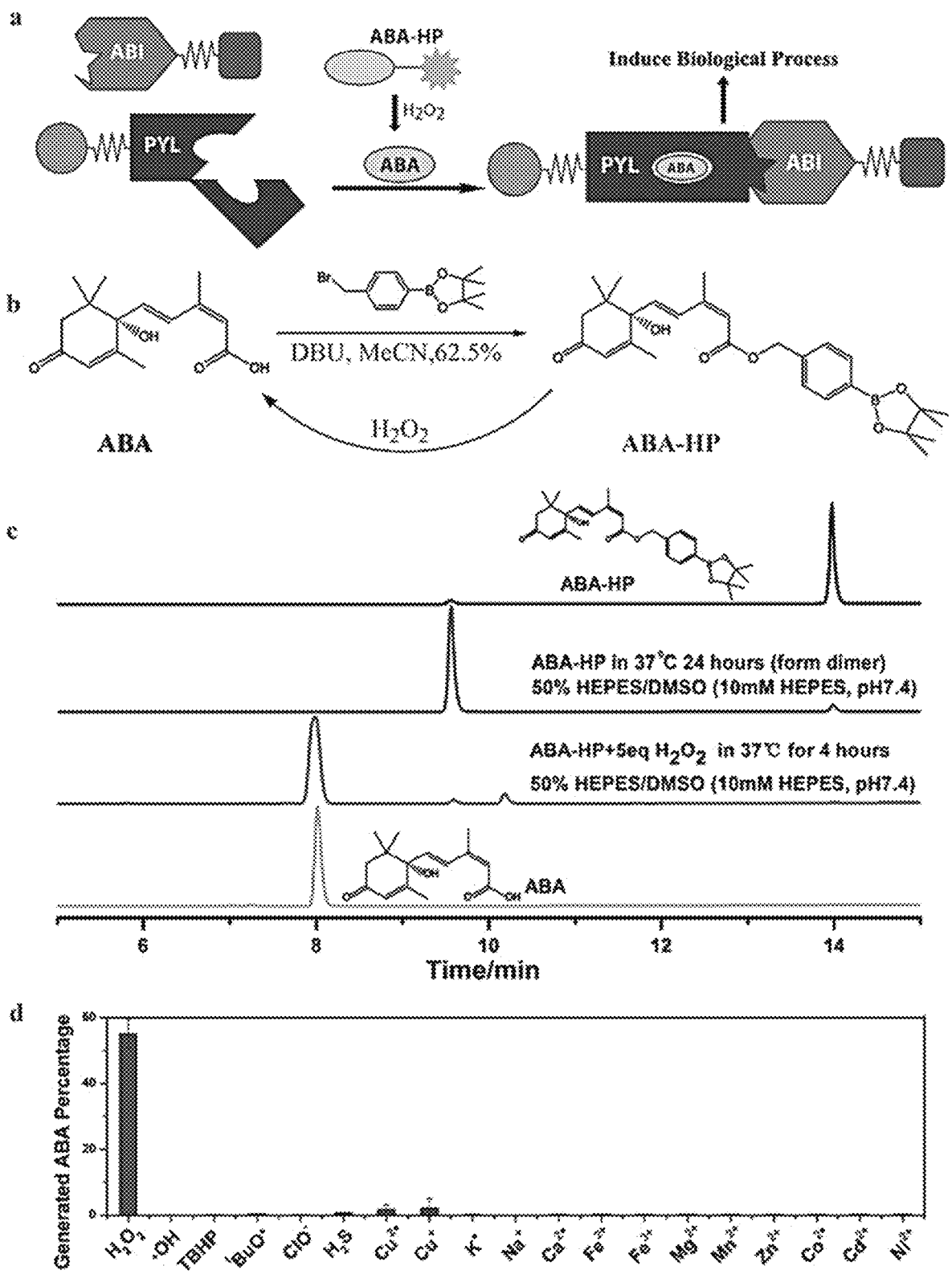
FIG. 1. (a) General strategy for $H_2O_2$-inducible protein proximity to control biological processes. (b) Synthesis of ABA-HP and its conversion to ABA in the presence of $H_2O_2$. (c) 1 mM ABA-HP was treated with or without 5 mM $H_2O_2$ in 50% HEPES/DMSO for different time at 37° C., and detected by HPLC. (d) 100 μM ABA-HP was treated with 100 μM reductive H2S, reactive oxygen species (ROS) including $H_2O_2$, .OH, tert-butyl hydroperoxide (TBHP), tBuO. (.OH and .OtBu were generated by reaction of $Fe^{2+}$ with $H_2O_2$ or TBHP, respectively), and ClO⁻, as well as 100 μM of common cellular metal ions for four hours at 37° C. The results are the averages of three independent experiments.

H₂S was generated by Na₂S in HEPES buffer (pH 7.4). .OH and .OtBu were generated by reaction of $Fe^{2+}$ with $H_2O_2$ or tert-butyl hydroperoxide (TBHP), respectively. Shown HPLC chromatograms are representative from three independent experiments. The results were quantified by integrating the peak area corresponding to the ABA peak over the total areas of all peaks to give the generated ABA % as shown in FIG. 1d.

Figure 6:
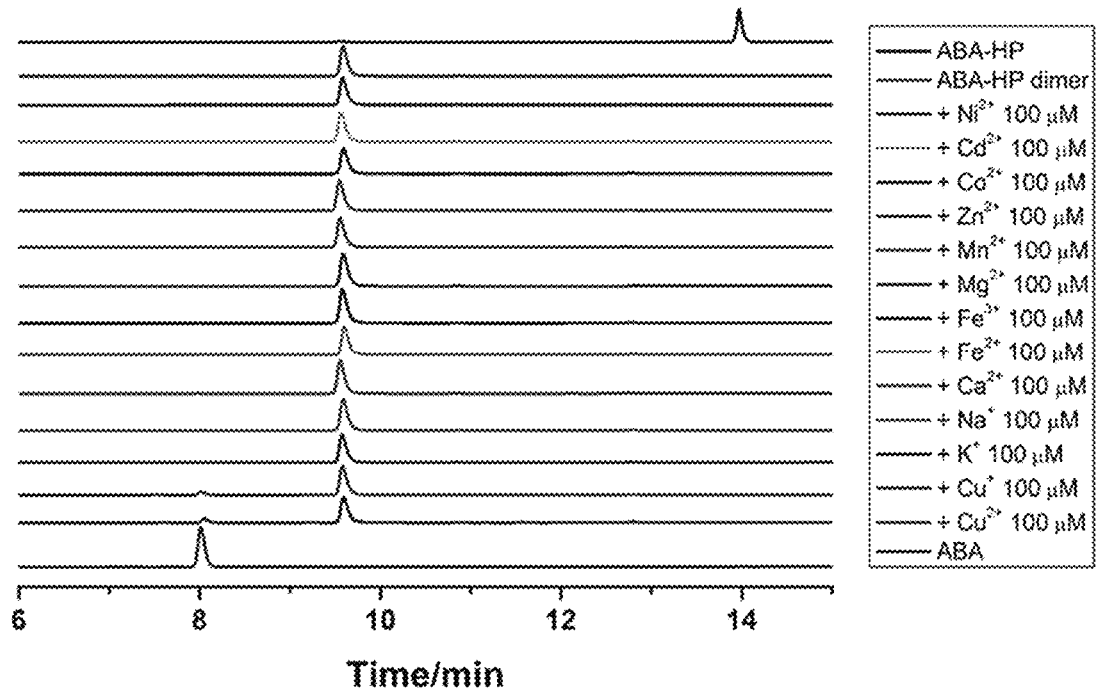

FIG. 6. Reaction selectivity of ABA-HP (100 μM) against common cellular metal ions (100 μM) in 50% HEPES/DMSO. The results were analyzed by HPLC after four-hour incubation in 37° C. Shown HPLC chromatograms are representative from three independent experiments. The results were quantified by integrating the peak area corresponding to the ABA peak over the total areas of all peaks to give the generated ABA % as shown in FIG. 1d.

Figure 7:
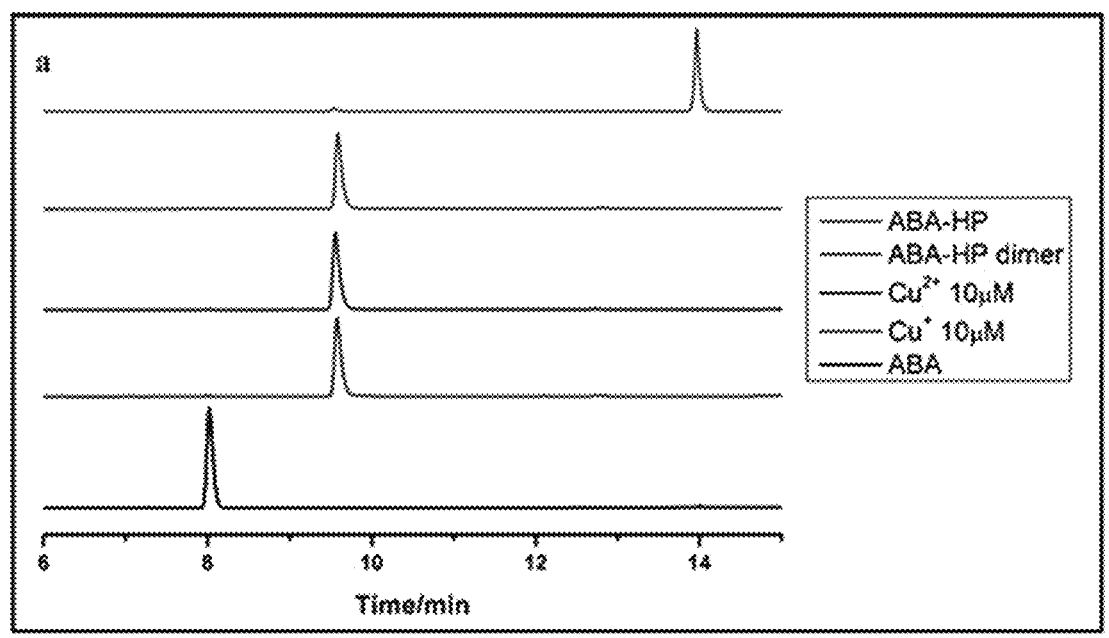
Figure 7:
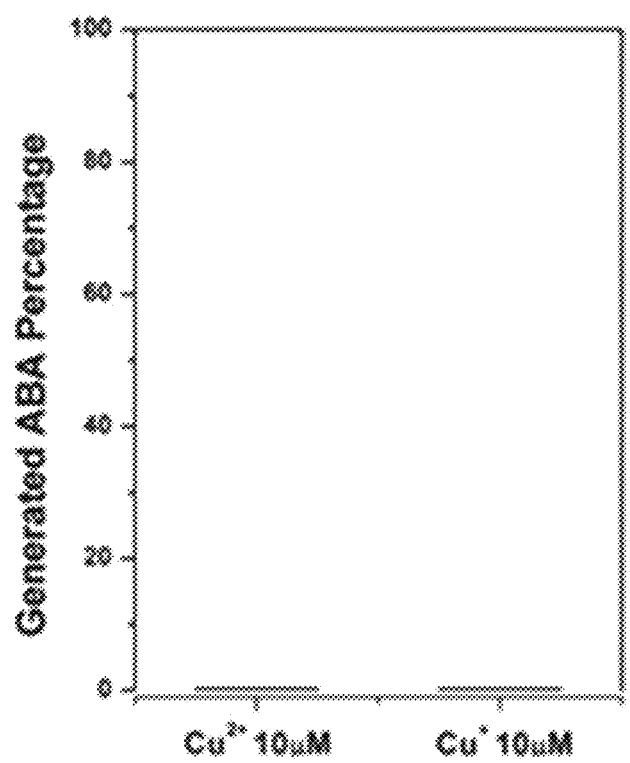

FIG. 7. Reaction selectivity of ABA-HP (100 μM) against $Cu^+$ and $Cu^{2+}$ (10 μM) in 50% HEPES/DMSO. The results were analyzed by HPLC after four-hour incubation in 37° C. (a) Shown HPLC chromatograms are representative from three independent experiments. (b) The results were quantified by integrating the peak area corresponding to the ABA peak over the total areas of all peaks to give the generated ABA % as shown.

Figure 8:
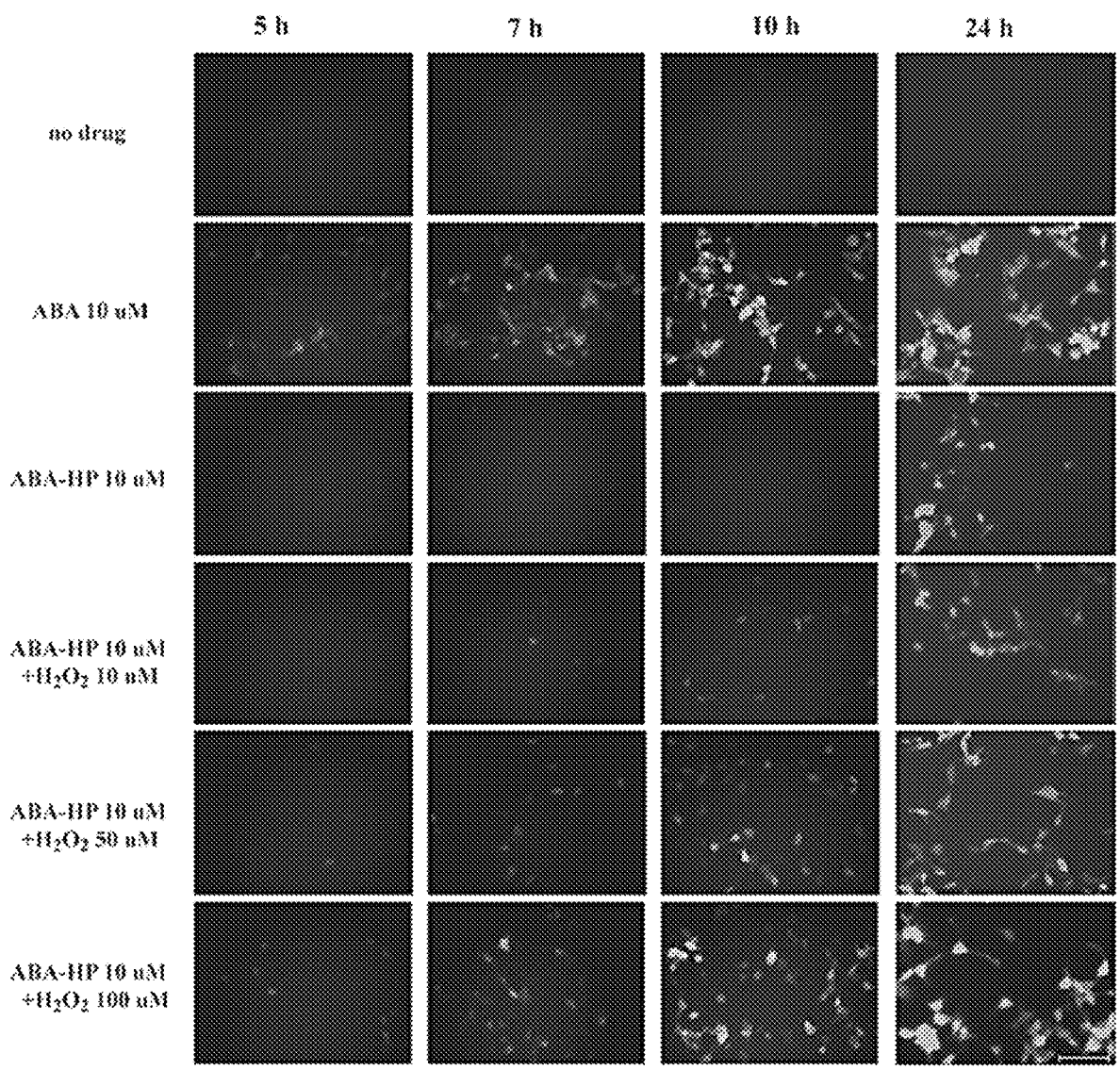

FIG. 8. Dose-dependent and time-dependent GFP expression controlled by $H_2O_2$ in HEK 293T eGFP reporter cells. Cells were treated with indicated molecules and eGFP expression was observed under fluorescence microscope after indicated times. The scale bar is 100 μm. Images shown are representative from three independent experiments.

Figure 9:
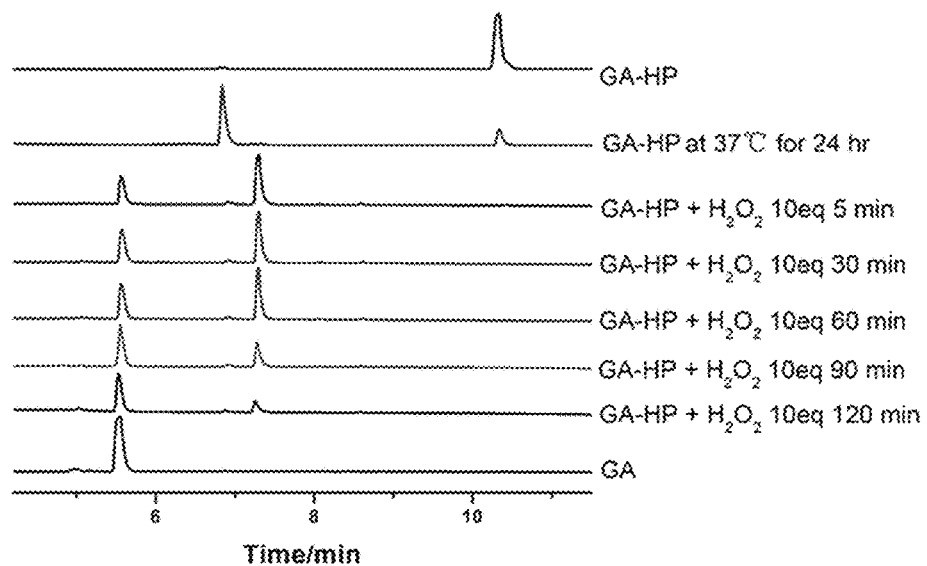

FIG. 9. Time dependent cleavage of GA-HP by $H_2O_2$ detected by HPLC. 5 mM GA-$H_2O_2$ was treated with 50 mM $H_2O_2$ in 50% HEPES/DMSO (10 mM HEPES, pH 7.4) from 0 to 120 minutes at 37° C. Shown HPLC chromatograms are representative from three independent experiments.

Figure 10:
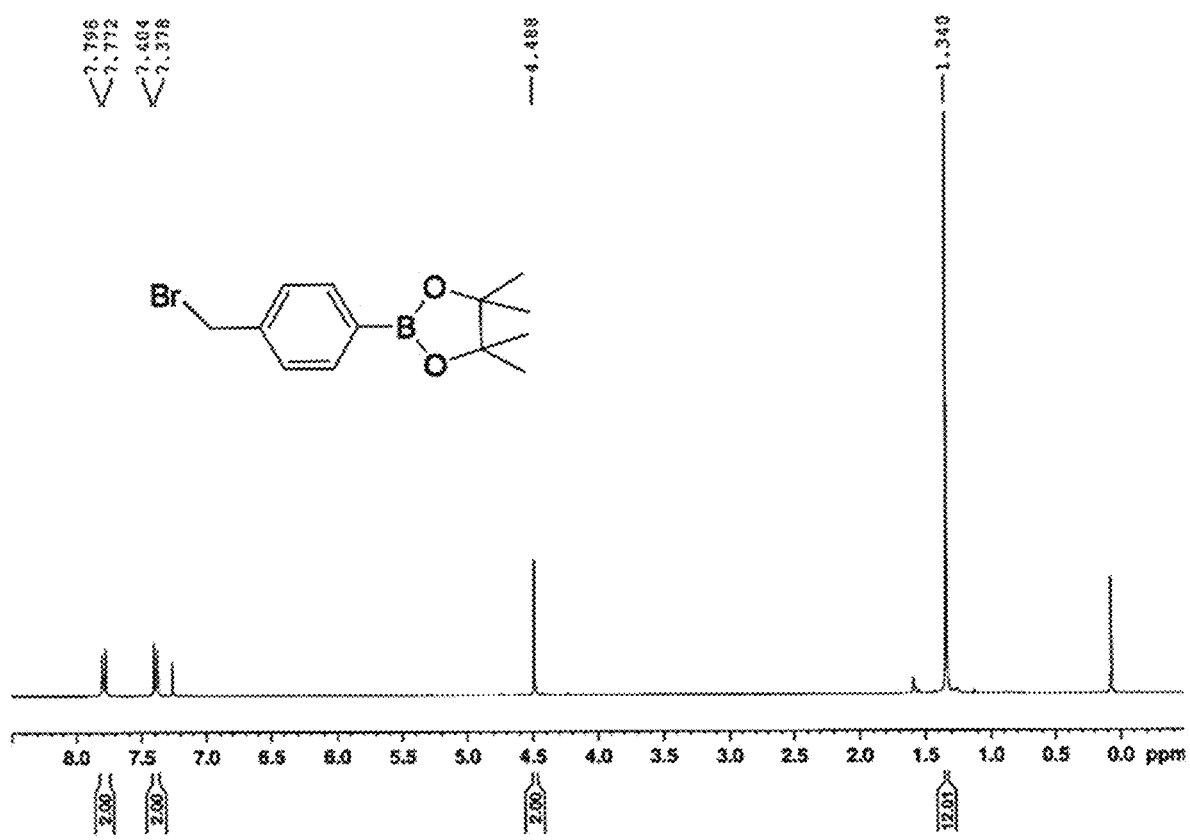
Figure 11:
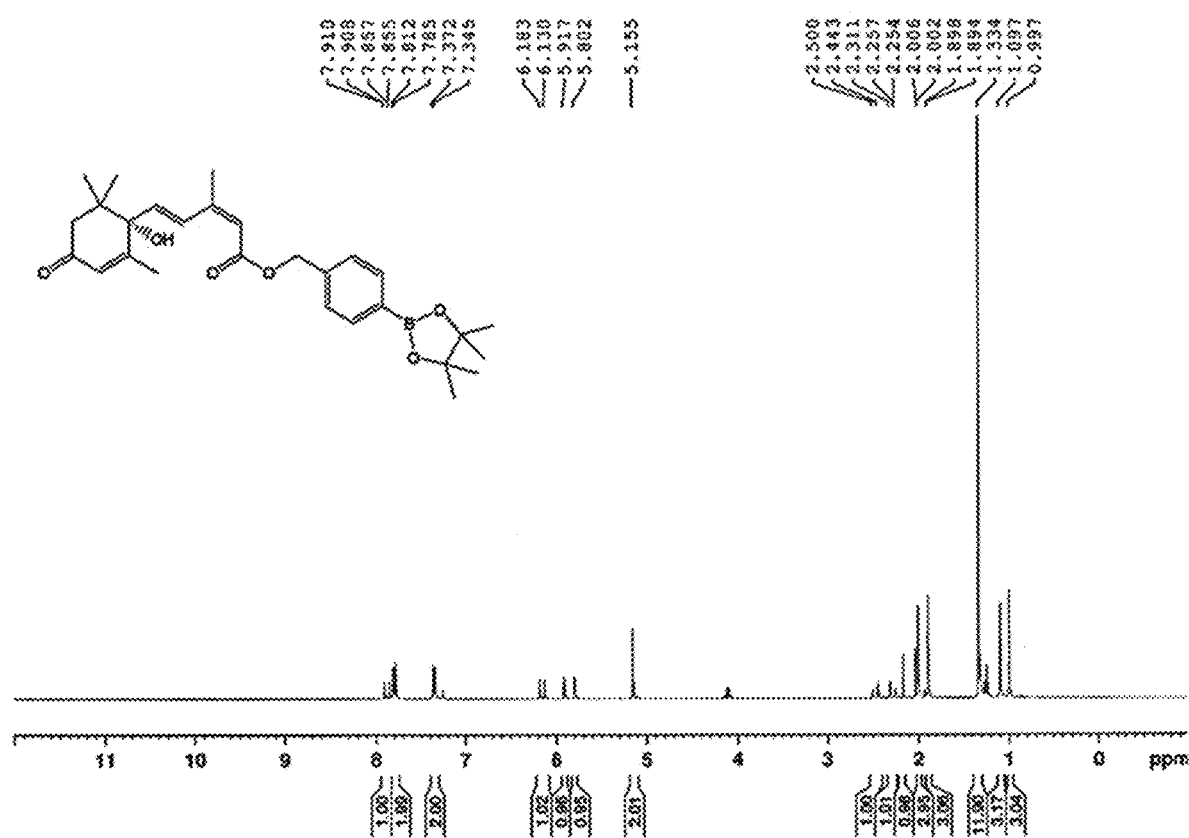
Figure 12:
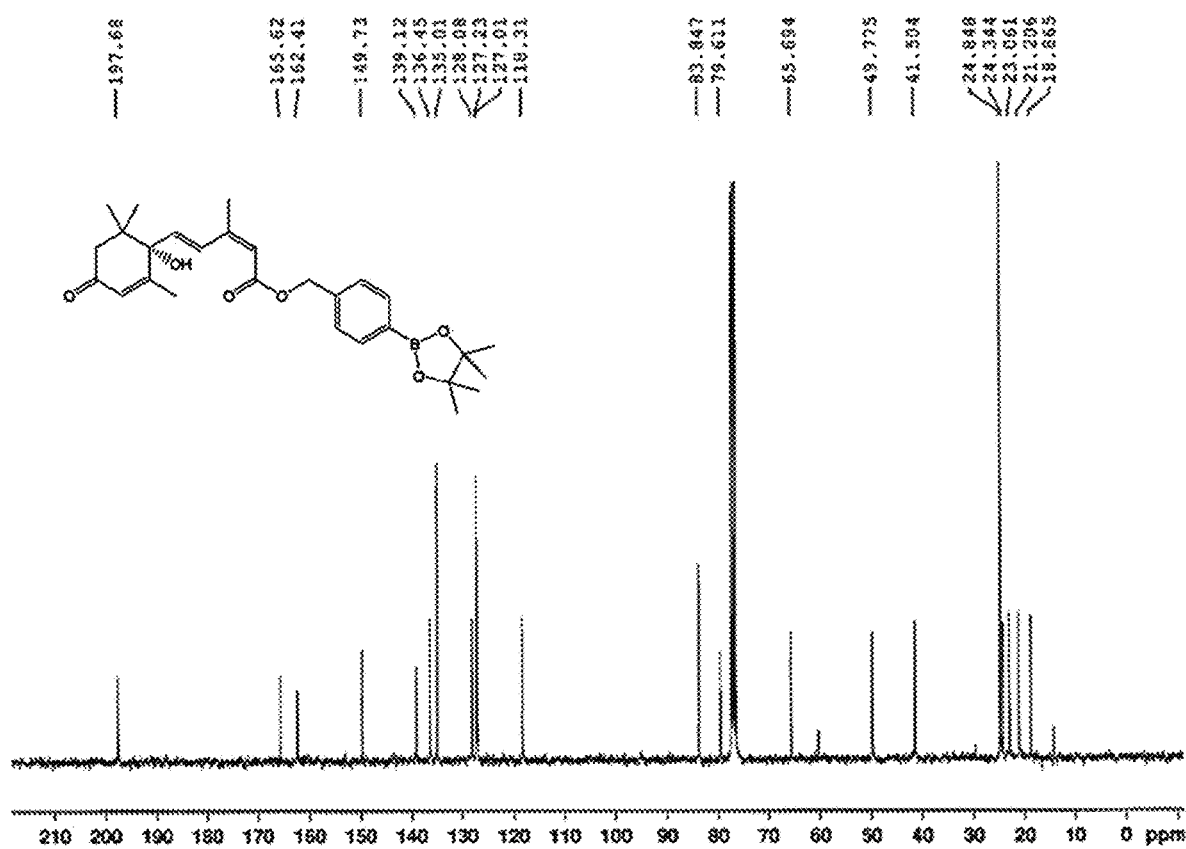
Figure 13:
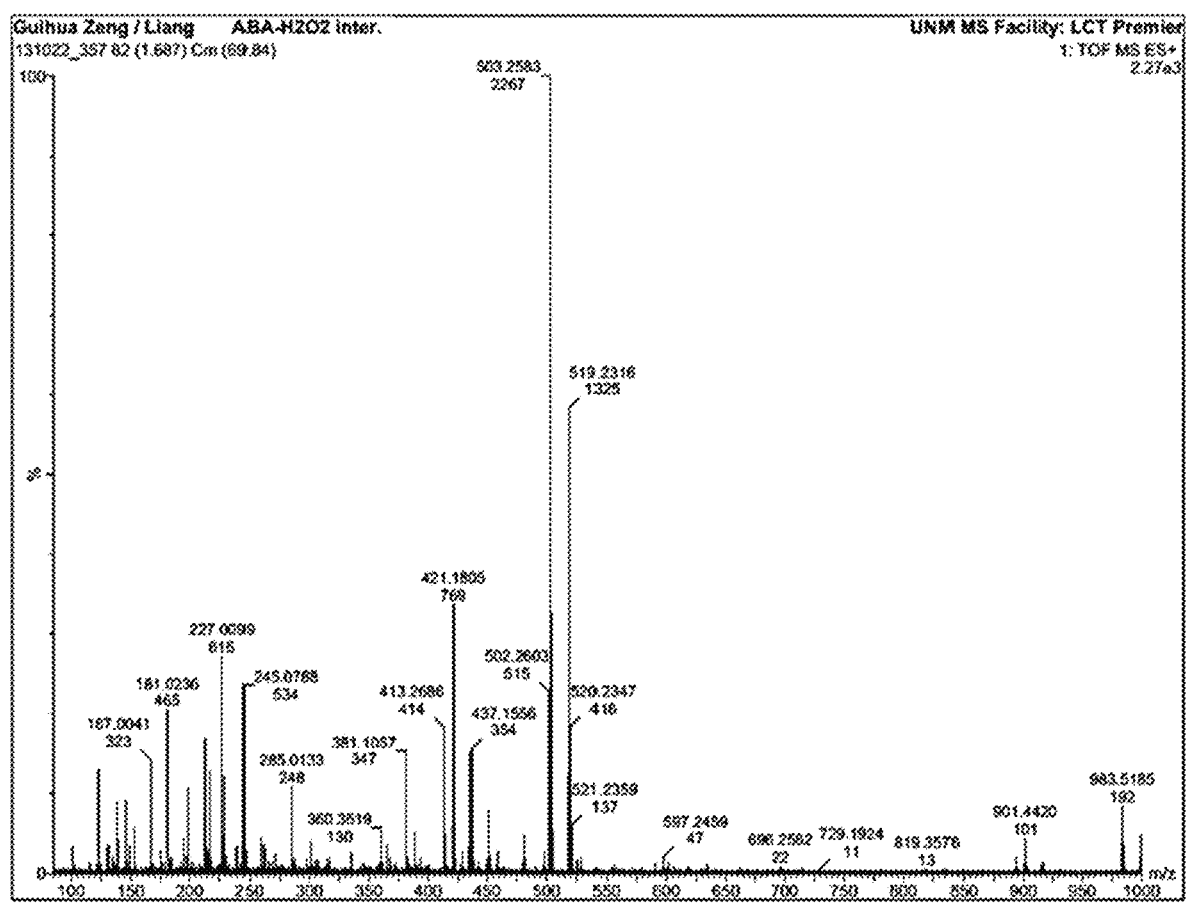
Figure 14:
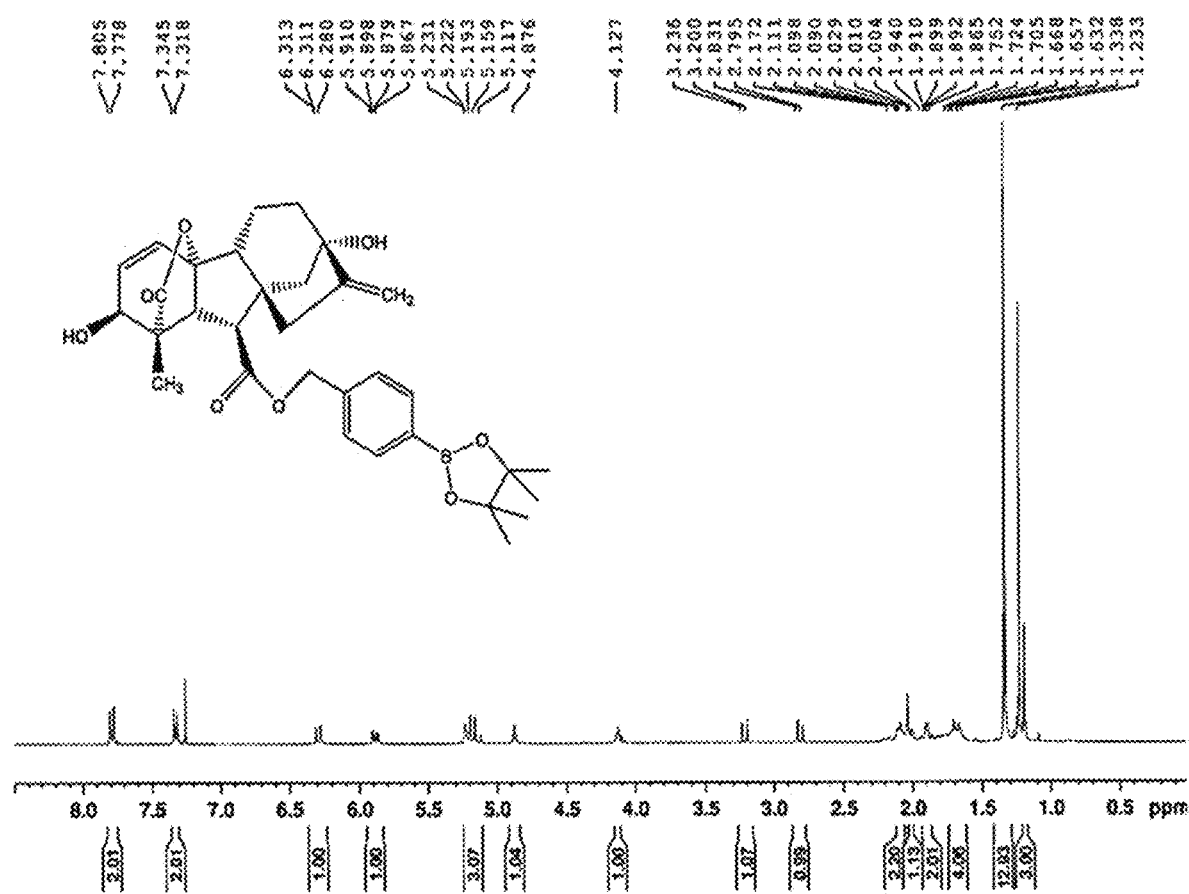
Figure 15:
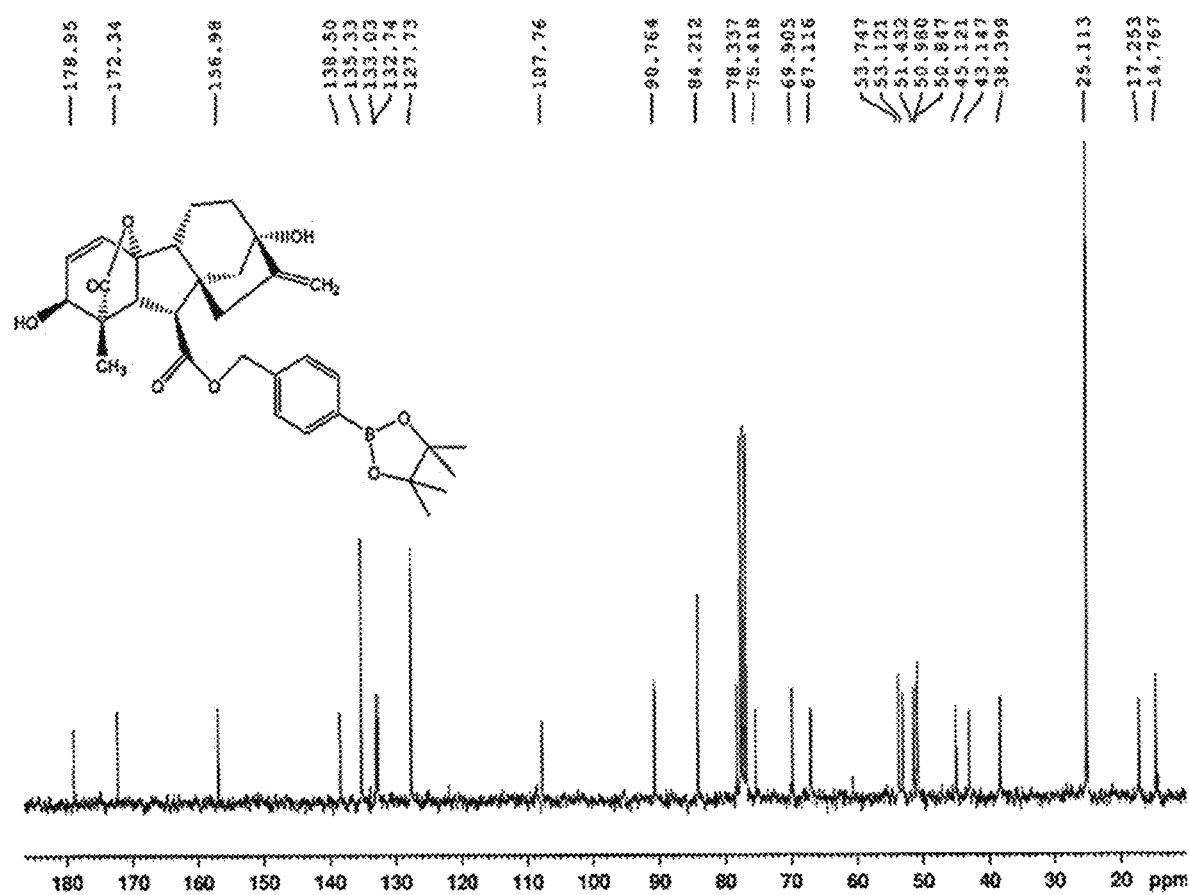
Figure 16:
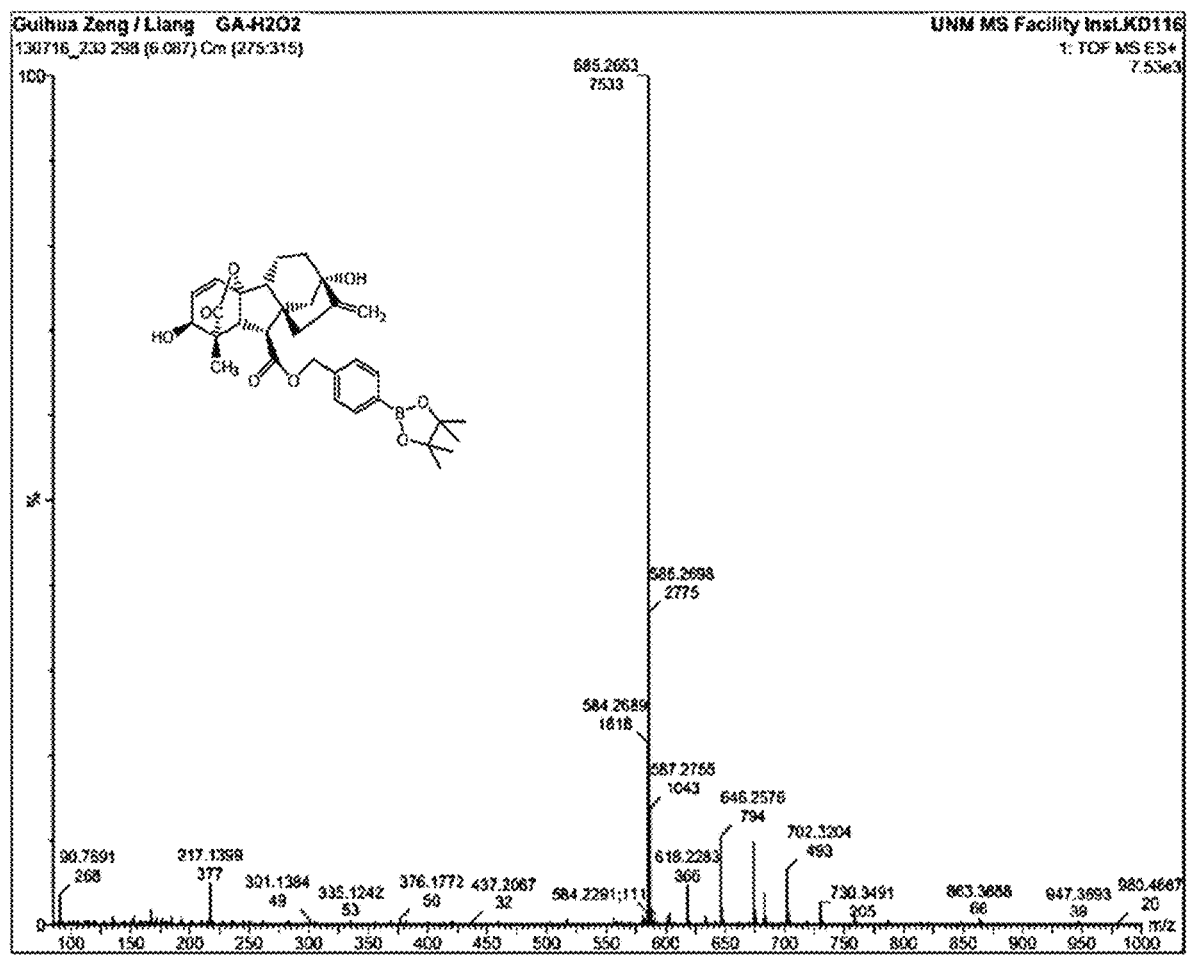
Figure 17:
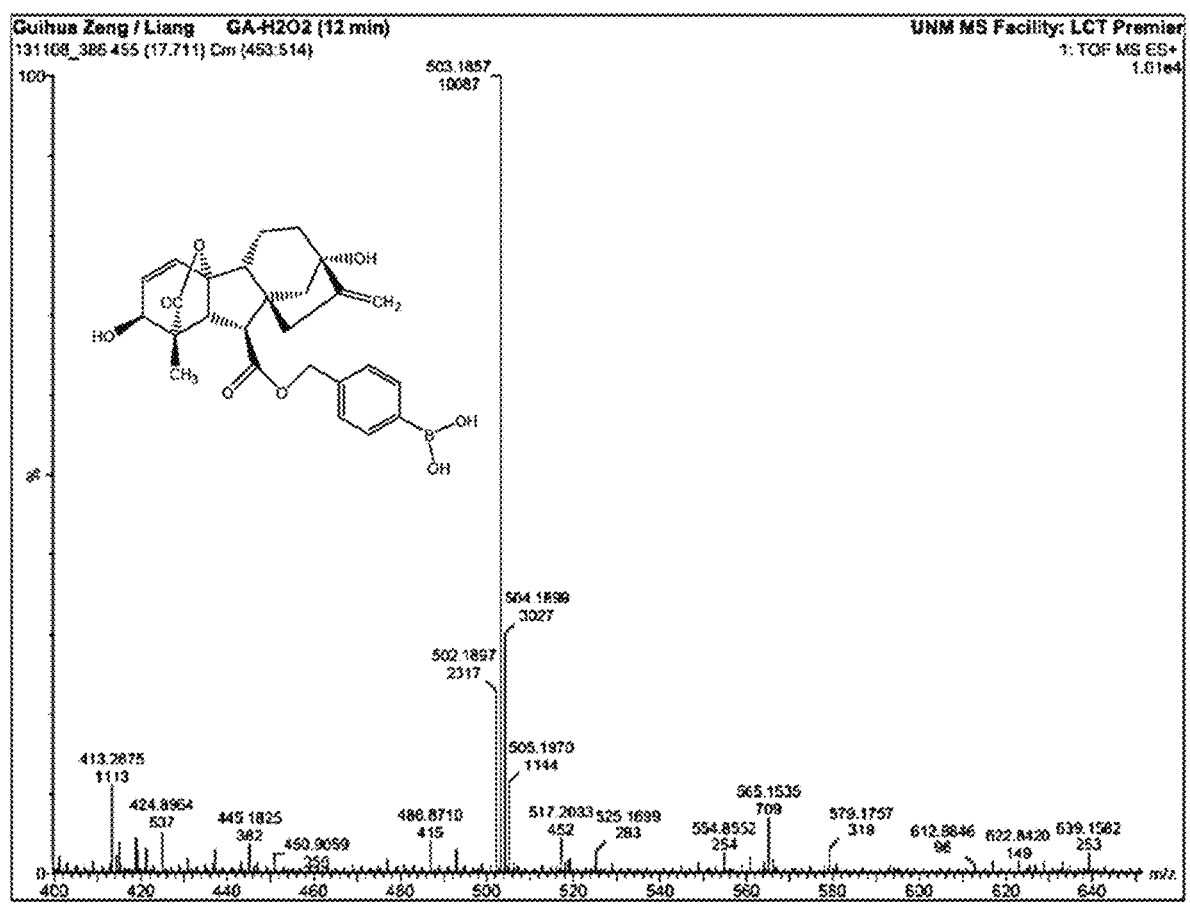
Figure 18:
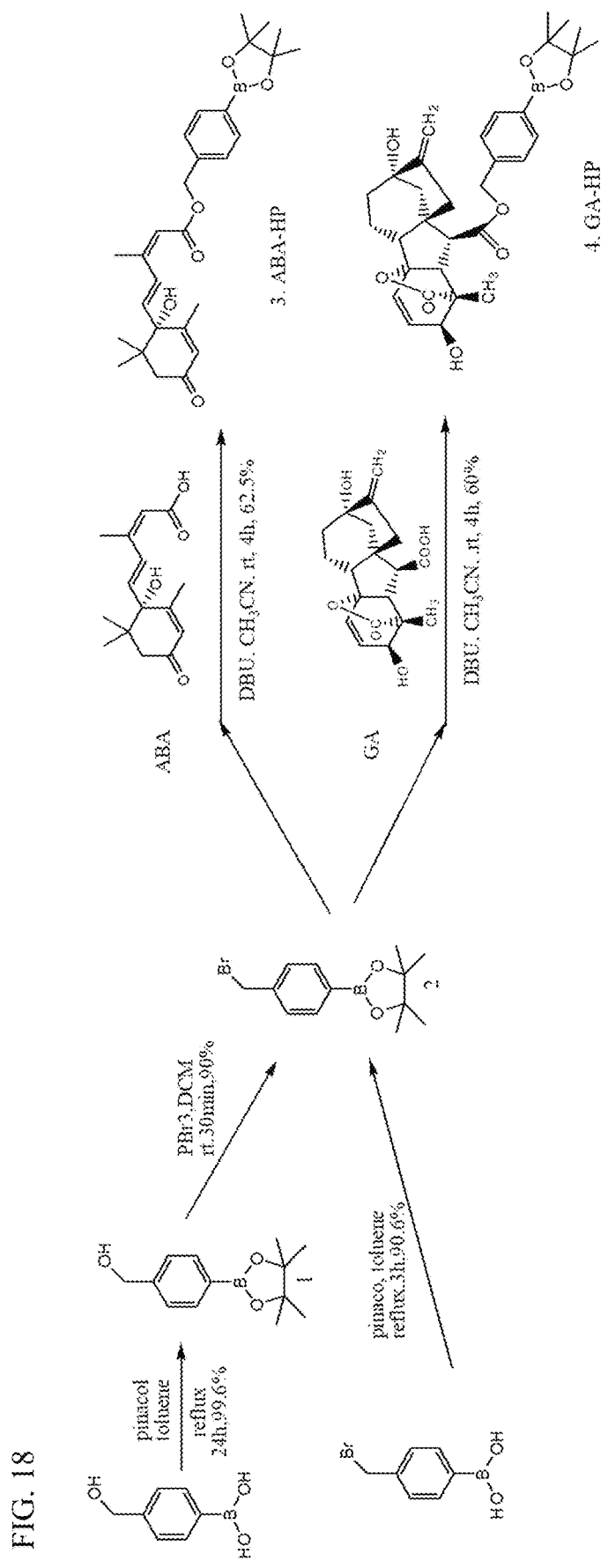

FIG. 10. ¹H-NMR of compound 2.
FIG. 11. ¹H-NMR of compound 3 (ABA-HP).
FIG. 12. ¹³C-NMR of compound 3 (ABA-HP).
FIG. 13. MS of ABA-HP and ABA-HP dimer.
FIG. 14. ¹H-NMR of compound 4 (GA-HP).
FIG. 15. ¹³C-NMR of compound 4 (GA-HP).
FIG. 16. MS of GA-HP.
FIG. 17. MS of partial hydrolyzed GA-HP.
FIG. 18. Characterization data of new compounds. Compound 2: ¹H-NMR (300.13 MHz, CDCl3), δ (ppm): 1.340 (12H, s), 4.488 (2H, s), 7.378-7.404 (2H, d, J=7.8 Hz), 7.772-7.798 (2H, d, J=7.8 Hz); Compound 3 (ABA-HP): ¹H-NMR (300.13 MHz, CDCl₃), δ (ppm): 0.997 (3H, s), 1.097 (3H, s), 1.334 (12H, s), 1.896 (3H, s), 2.004 (3H, s), 2.165 (1H, s), 2.254-2.311 (1H, d, J=17.1 Hz), 2.443-2.500 (1H, d, J=17.1 Hz), 5.155 (2H, s), 5.802 (1H, s), 5.917 (1H, s), 6.130-6.183 (1H, d, J=15.9 Hz), 7.345-7.372 (2H, d, J=8.1 Hz), 7.785-7.812 (2H, d, J=8.1 Hz), 7.855-7.910 (1H, d, J=16.5 Hz). ¹³C-NMR (75.48 MHz, CDCl₃), δ (ppm): 18.9, 21.3, 23.1, 24.3, 24.8, 41.5, 49.8, 65.7, 79.6, 83.8, 118.3, 127.0, 127.2, 128.1, 135.0, 136.5, 139.1, 149.7, 162.4, 165.6, 197.7; Compound 4 (GA-HP): ¹H-NMR (300.13 MHz, CDCl₃), δ (ppm): 1.198 (3H, s), 1.338 (12H, s), 1.632-2.172 (9H, m), 2.795-2.831 (1H, d, J=10.8 Hz), 3.200-3.236 (1H, d, J=10.8 Hz), 4.127 (1H, s), 4.876 (1H, s), 5.117-5.231 (3H, m), 5.867-5.910 (1H, dd, J=3.6, 9.3 Hz), 6.280-6.313 (1H, d, J=9.9 Hz), 7.318-7.345 (2H, d, J=8.1 Hz), 7.778-7.805 (2H, d, J=8.1 Hz). ¹³C-NMR (75.48 MHz, CDCl₃), δ (ppm): 14.8, 17.3, 25.1, 38.4, 43.1, 45.1, 50.8, 51.4, 51.4, 53.1, 53.7, 67.1, 69.9, 75.4, 78.3, 84.2, 90.8, 107.8, 127.1, 132.7, 133.0, 135.3, 138.5, 157.0, 172.3, 179.0. ESI-MS, m/z (M+Na)+ 585.

Figure 19:
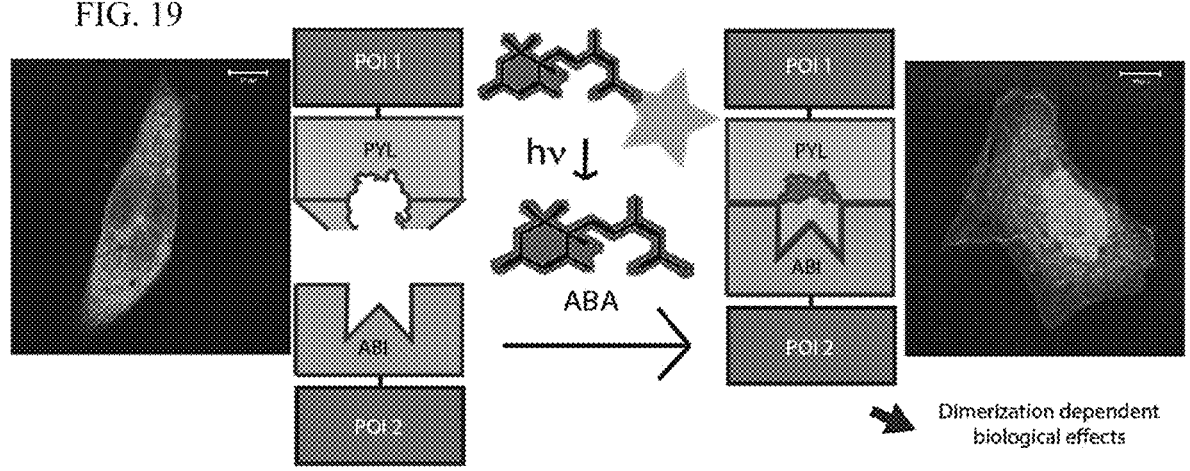

FIG. 19. Light activation of caged ABA can dimerize two proteins of interest (POIs) and induce downstream cellular processes. The induced proximity of any two POIs can lead to a wide variety of biological effects.

FIG. 20. Synthesis and photo-cleavage of Caged ABA. A) ABA was conjugated to the DMNB protecting group in a one-step synthesis. Irradiation with 365 nm light removes the DMNB group and results in the release of free ABA. B) HPLC analysis of the photo-cleavage reaction showed that irradiation of 100 μM ABA-DMNB can regenerate free ABA within 2 min.

Figure 21:
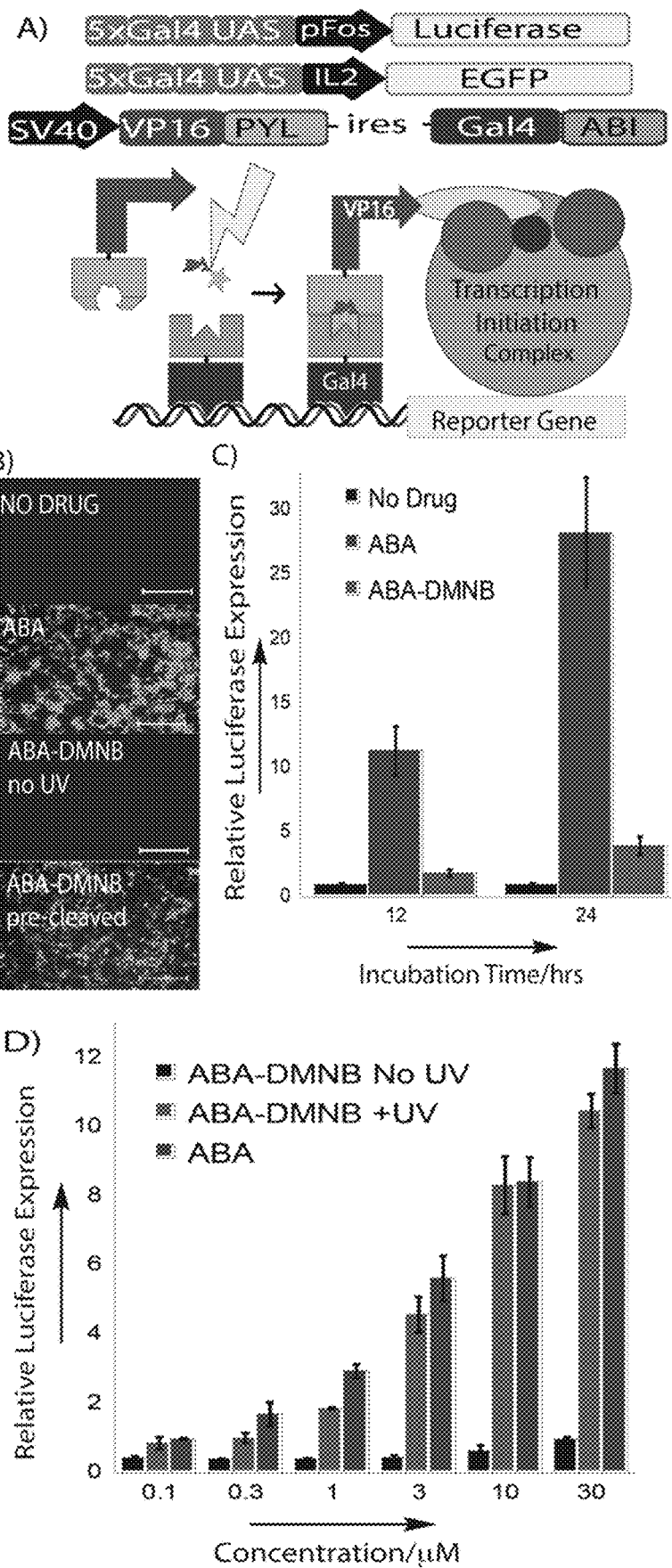

FIG. 21. Photo-triggered uncaging of ABA-DMNB can induce gene expression. A) Constructs and mechanism of ABA-dependent transcription initiation of a reporter gene. B) Induction of EGFP expression by 10 μM ABA, ABA-DMNB or UV-irradiated ABA-DMNB in EGFP reporter 293T cells. Scale bar 100 μm. C) Testing the stability of ABA-DMNB. CHO cells transfected with inducible luciferase expression constructs were incubated with ABA or ABADMNB for 12 and 24 h in the dark. D) Uncaging in cell culture and dosage dependence of light-controlled luciferase expression. CHO cells transfected with inducible luciferase constructs were treated with increasing dosages of ABA, or ABA-DMNB with or without UV irradiation. For C) and D), the relative luciferase expression fold changes were calculated based on transfected cells with no drug treatment. Error bars are SD (N=3).

Figure 22:
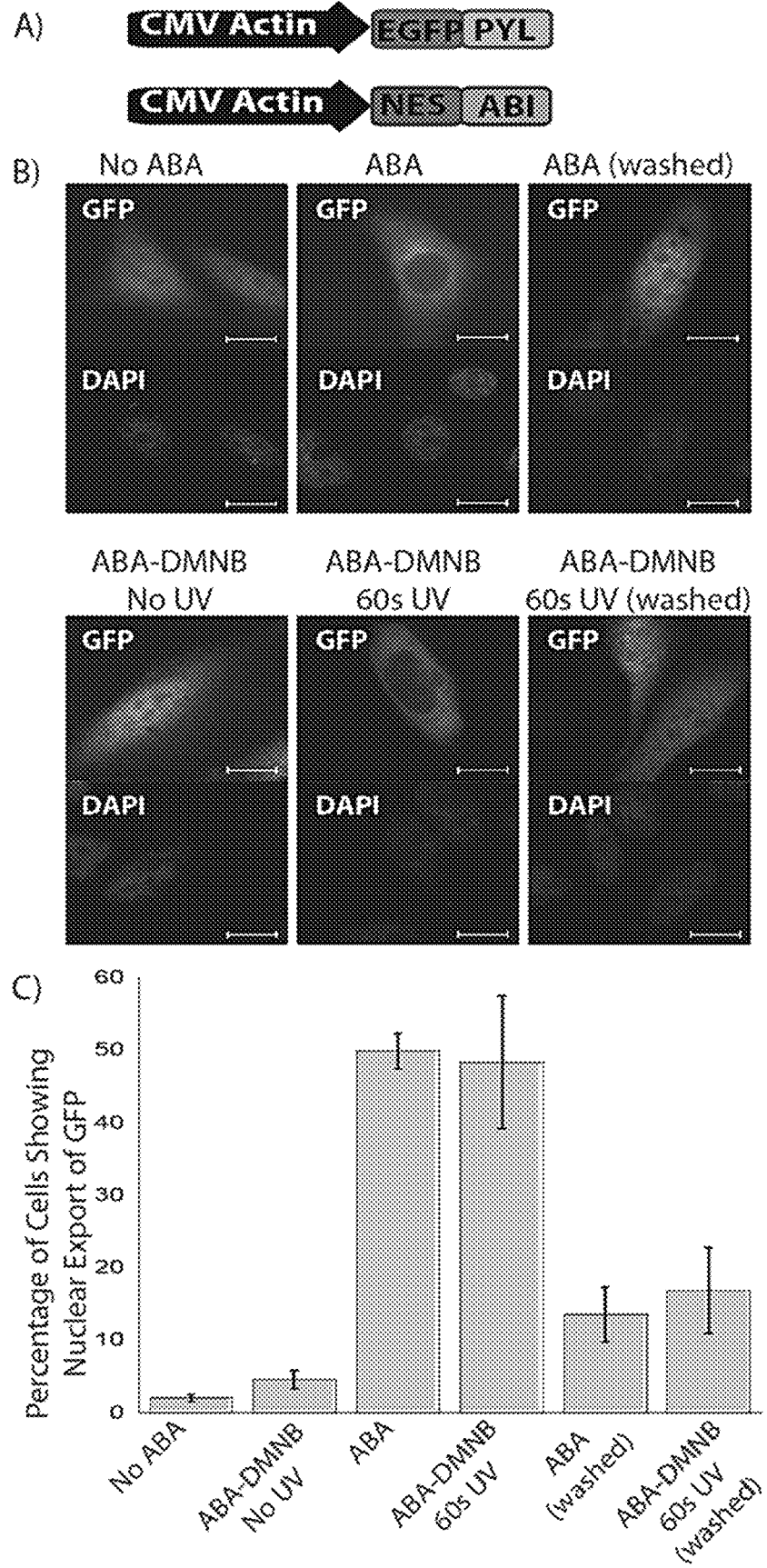

FIG. 22. Photo-uncaging of ABA-DMNB can induce protein translocation. A) Constructs expressing EGFP-PYL and nuclear export sequence (NES)-tagged ABI. B) CHO cells were transfected with these constructs to test the light induced EGFP translocation. Under conditions with no drug or with ABADMNB without irradiation, the EGFP-PYL was distributed throughout the cell. With the addition of ABA or the irradiation of added ABA-DMNB, the EGFPPYL was exported out of the nucleus. After repeated washing with fresh media, the dimerization was reversed and EGFP-PYL diffused back into the nucleus. Scale bar 10 μm. C) Quantitative analysis and statistics of EGFP-PYL translocation in EGFP expressing cells. Transfected and treated CHO cells were fixed and analyzed under a fluorescence microscope for nuclear export. Cells were categorized as showing nuclear export of EGFP when the intensity in the nucleus was less than 60% of that in the cytoplasm. Cells were counted from three separate experiments with N>50 for each experiment.

Figure 23:
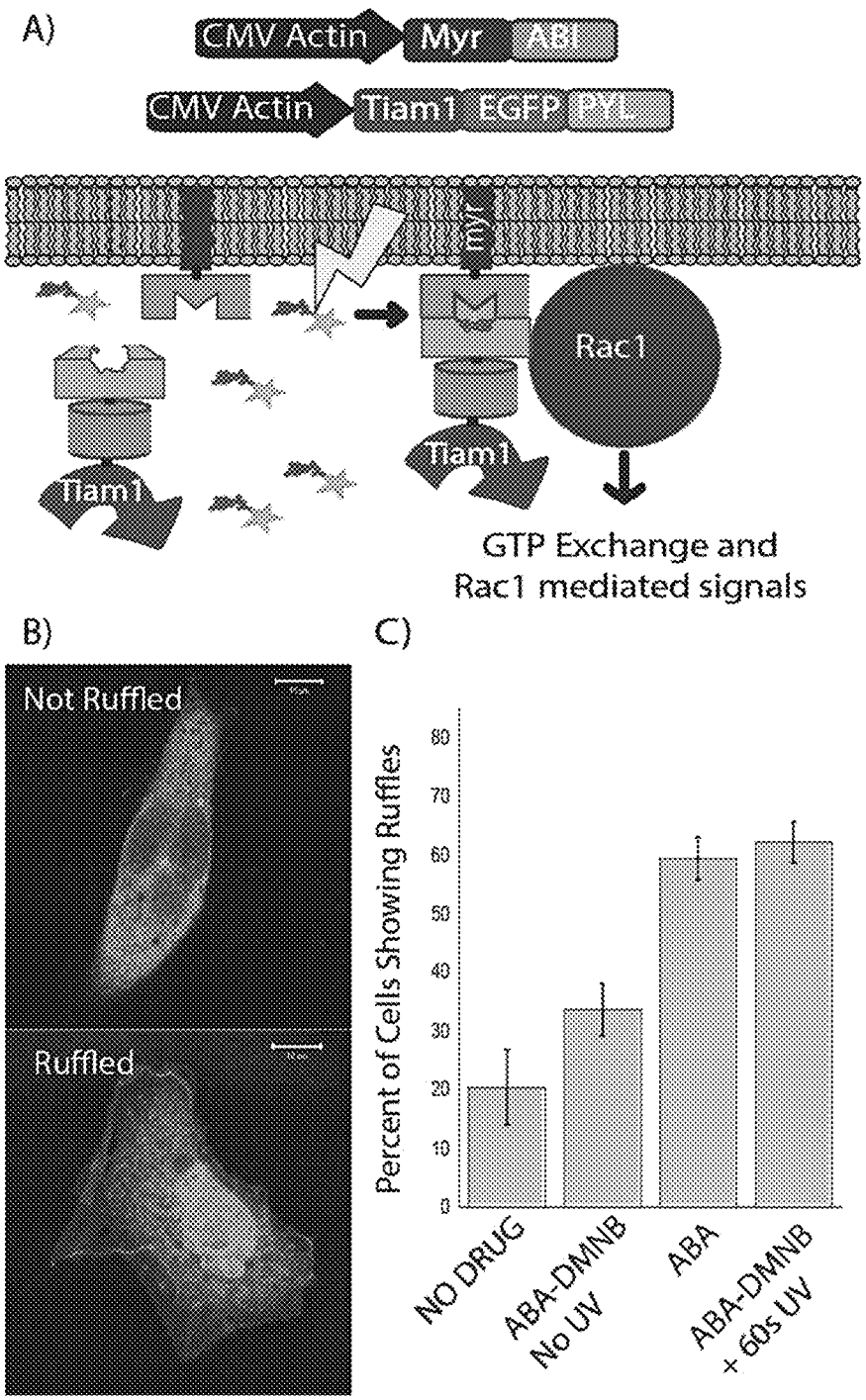

FIG. 23. Caged ABA can be released to induce signal transduction to produce morphological changes. A) Constructs and mechanism of ABA-inducible membrane localization of Tiam1 and the initiation of Rac1 signaling. B) Examples of cell morphology classified as non-ruffled (top) or ruffled (bottom). Scale bar 10 μm. C) Quantitative analysis and statistics of induced ruffling. Cells were counted and classified based upon the appearance of ruffled or non-ruffled morphology in EGFP expressing cells. Percentages of cells showing the ruffled morphology were calculated from three experiments with N>50 for each experiment. Cultures that were given ABA or ABA-DMNB with irradiation showed a higher percentage of ruffled cell compared to cultures that were given ABA-DMNB without irradiation or no drug.

Figure 24:
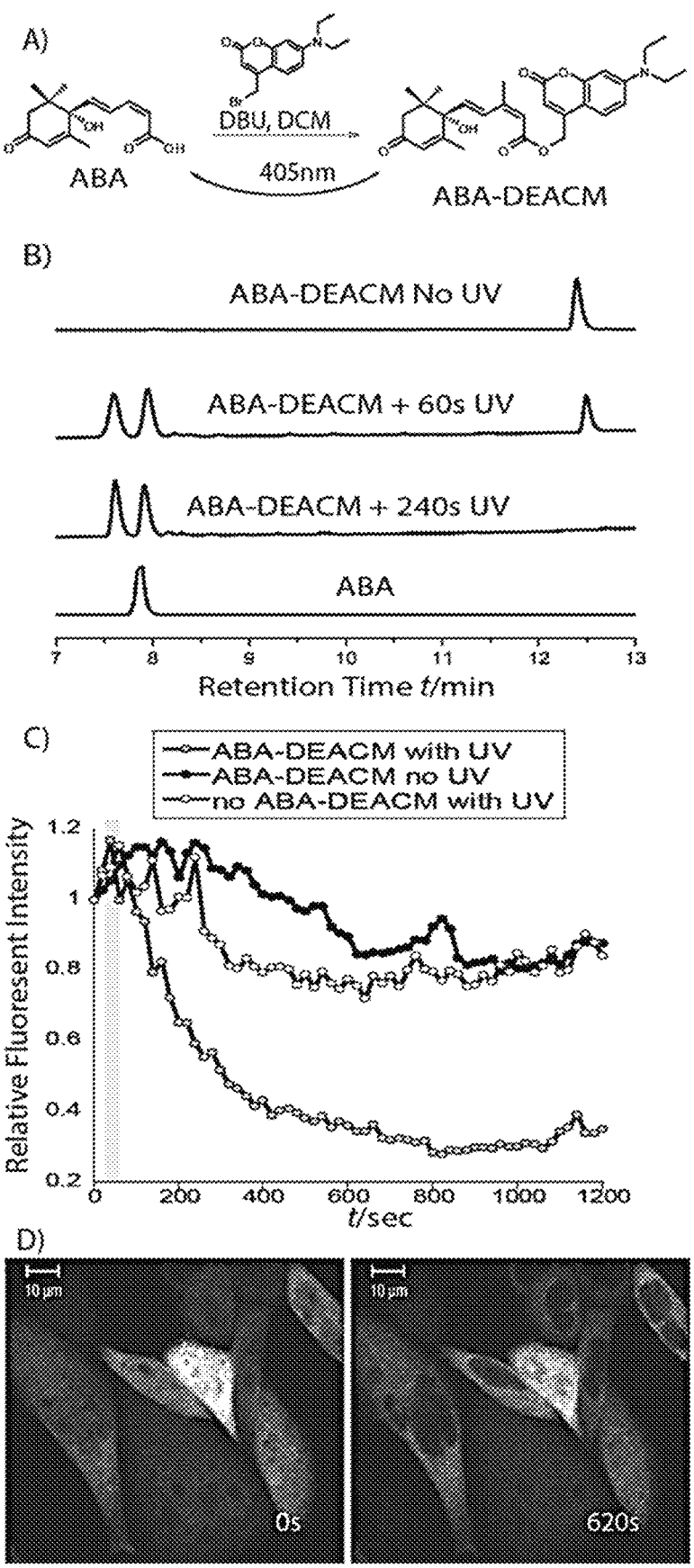

FIG. 24. ABA-DEACM for live cell experiments. A) Synthesis and photocleavage of ABA-DEACM by irradiation with 405 nm light. B) HPLC analysis of irradiated ABA-DEACM showed complete cleavage within 4 min. C) Quantitative analysis of EPFG-PYL nuclear export in live cell imaging under a confocal microscope. EGFP-PYL was monitored for 20 min and the ratio of the fluorescent intensity of the nucleus to the cytoplasm was calculated as a function of time. Grey bar indicates the period of irradiation with 405 nm laser equipped on the confocal microscope. D) Images of CHO cells incubated with ABA-DEACM before (0 sec) and after (620 sec) irradiation at 4 sec. Scale bar 10 μm. The data in C) and D) are representative data from three independent experiments.

Figure 25:
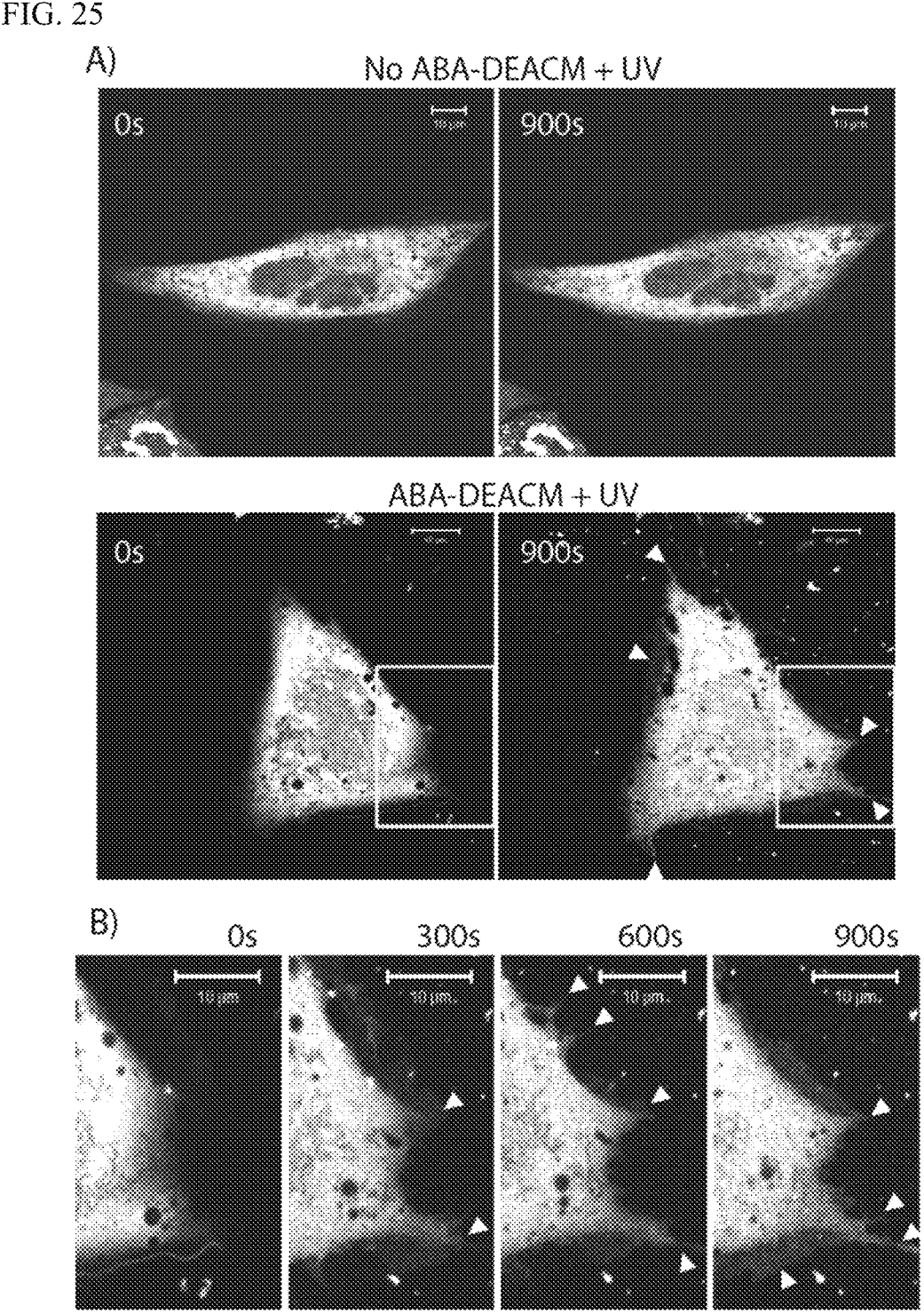

FIG. 25. Photo-uncaged ABA-DEACM induced cytoskeletal remodeling. A) CHO cells were transfected with myr-ABI and EGFP-PYL-Tiam1 constructs and irradiated with 405 nm light with or without the presence of ABA-DEACM. No cytoskeletal remodeling was observed for cells that were irradiated without the presence of ABA-DEACM. On the contrary, the formation of fillopodia and lemellopodia (arrows) was observed within 15 min of irradiation with 405 nm light in the presence of ABA-DEACM. Scale bar 10 μm. Images shown are representative results repeated in three wells for three independent experiments. B) The enlarged images of the outlined region in A) at different time points during the time course of imaging after uncaging. Membrane ruffling can be observed starting at 5 min.

Figure 26:
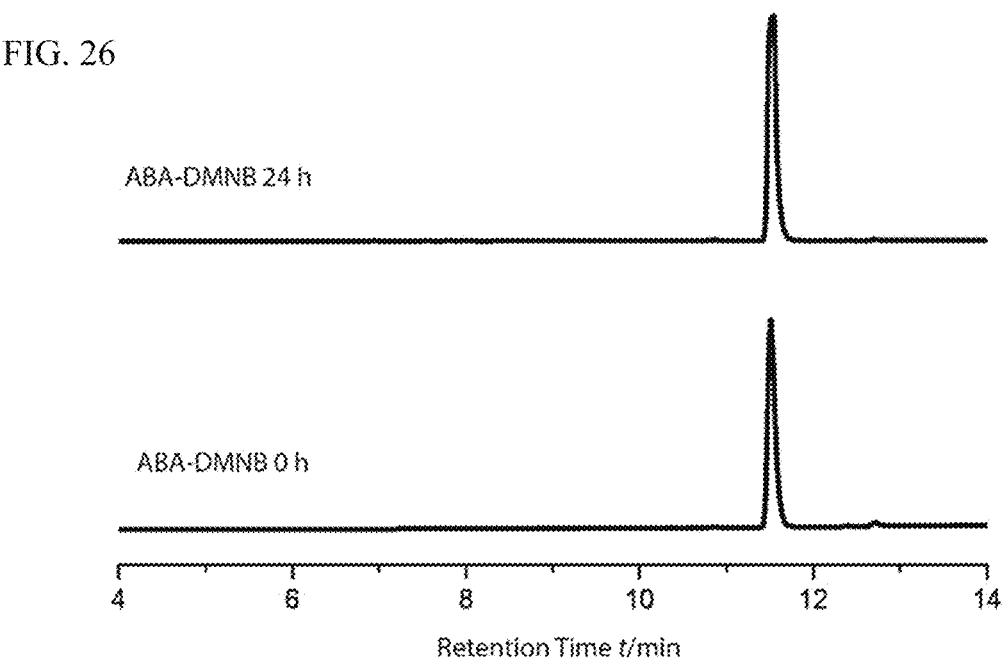

FIG. 26. Chemical stability of ABA-DMNB. ABA-DMNB was incubated in 70% HEPES buffer/30% DMSO at 37° C. for 24 h in the dark. The samples were analyzed by HPLC. The peak at 24 h is identical to the one at 0 h indicating no chemical decomposition of ABA-DMNB in the aqueous solution.

Figure 27:
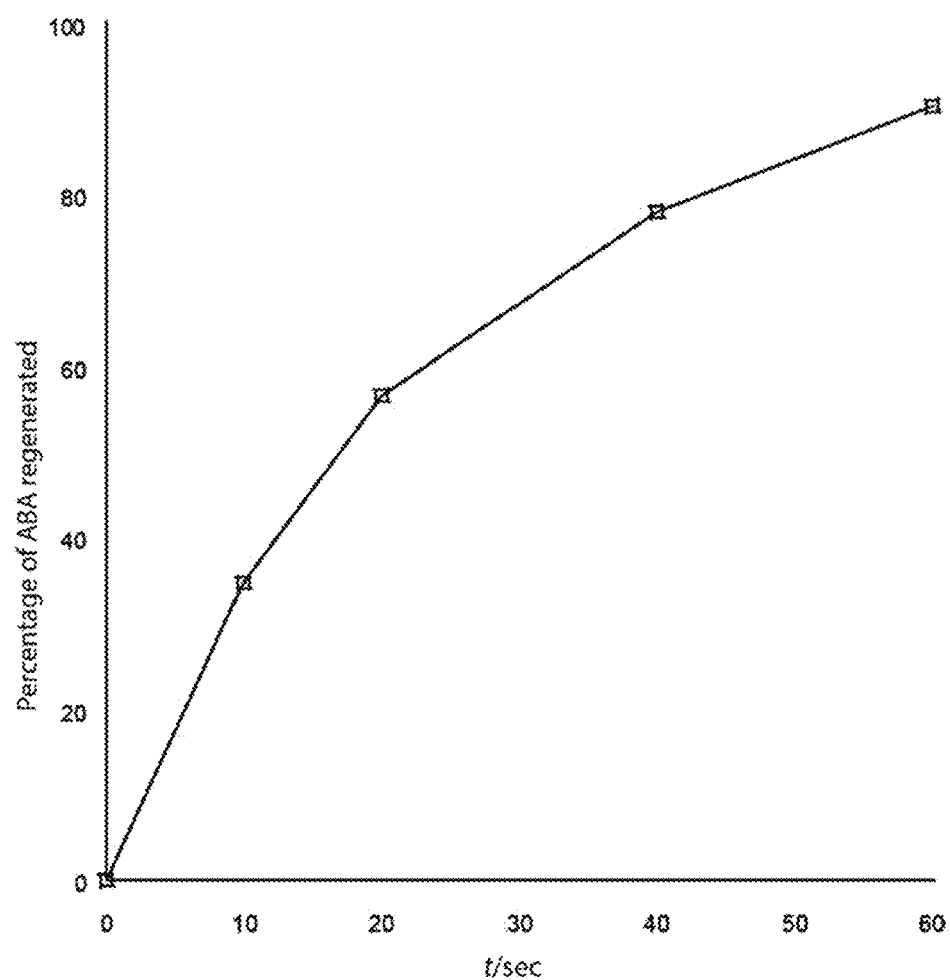

FIG. 27. Uncaging of ABA-DMNB. ABA-DMNB was dissolved in DMSO at 10 μM and irradiated with 365 nm light for indicated time (x-axis) from the fluorescence microscope and analyzed by HPLC. The areas under the curves were integrated to determine the relative amount of absorbance of each molecule present at 250 nm. The molar absorptivity of both free and caged ABA at 250 nm was measured, which was used to calculate the concentration of each species from the intensity of absorbance at 250 nm. The relative concentration of each compound was used to calculate the percent concentration of free ABA relative to the concentration of total ABA species (both caged and uncaged). This result showed that ABA can be rapidly regenerated from the photo-uncaging of ABA-DMNB within a min.

Figure 28:
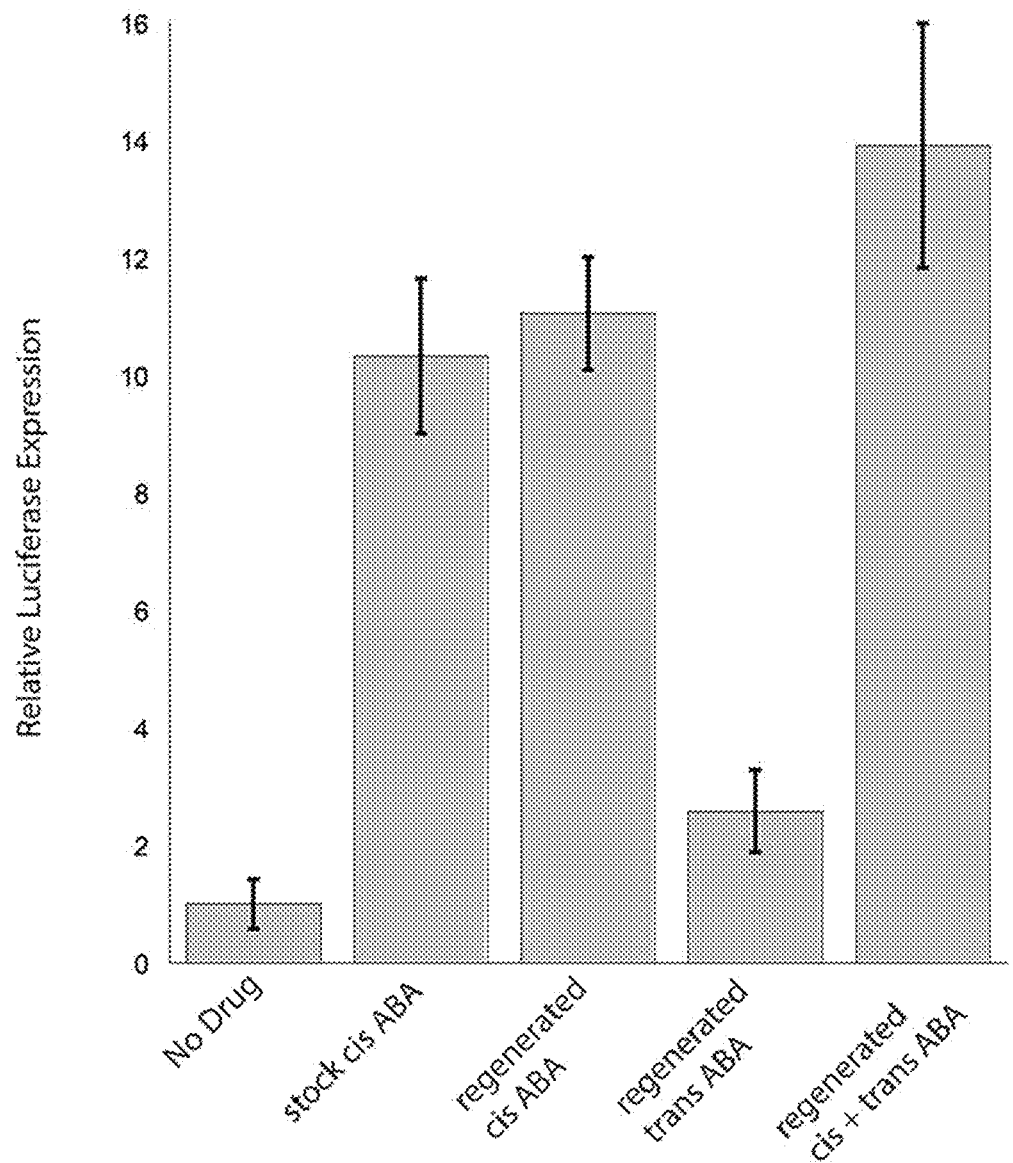

FIG. 28. Biological activity of regenerated ABA isomers. CHO cells were transfected with the ABA-inducible luciferase reporter constructs. Cultures were incubated for 24 h with ABA isomers that were produced through photo-cleavage and purified from HPLC. Cells were incubated with 10 μM stock cis ABA, regenerated 2-cis ABA, regenerated 2-trans ABA, and 10 μM each of regenerated 2-cis and 2-trans ABA. The relative luciferase expression fold-changes were calculated based on cells with no drug treatment. Error bars are SD (N=3).

Figure 29:
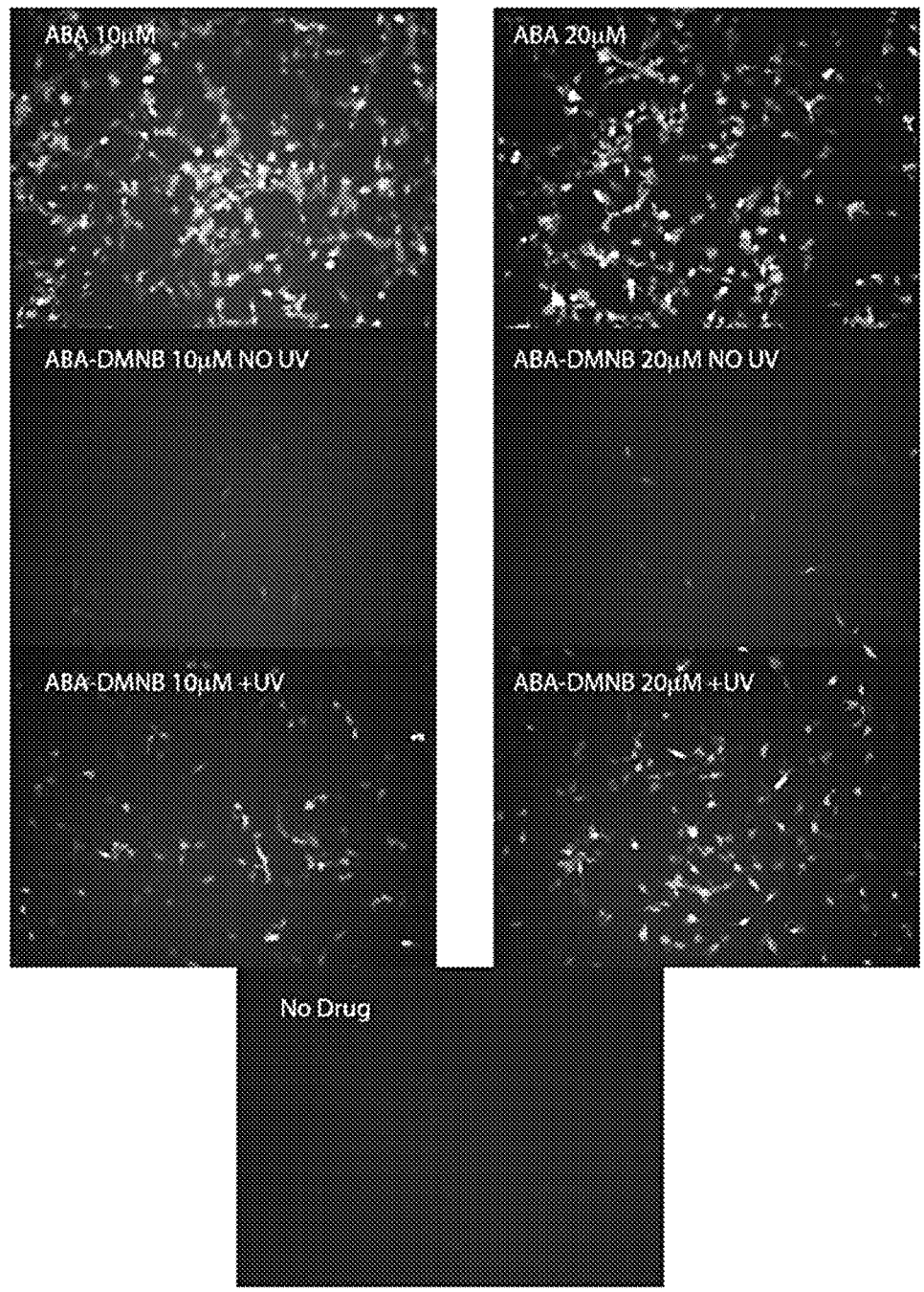

FIG. 29. Light-induced EGFP expression in cell culture. HEK 293T EGFP reporter cells were plated for 24 h and then incubated with ABA, ABA-DMNB, or ABA-DMNB with UV irradiation at indicated concentrations. Images were taken with the fluorescence microscope 12 h after molecules were added.

Figure 30:
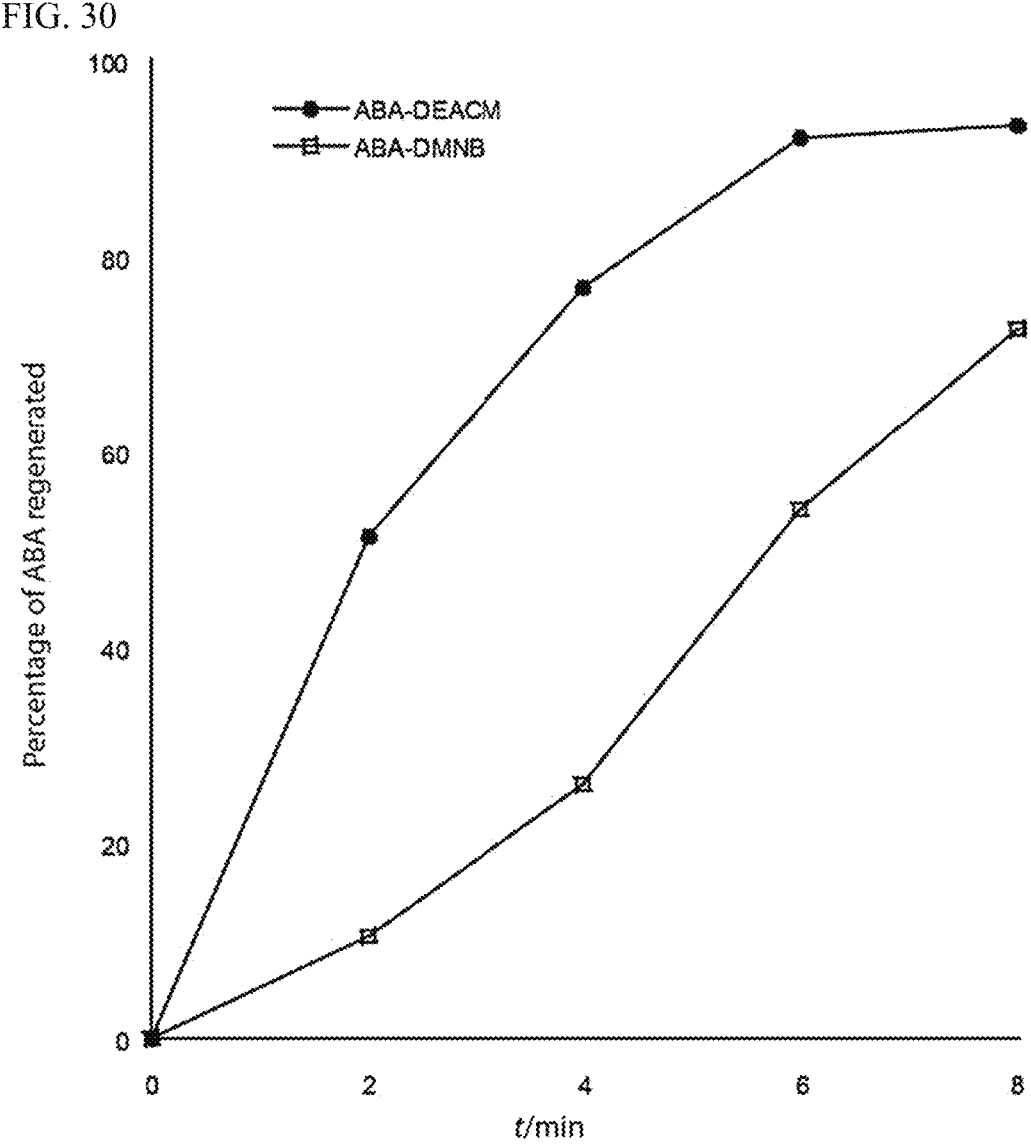

FIG. 30. Photo-cleavage of ABA-DEACM and ABA-DMNB by 405 nm light. 60 μL of ABA-DEACM in DMSO at 10 μM was irradiated with 405 nm light for the indicated amount of time (x-axis) in a 96-well plate. 50 μL of each sample was run through HPLC for analysis. The areas under the curves were integrated to determine the relative amount of absorbance of each molecule present at 250 nm. The molar absorptivity of both free and caged ABA at 250 nm was measured, which was used to calculate the concentration of each species from the intensity of absorbance at 250 nm. The relative concentrations of each compound were used to calculate the percent concentration of free ABA relative to the concentration of total ABA species.

Figure 31:
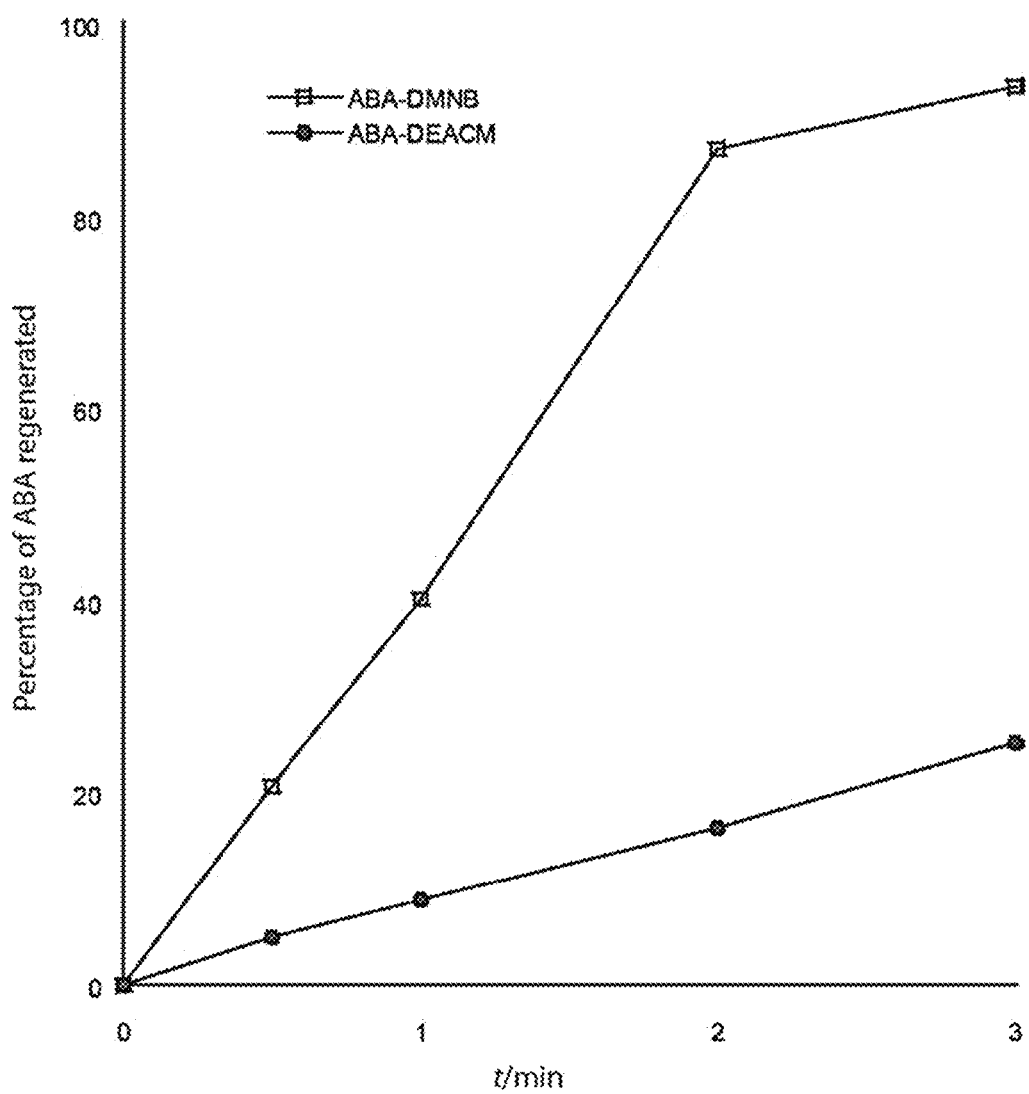

FIG. 31. Photo-cleavage of ABA-DMNB and ABA-DEACM by 365 nm light. 100 μL of ABA-DMNB and ABA-DEACM in DMSO at 10 μM were irradiated by the fluorescence microscope with 365 nm light for the indicated amount of time (x-axis) in a 24-well plate. 50 μL of each sample was run through the HPLC for analysis. The areas under the curves were integrated to determine the relative amount of absorbance of each molecule present at 250 nm. The molar absorptivity of both free and caged ABA at 250 nm was measured, which was used to calculate the concentration of each species from the intensity of absorbance at 250 nm. The relative concentrations of each compound were used to calculate the percent concentration of free ABA relative to the concentration of total ABA species. The results showed that ABA-DEACM cannot be cleaved effectively under 365 nm light and selective uncaging of ABA-DMNB is possible in the presence of ABA-DEACM.

Figure 32:
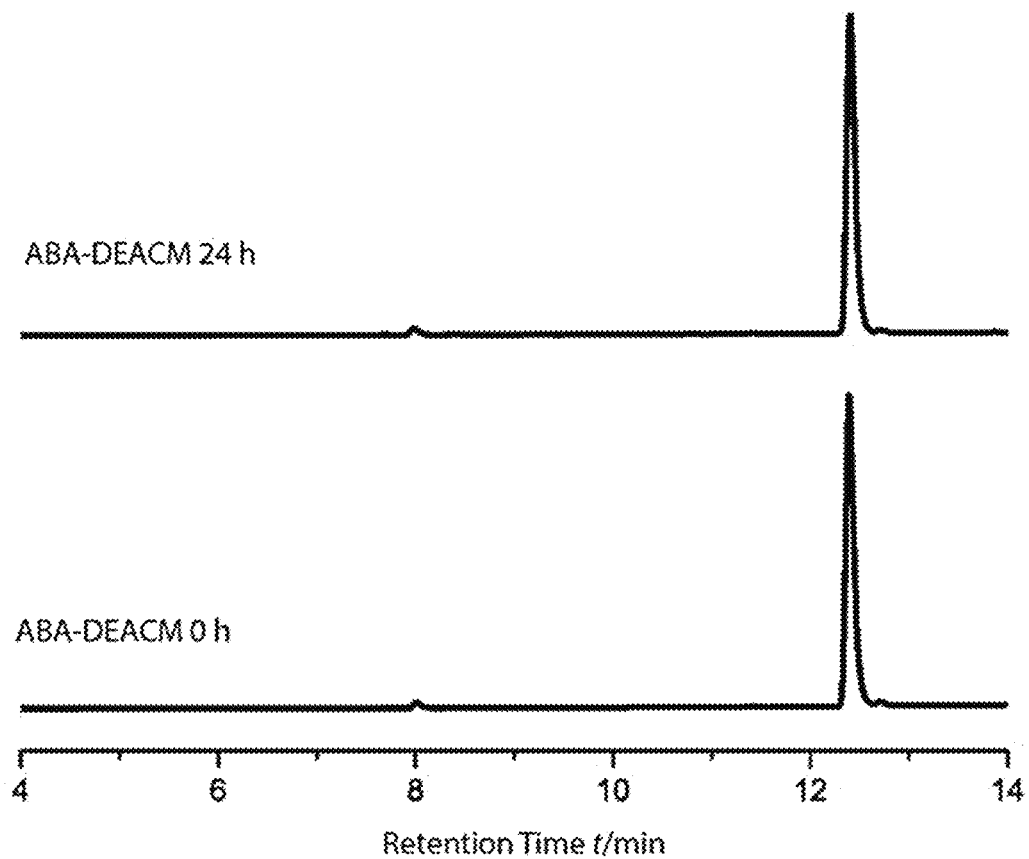

FIG. 32. Chemical stability of ABA-DEACM. ABA-DEACM was incubated in 70% HEPES buffer/30% DMSO at 37° C. for 24 h in the dark. The samples were analyzed by HPLC and absorbance was monitored at 250 nm. The peak at 24 h is identical to the one at 0 h indicating no chemical decomposition of ABA-DEACM in the aqueous solution.

Figure 33:
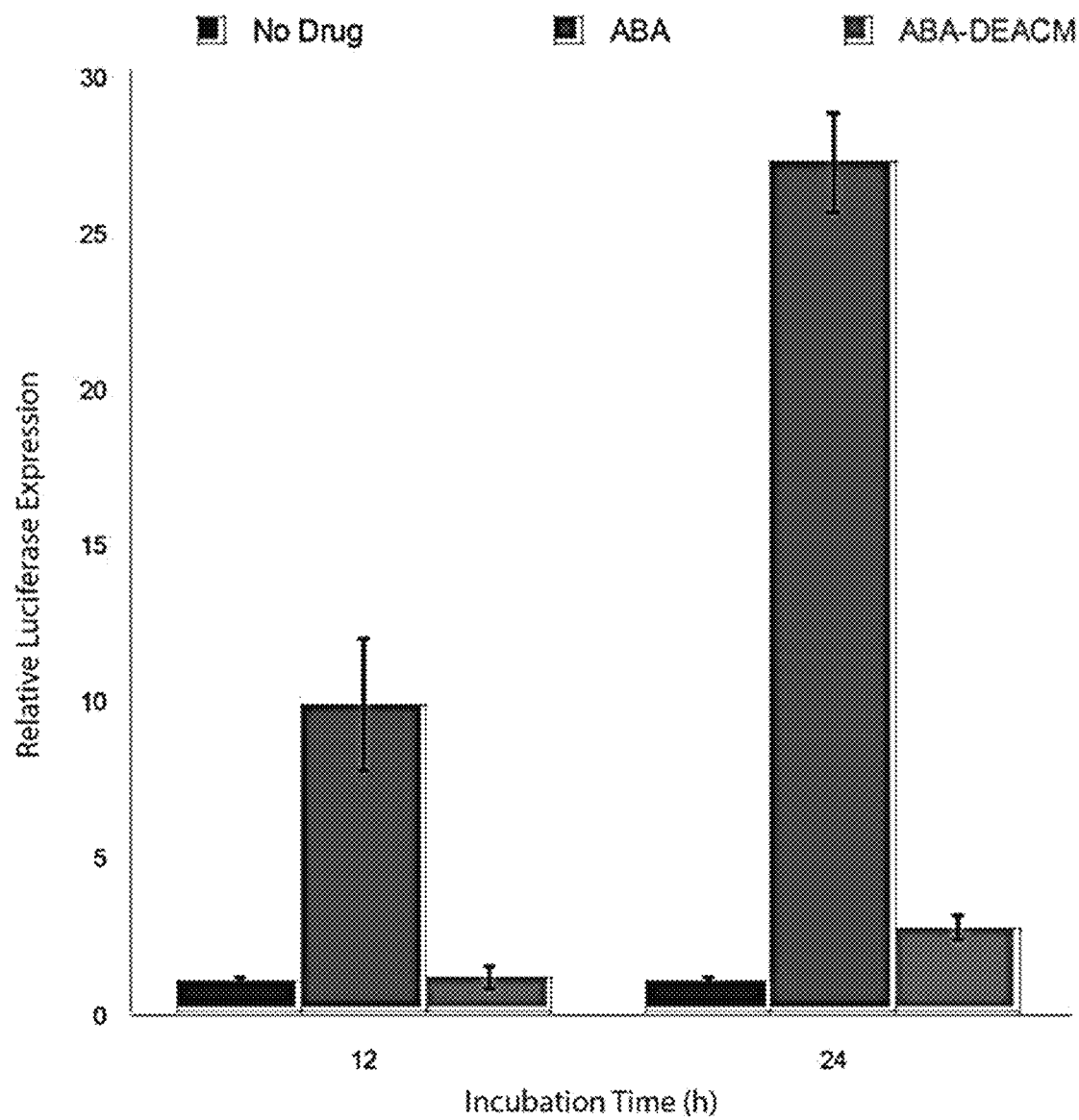

FIG. 33. Cellular stability of ABA-DEACM. CHO cells were transfected with ABA-inducible luciferase reporter constructs. Cells were then incubated with 10 μM ABA or ABA-DEACM in the dark for 12 or 24 h. The cell lysates were used for luciferase assay. The relative luciferase expression fold changes were calculated based on cells with no drug treatment. Error bars are SD (N=3).

Figure 34:
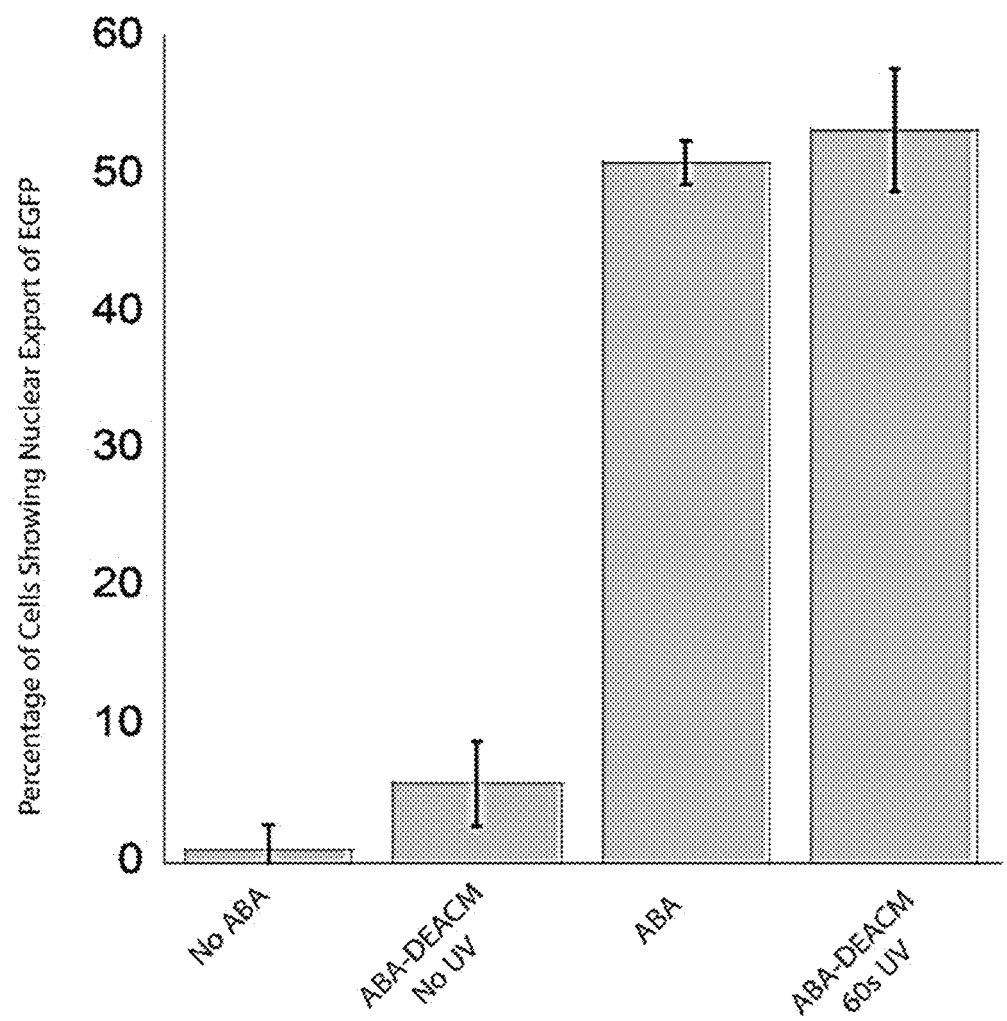

FIG. 34. Photo-uncaging of ABA-DEACM to induce EGFP nuclear export. CHO cells were transfected with the ABA-inducible EGFP nuclear export constructs and then treated with 10 μM ABA or ABA-DEACM with or without 405 nm light irradiation. Cells were then fixed on slides and analyzed under a fluorescence microscope. Cell were categorized as displaying nuclear export of EGFP when the fluorescent intensity of the nucleus was less than 60% of the intensity of the cytoplasm. Percentages of cells showing nuclear export of EGFP were calculated from three experiments where N>50 for each experiment.

Figure 35:
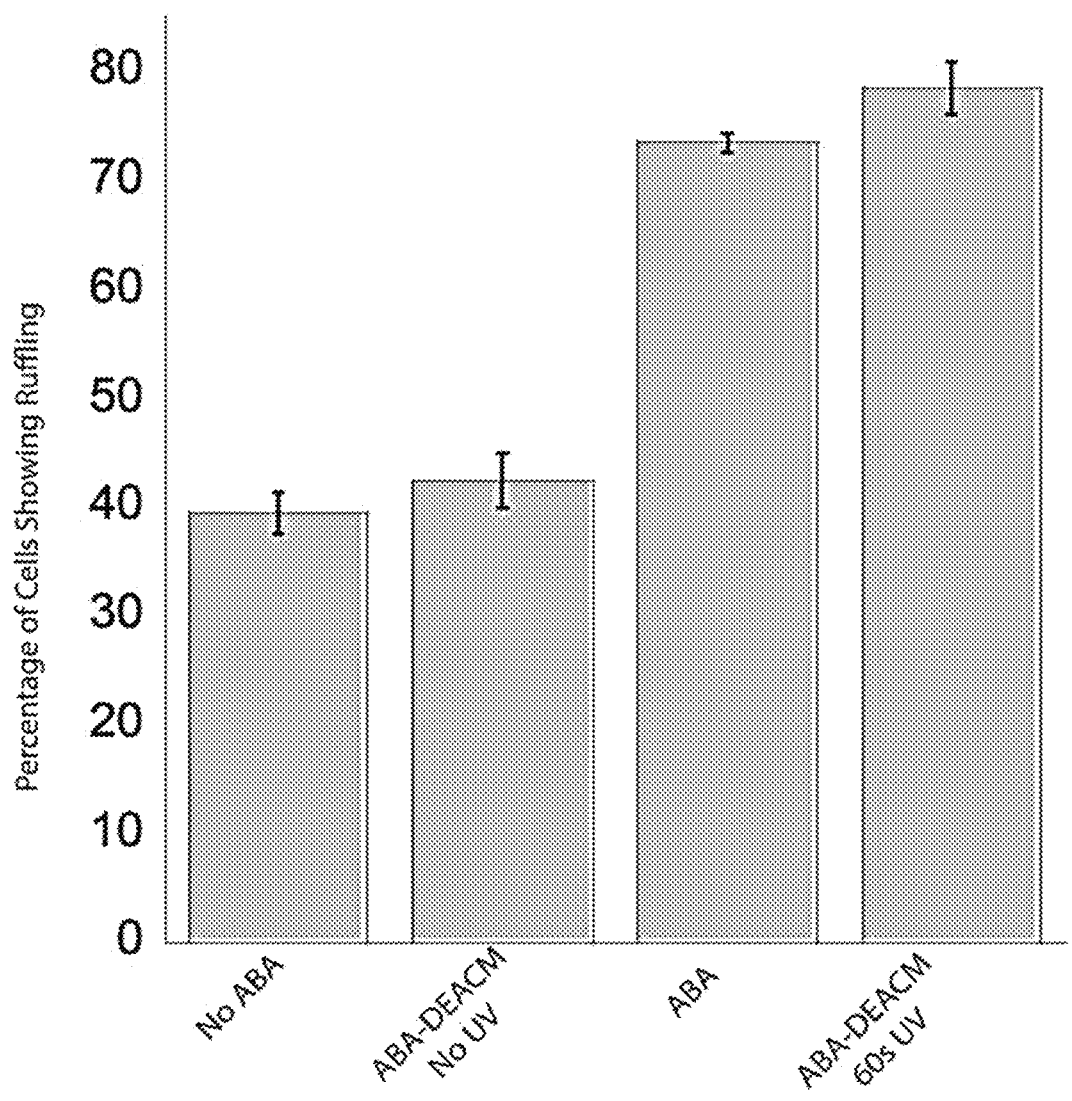

FIG. 35. Photo-uncaging of ABA-DEACM to induce ruffling. CHO cells were transfected with the ABA-inducible Tiam1 membrane localization constructs and then treated with 10 μM ABA or ABA-DEACM with or without 405 nm light irradiation. Cells were then fixed on slides and analyzed under a fluorescence microscope. Cells were counted and classified based upon the appearance of ruffled or non-ruffled morphology. Percentages of cells showing a ruffled morphology were calculated from three experiments where N>50 for each experiment.

Figure 36:
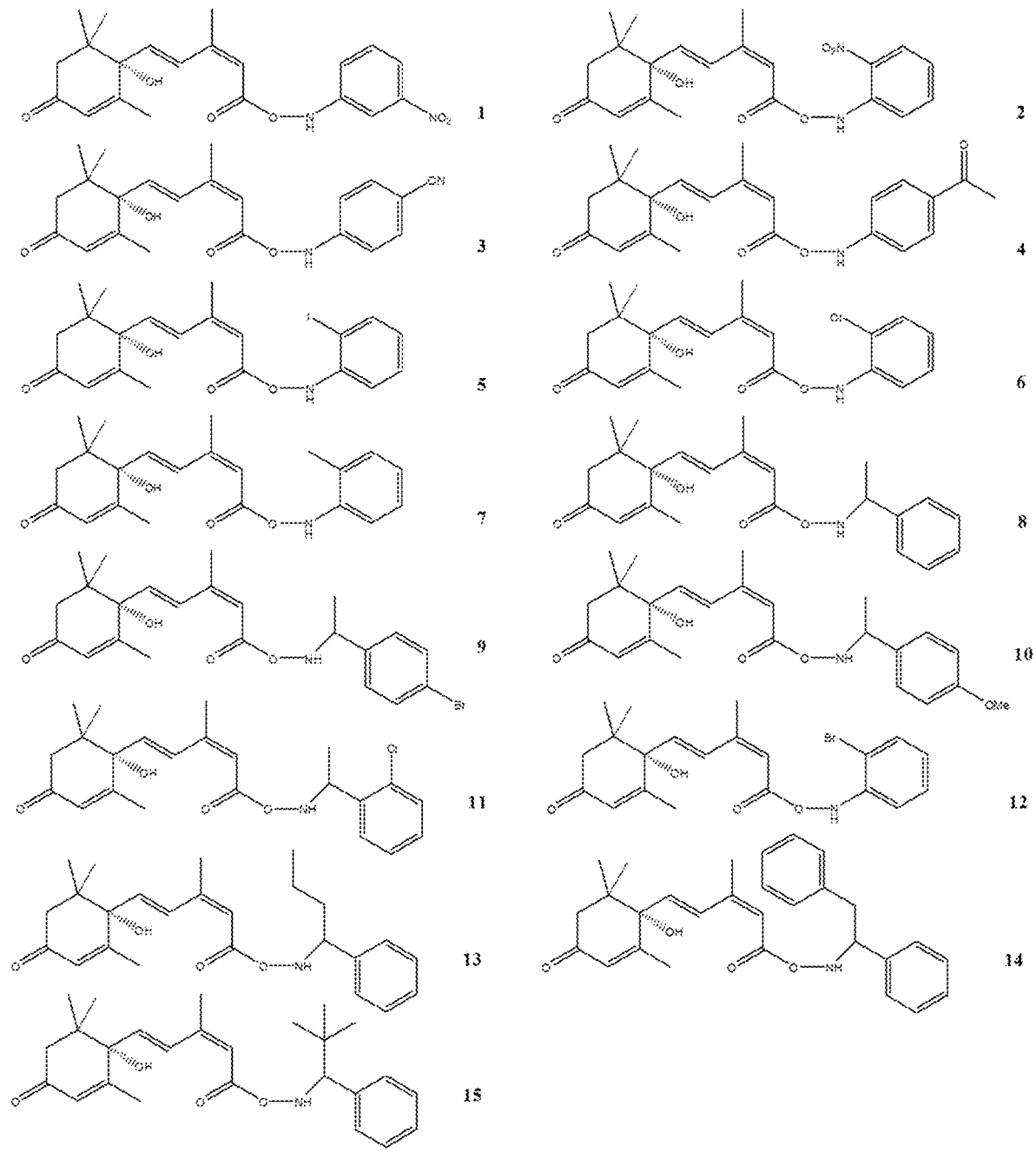

FIG. 36. Exemplary $Fe^{2+}$-sensing ABA-based inducer compounds.

Figure 37:
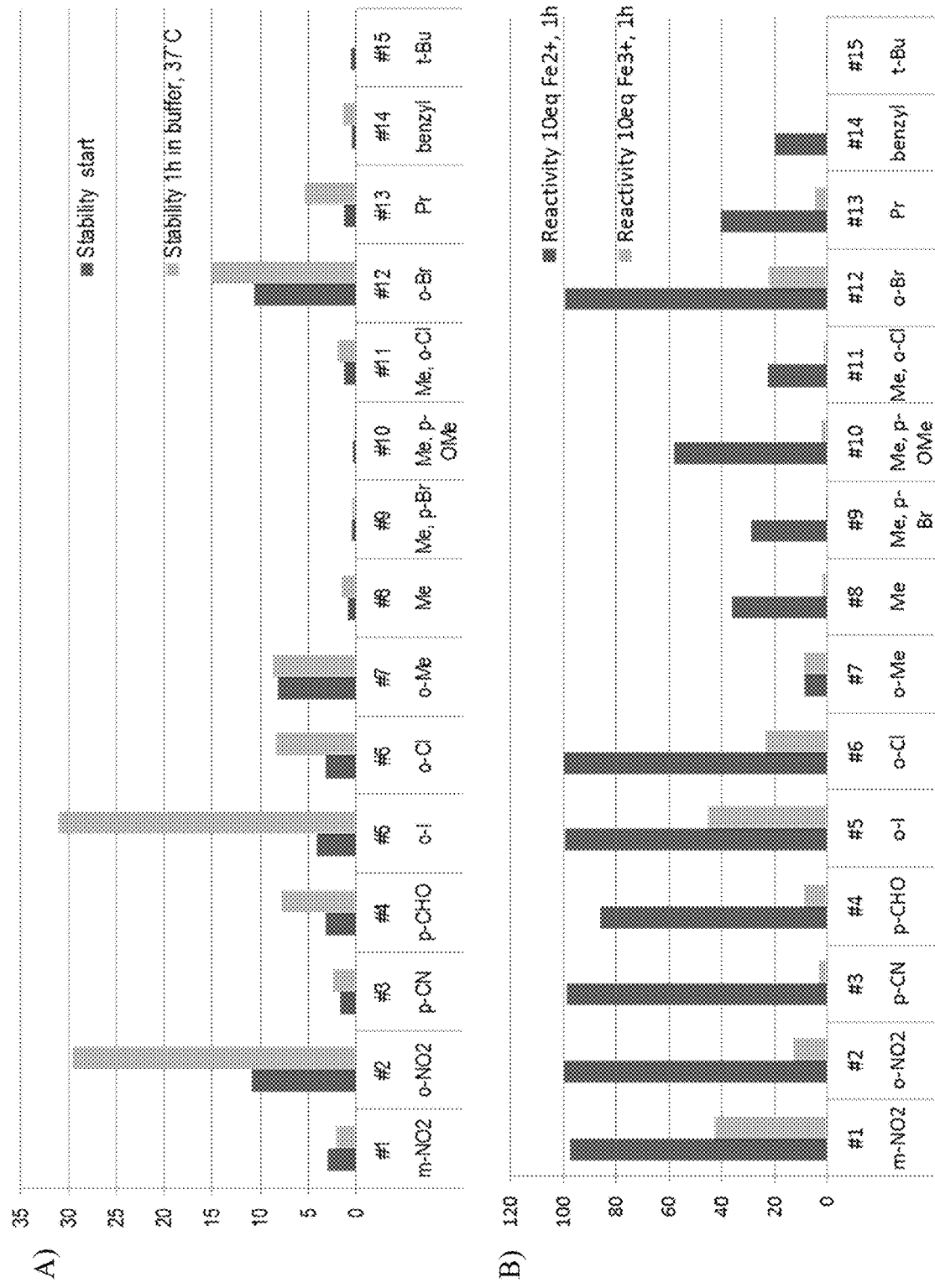
Figure 37:
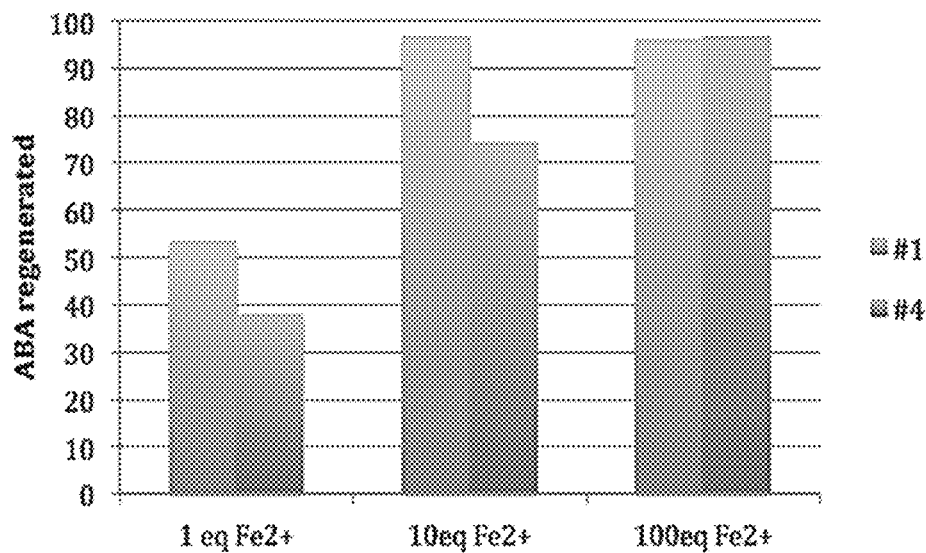
Figure 37:
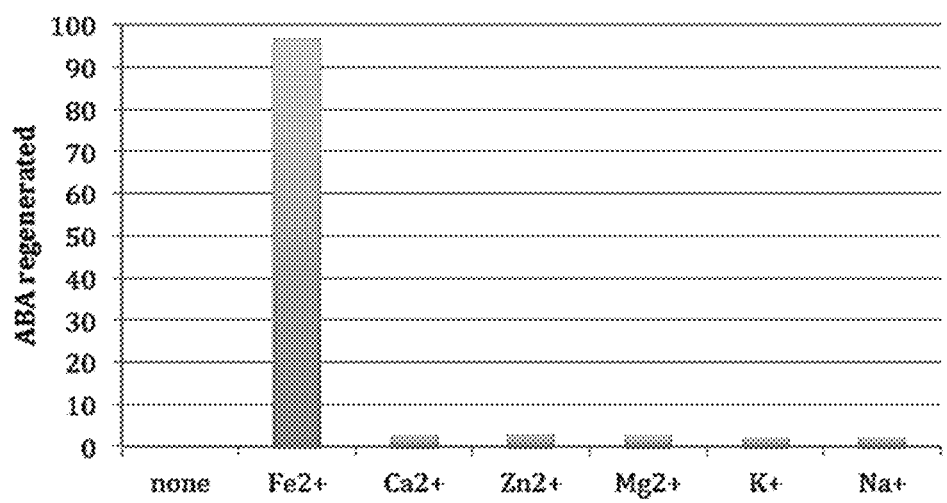

FIG. 37. Data characterizing the ABA-based $Fe^{2+}$ sensing compounds shown in FIG. 36. (A) stability date; (B) reactivity data; (C) reactivity of Compound 1 and Compound 4 (FIG. 36) toward varying concentrations of $Fe^{2+}$; (D) selectivity of Compound 1 (FIG. 36) for various metals.

Figure 38:
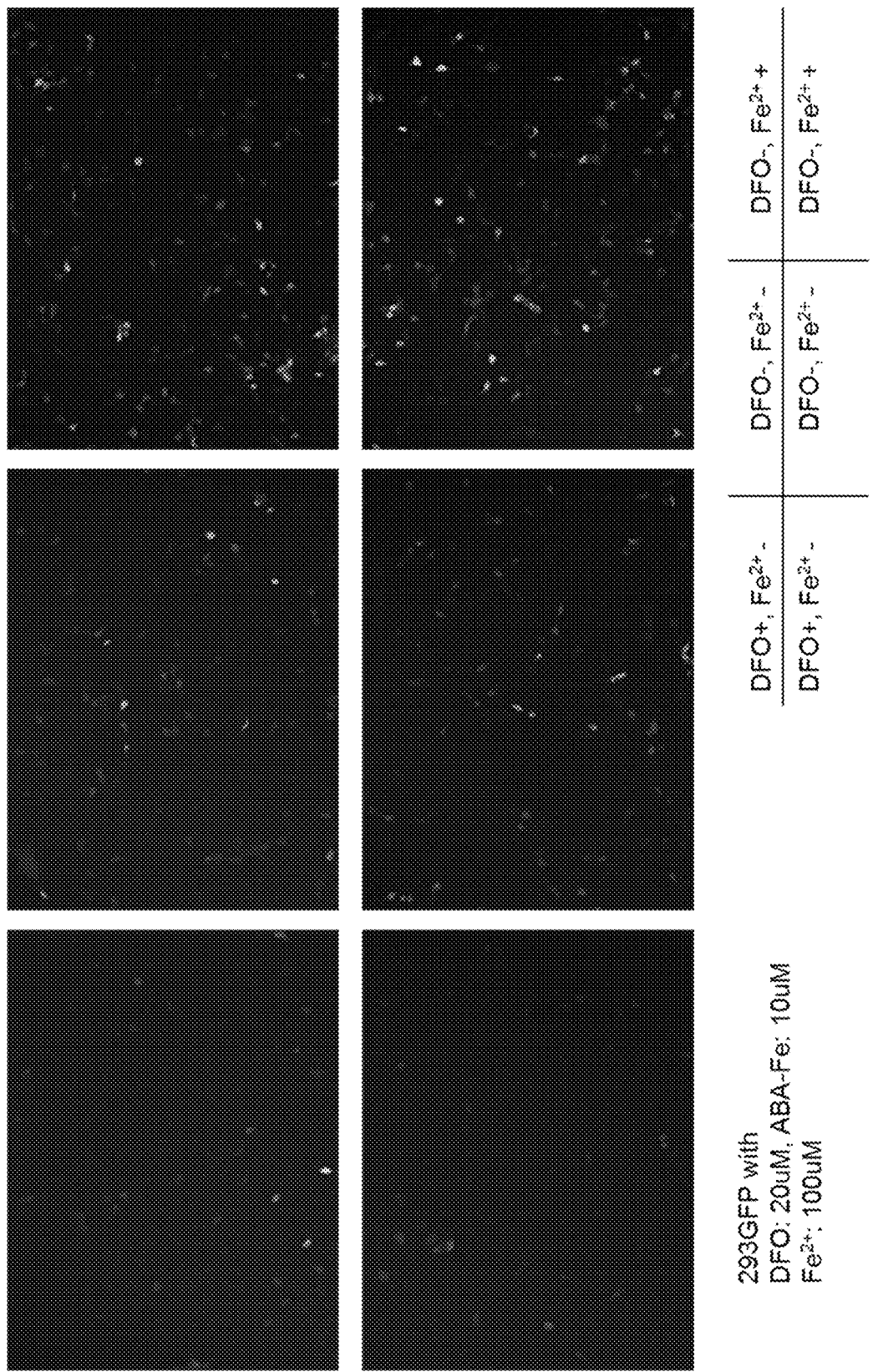

FIG. 38. Cell stability data for Compound 13 (FIG. 36).

Figure 39:
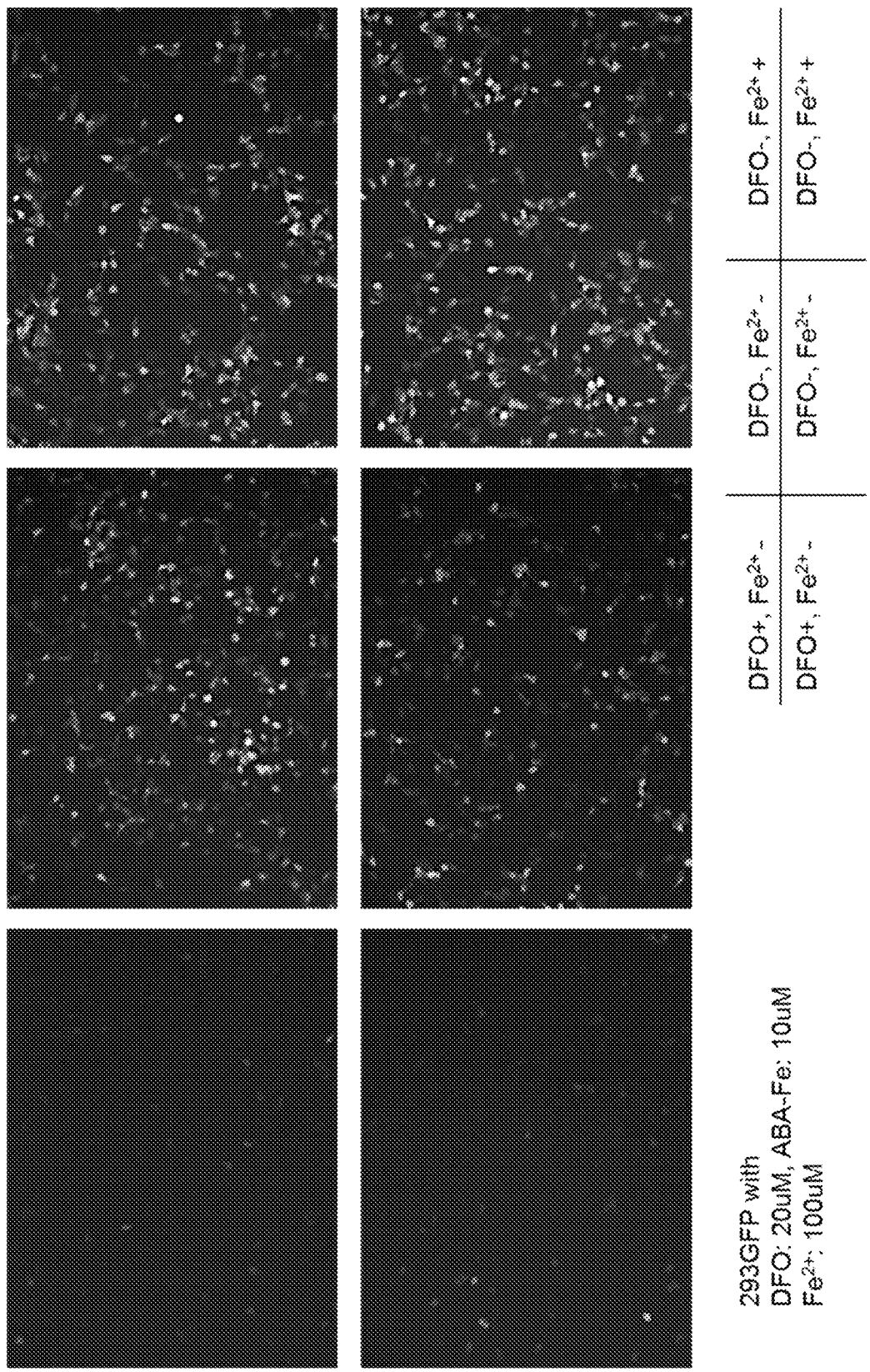

FIG. 39. Cell stability data for Compound 14 (FIG. 36).

Figure 40:
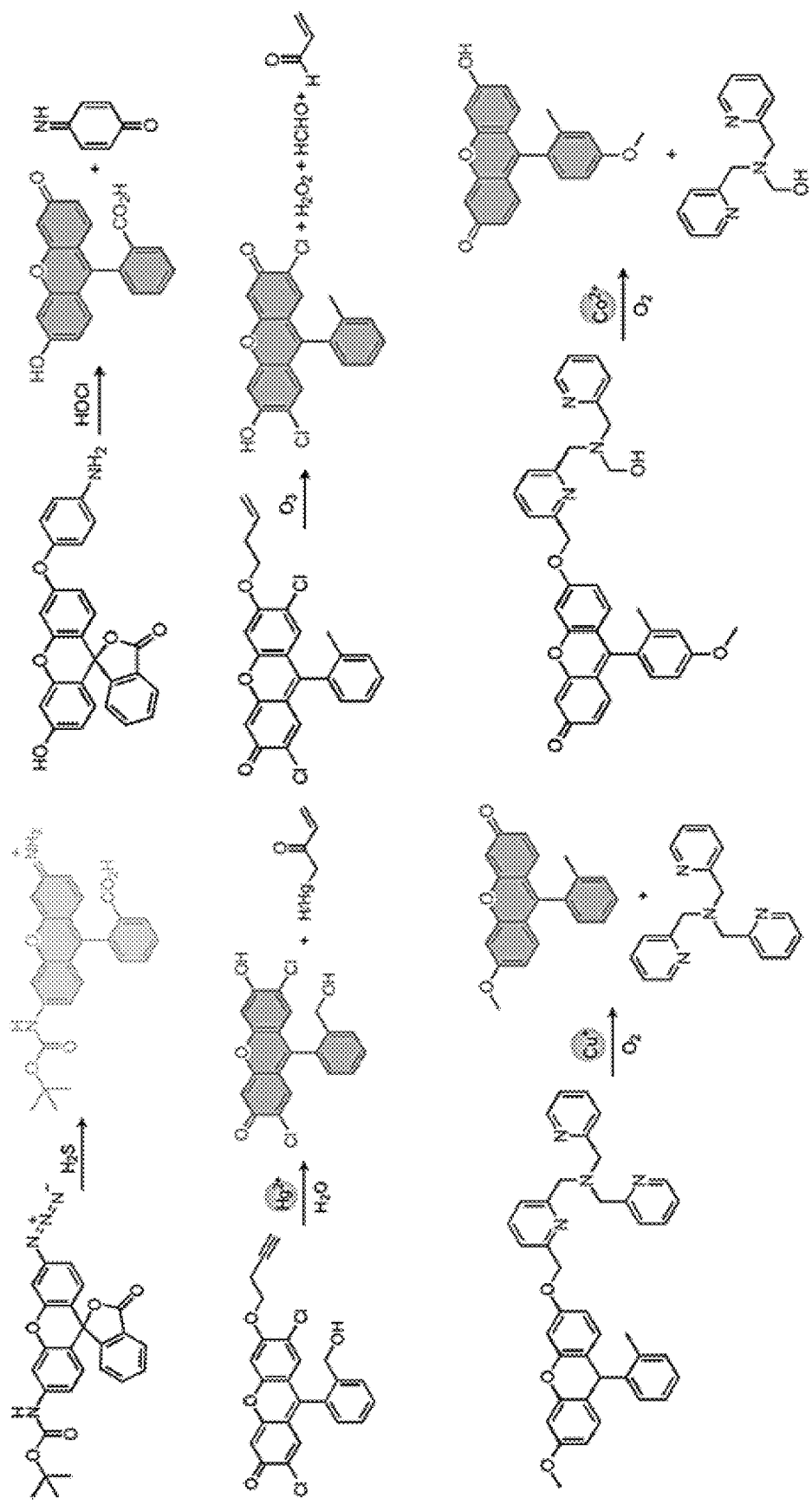

FIG. 40. Exemplary sensing probes for chemical stimuli $H_2S$, HOCl, $HG^{2+}$, $O_3$, $Cu^{2+}$, and $Co^{2+}$.

Figure 41:
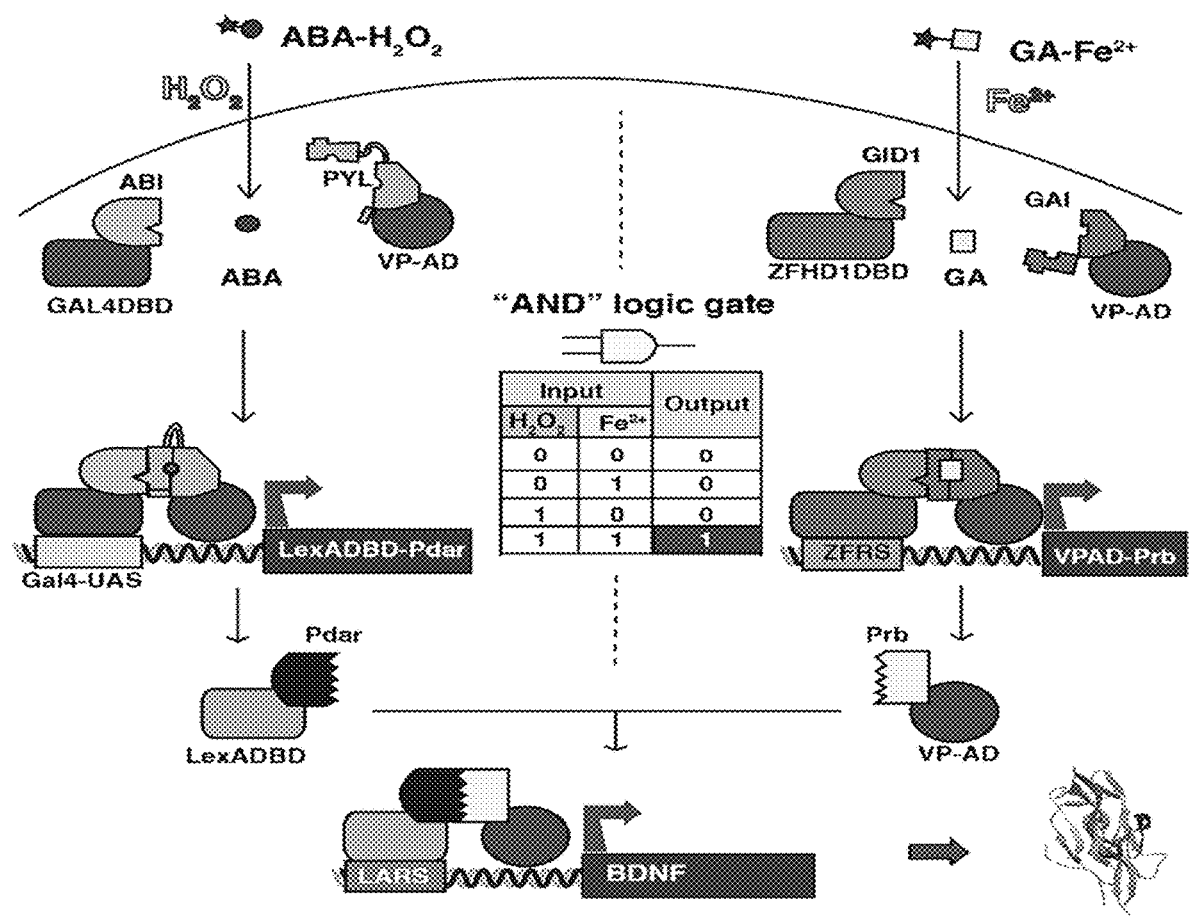

FIG. 41. A schematic diagram of a dual stimulus SIP system. Cellular activity output is generated only when both cellular stimuli, $H_2O_2$ and $Fe^{2+}$ are sensed by their respective SIP inducers, ABA-$H_2O_2$ and GA-$Fe^{2+}$, respectively.

DETAILED DESCRIPTION OF ILLUSTRATIVE EMBODIMENTS

Cells constantly sense their microenvironments and integrate perceived signals to generate proper cellular responses. Synthetic biology aims to engineer novel cellular functions by assembling molecular parts that enable a cell to detect and process specific signals to produce predictable and desired biological outputs. These efforts not only contribute to the understanding of how sophisticated cellular behaviors are built, but also can provide therapeutic applications.

This disclosure describes a novel chemical strategy, referred to herein as Stimulus-Induced Proximity (SIP), that enables a cellular signal (i.e., $H_2O_2$) to control chosen cellular events in mammalian cells. This strategy combines reactivity-based small molecule sensing with the chemical-induced proximity (CIP) technology and can control transcription, protein translocation, and/or membrane ruffle formation by $H_2O_2$. This new strategy can be a useful tool for synthetic biologists and ultimately can be applicable to the development of gene and cell therapies.

CIP technology has been developed to regulate various biological processes using exogenous chemical inducers. A chemical-induced proximity inducer can dimerize two unique inducer-binding adaptor proteins that are fused individually to two other proteins of interest. Depending on the choice of proteins of interest, different downstream biological events can be controlled by the exogenous chemical-induced proximity inducers. The modular nature of the chemical-induced proximity technology provides generality in design and diversity in application by being compatible for use with various target proteins of interest. These characteristics of the chemical-induced proximity technology allow one to control the association of target proteins of interest and, therefore, place downstream processes under the control of a chemical-induced proximity system inducer. Several orthogonal chemical-induced proximity systems using different chemical inducers, including rapamycin, FK506, abscisic acid (ABA), gibberellic acid (GA) and other synthetic ligands, have been developed for broad biological and biomedical applications.

The ability to engineer novel signaling pathways that enable cells to perceive and respond to endogenous cellular signals and generate desired outcomes provides advantages over controlling biological events by artificial ligands. For example, cells can be equipped with the ability to differentiate diseased and healthy microenvironments in patients, and respond by producing therapeutic effects accordingly. Existing approaches to connecting upstream cellular signals to downstream biological outcomes mainly rely on natural or laboratory evolved nucleic acids or proteins, and consequently a great deal of effort is usually expended in the creation of new functions. In contrast, this disclosure describes a unique chemical strategy to achieve this goal by modifying the chemical-induced proximity (CIP) technology to be under the control of selected endogenous cellular signals.

We modified CIP technology because the CIP technology provides diversity and generality in controlling cellular processes. Other common small molecule-inducible systems (e.g., tetracycline-inducible or hormone-inducible systems) are typically limited to control of transcription. In contrast, the stimulus-induced proximity (SIP) technology described herein provides the diversity and generality typically associated with methods that involve chemical-induced proximity.

A SIP inducer is generated by chemically modifying a chemical-induced proximity inducer with a residue that abolishes the protein dimerizing activity of the inducer. The modified inducer remains inactive until being exposed to the chosen signal molecule, which promotes the chemical cleavage of the masking group. Having been thus regenerated, the original inducer is free to trigger the desired biological effects (FIG. 1a). This strategy takes advantage of the accumulated knowledge in the development of various chemical reactivity-based small molecule-sensing fluorescent probes aimed at detecting and reporting endogenous cellular signaling molecules such as, for example, $H_2O_2$, $H_2S$, NO, $O_3$, and certain metal ions.

One exemplary model embodiment involves modifying the plant abscisic acid (ABA) chemical-induced proximity system. As shown in FIG. 1a, ABA binds selectively to the $PYR_1$-like (PYL) protein to create a surface that can subsequently bind the ABI protein. Based on its crystal structure, ABA is imbedded within, and makes extensive contacts with, the PYL pocket. Thus, any chemical modification of ABA may disrupt its binding to PYL and therefore abolish the induced association between PYL and ABI. By modifying ABA with a group that can be removed by a particular SIP stimulus, the ABA-based chemical-induced proximity activity can be controlled by the SIP stimulus. The carboxylic acid group on ABA, which is involved in hydrogen bonding to PYL, provides a target domain for attaching a masking group.

Figure 4:
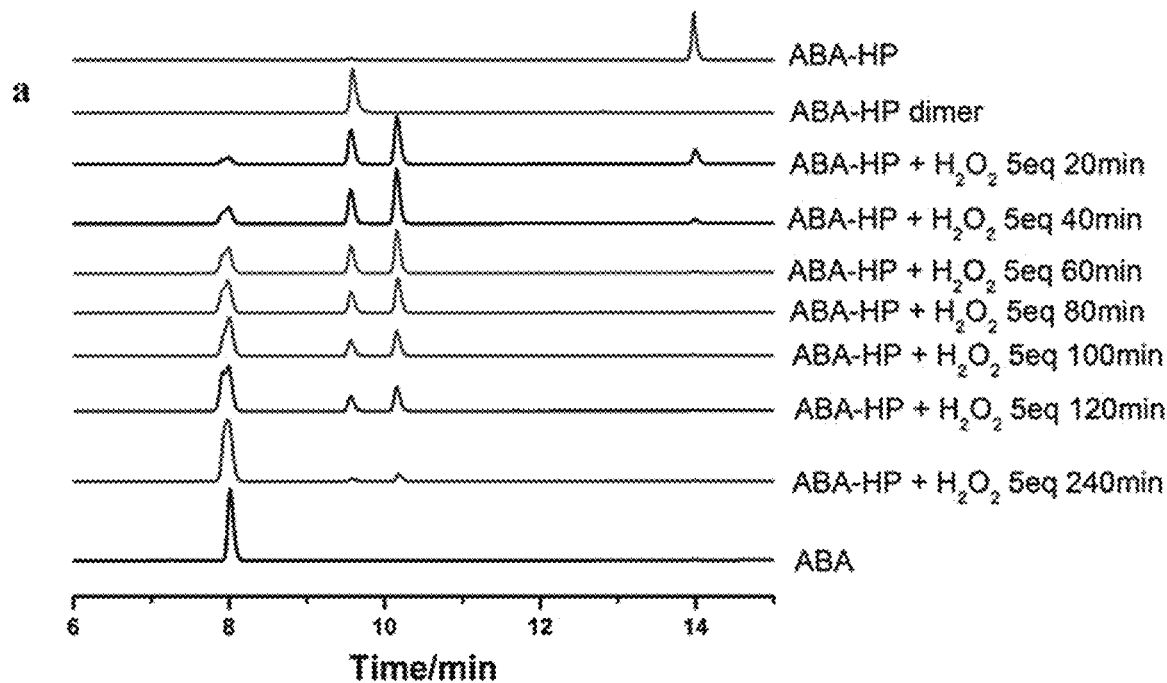
FIG. 4. Time dependent cleavage of ABA-HP by $H_2O_2$ detected by HPLC. 1 mM ABA-HP was treated with 5 mM $H_2O_2$ in 50% HEPES/DMSO (10 mM HEPES, pH 7.4) from 0 to 240 min at 37° C. ABA-HP dimer (characterized by mass spectrometry, FIG. 13) was generated by incubation at 37° C. in 50% HEPES/DMSO for two hours and kept stable 24 hours later. (a) Representative HPLC chromatograms from three independent experiments. (b) Quantitation of generated ABA from ABA-HP in the presence of $H_2O_2$. The results were quantified by integrating the peak area corresponding to the ABA peak over the total areas of all peaks to give the generated ABA %. The shown result was the average from three independent experiments.
Figure 4:
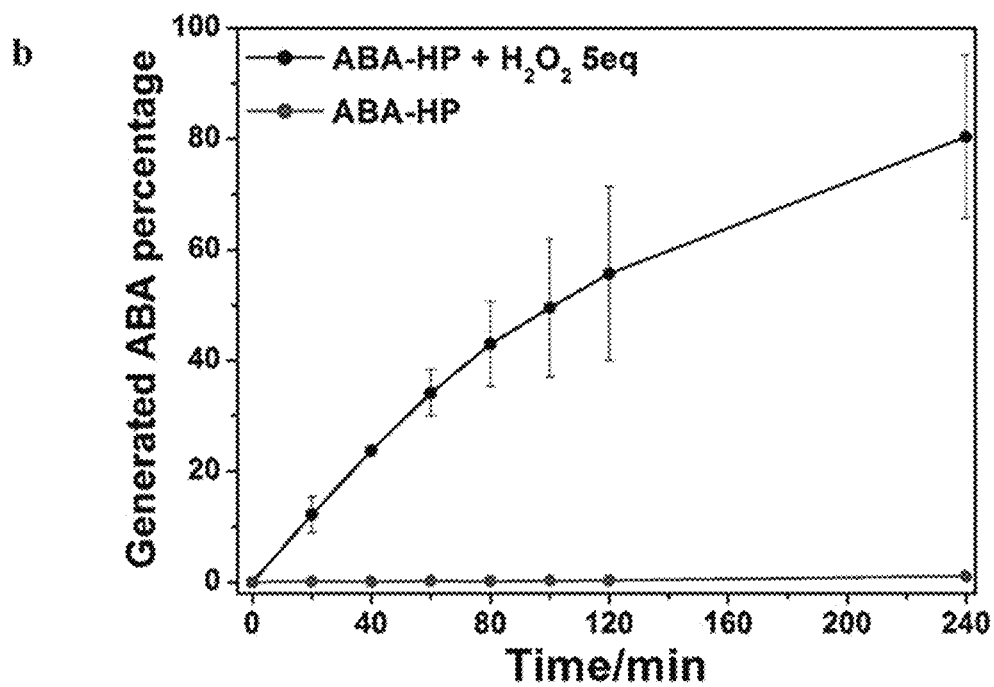
Figure 5:
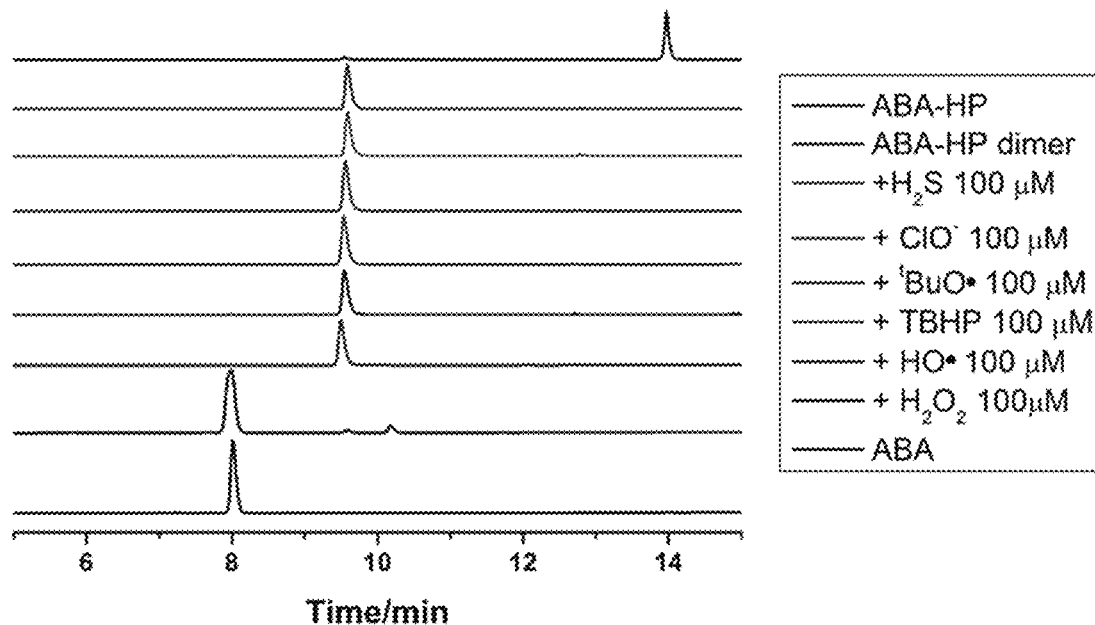
FIG. 5. Reaction selectivity of ABA-HP (100 μM) against H2S and ROS (100 μM) in 50% HEPES/DMSO. The results were analyzed by HPLC after four-hour incubation at 37° C.

One exemplary embodiment involves an $H_2O_2$-inducible ABA-mediated chemical-induced proximity system. $H_2O_2$ is a reactive oxygen species, serves as an important secondary messenger, and is involved in several biological processes and diseases. To transform the ABA-inducible chemical-induced proximity system into an $H_2O_2$-inducible stimulus-induced proximity system, we synthesized an $H_2O_2$-responsive boronated ABA, designated as ABA-HP in FIG. 1b. ABA-HP can convert back to ABA upon exposure to $H_2O_2$. Monitored by HPLC, we observed that ABA-HP was stable in biological buffer at 37° C. throughout the 24-hour observation period (FIG. 1c). Upon the addition of $H_2O_2$ (5 eq), ABA-HP started to convert back to ABA within minutes and the transformation was completed in four hours (FIGS. 1c, 4a, and 4b). To test the selectivity of ABA-HP towards $H_2O_2$ relative to other reactive oxygen species, cellular metals, and/or signaling molecules, ABA-HP was incubated with different molecules, including $H_2O_2$, HO., tert-butylhydroperoxide (TBHP), tBuO., $ClO^-$, $H_2S$, or various metal ions for four hours and the products were analyzed by HPLC. ABA-HP was stable against all molecules tested at 100 μM (FIG. 1d, FIG. 5, and FIG. 6), except $Cu^+$ and $Cu^{2+}$, which produced a minimal amount of cleavage but were later shown to have no effects at the more physiologically relevant concentration of 10 μM (FIG. 7).

Figure 2:
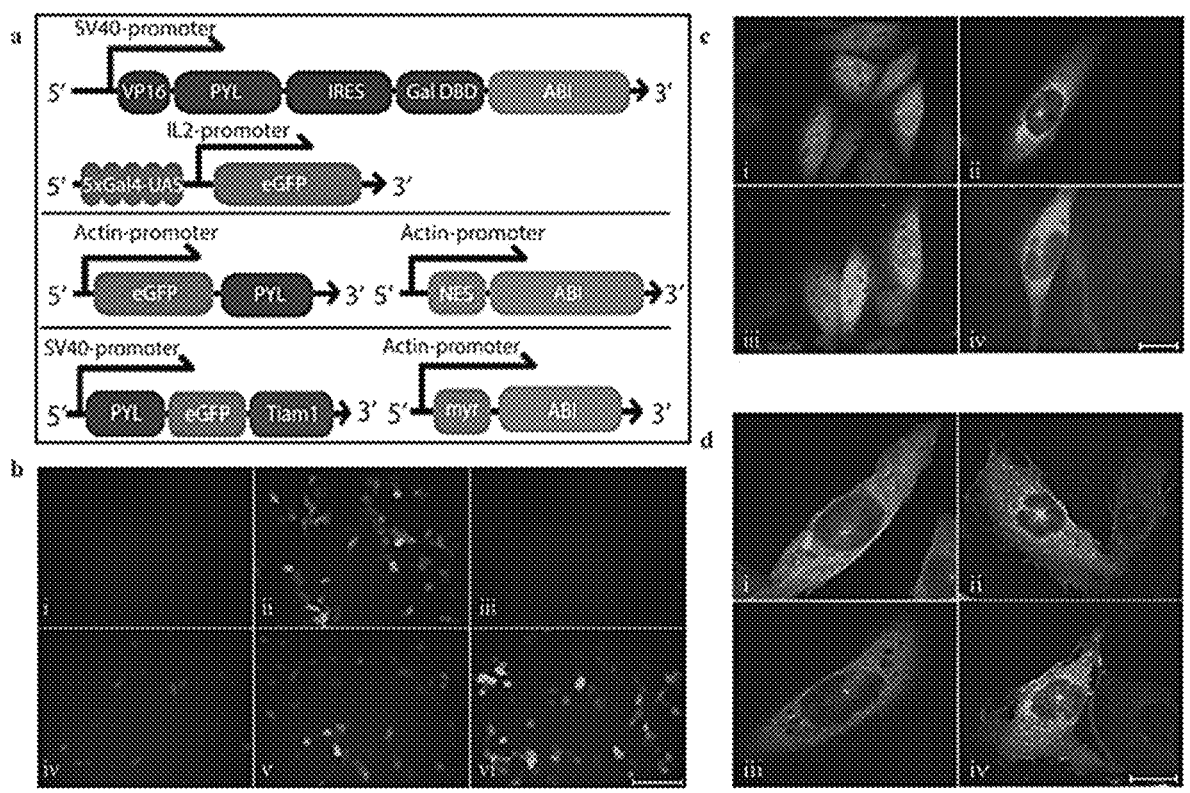
FIG. 2. (a) DNA constructs for $H_2O_2$-induced ABA-mediated biological controls: (i) transcriptional control, (ii) nuclear exporting, (iii) ruffle formation. (b) EGFP expression in CHO cells (10 h): (i) no drug; (ii) ABA 10 μM; (iii) ABA-HP 10 μM; (iv) ABA-HP 10 μM+$H_2O_2$ 10 μM; (v) ABA-HP 10 μM+$H_2O_2$ 50 μM; (vi) ABA-HP 10 μM+$H_2O_2$ 100 μM. (c) Nuclear exporting of eGFP in CHO cells (30 min): (i) no drug; (ii) ABA 10 μM; (iii) ABA-HP 10 μM; (iv) ABA-HP 10 μM+$H_2O_2$ 100 μM. (d) Ruffle formation of CHO cells (30 min): (i) no drug; (ii) ABA 10 μM; (iii) ABA-HP 10 μM; (iv) ABA-HP 10 μM+$H_2O_2$ 100 μM. Scale bar is 100 μm for (b) and 20 μm for (c) & (d). Images shown are representative from three independent experiments.

To determine if the ABA generated from the $H_2O_2$-induced cleavage of ABA-HP is biologically active, we tested whether it could induce downstream biological processes. We first investigated $H_2O_2$-induced transcriptional activation using an HEK 293T stable cell line, in which enhanced GFP (eGFP) expression occurs only in the presence of functional ABA. The cell line was created with both the ABA-responsive split transcriptional activator DNA fragment (VP-PYL and GAL4DBD-ABI linked by IRES; Liang et al., 2011, *Sci. Signal.* 4, rs2) and an inducible eGFP DNA fragment (with 5×UAS) inserted into the genome (FIG. 2a). The in vivo $H_2O_2$ concentrations of normal or pathologic tissue samples varies from less than 10 µM to greater than 300 µM, with pathologic tissues typically exhibiting higher levels of $H_2O_2$.

We tested the response of our system to $H_2O_2$ at physiologically relevant concentrations under cell culture conditions. The eGFP reporter cells were treated with no drug, or 10 µM of ABA, ABA-HP, or ABA-HP exposed to $H_2O_2$ (1, 5 or 10 eq) for five to 24 hours. The expression of eGFP was monitored at specific time points using a fluorescence microscope. EGFP expression was not observed within a 10-hour period following the addition of ABA-HP alone (FIG. 2b). This result suggested that ABA-HP is stable within cells for at least 10 hours and thus cleavage at the ester linkage by cellular esterases is minimal. With extended incubation (24 hours), eGFP expression was indeed observed (FIG. 8), which indicates further structural modification of the boronic probe may be desirable for applications that involve extended incubation. Alternatively, for cellular experiments, cell culture media can be exchanged regularly with media containing fresh ABA-HP and thus restrict the build-up of esterase-cleaved ABA.

When either ABA or the combination of ABA-HP and $H_2O_2$ were added, eGFP expression could be observed after five hours (FIG. 2b and FIG. 8), which is evidence for the $H_2O_2$-induced cleavage of ABA-HP to generate functional ABA in situ. Varying levels of eGFP production were evident when different amounts of $H_2O_2$ were added (FIG. 2b). Different levels of $H_2O_2$ reproduced differential levels of ABA and resulted in a dose-dependent eGFP expression. This property can be useful for converting different levels of cellular signals (e.g. $H_2O_2$) into different levels of transcriptional activity or for developing a ratiometric protein-based cellular $H_2O_2$-reporting system.

Various cellular events are regulated by the dynamic sub-cellular translocation of proteins. To test if protein translocation can be controlled by $H_2O_2$, we used a known ABA-inducible eGFP nuclear exporting system consisting of NES-ABI and PYL-eGFP DNA constructs (FIG. 2a; Liang et al., 2011, Sci. Signal. 4, rs2). CHO cells were transfected with both plasmids for 24 hours and then incubated without additive, or with 10 µM of ABA, ABA-HP, or ABA-HP plus 10 eq of $H_2O_2$ for one hour. The sub-cellular location of PYL-eGFP fusion protein was observed with a fluorescence microscope. PYL-eGFP showed pan-cellular distribution in the absence of ABA and was localized out of the nucleus when ABA was added (FIG. 2c). ABA-HP alone did not change the sub-cellular location of eGFP-PYL. However, the addition of ABA-HP plus $H_2O_2$ caused rapid nuclear export (FIG. 2c). This result expanded the scope of $H_2O_2$-controlled processes beyond transcription, thus beyond that achieved by other inducible systems.

To further investigate whether a complex biological process can be triggered by $H_2O_2$-induced protein dimerization, we examined the membrane ruffle formation resulting from localized Rho GTPase activation. Tiam1 is a guanine exchange factor for Rac, a member of Rho GTPase. The membrane translocation of Tiam1 activated Rac signaling pathway and induced ruffle formation, which is involved in cell migration and morphogenesis. We constructed an ABA-inducible Tiam1 membrane localization system, which consists of DNA plasmids encoding the membrane-localized ABI (myr-ABI; Liang et al., 2011, Sci. Signal. 4, rs2) and the cytoplasmic eGFP/PYL-fused Tiam1 (PYL-eGFP-Tiam1) (FIG. 2a). CHO cells were transfected with these plasmids for 24 hours and then incubated for one hour without additive, or with 10 µM of ABA, ABA-HP or ABA-HP plus 10 eq of $H_2O_2$. The ruffle formation in cells was analyzed by the confocal microscopy. Only cells treated with either ABA or the combination of ABA-HP and $H_2O_2$ showed obvious ruffle formation (FIG. 2d). This demonstrated that the feasibility and utility of stimulus-induced proximity to engineer a novel cell signaling pathway to translate a cellular stimulus or signal (e.g. $H_2O_2$) into a complex cellular event (e.g., ruffle formation) that is not normally associated with this signal.

Figure 3:
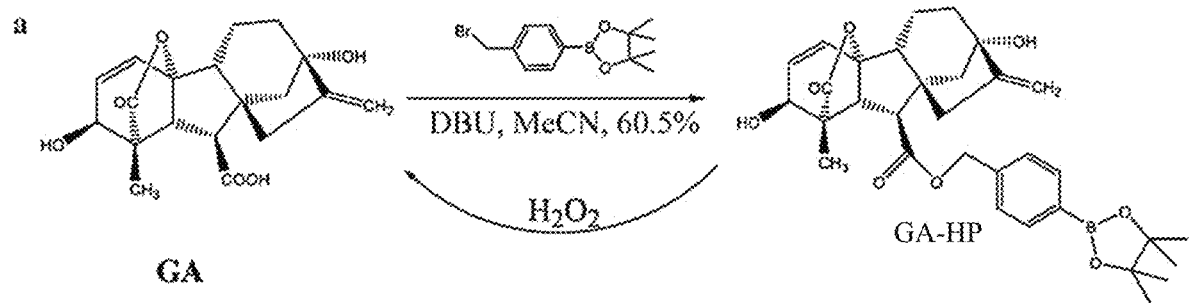
FIG. 3. (a) Synthesis of GA-HP and its conversion to GA in the presence of $H_2O_2$. (b) 5 mM GA-HP was treated with or without 10 eq of $H_2O_2$ in 50% HEPES/DMSO for different time at 37° C. and analyzed by HPLC. (c) DNA constructs used for $H_2O_2$-induced GA-mediated nuclear exporting of eGFP. (d) Nuclear exporting of eGFP in CHO cells (30 min): (i) no drug; (ii) GA-AM 10 μM; (iii) GA-$H_2O_2$ 10 μM; (iv) GA-$H_2O_2$10 μM+$H_2O_2$ 100 μM. Scale bar is 20 μm for (d). Images shown are representative from three independent experiments.
Figure 3:
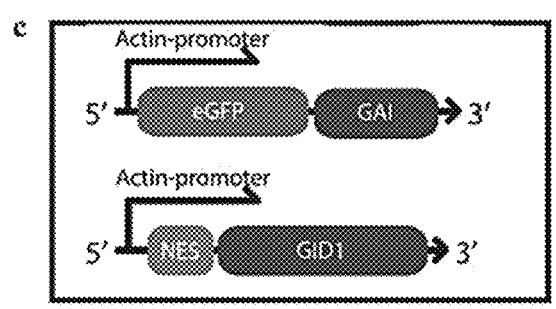
Figure 3:
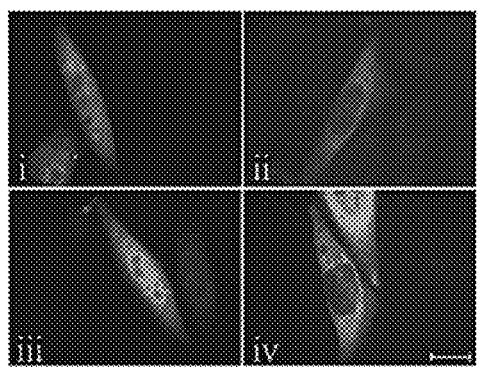
Figure 3B:
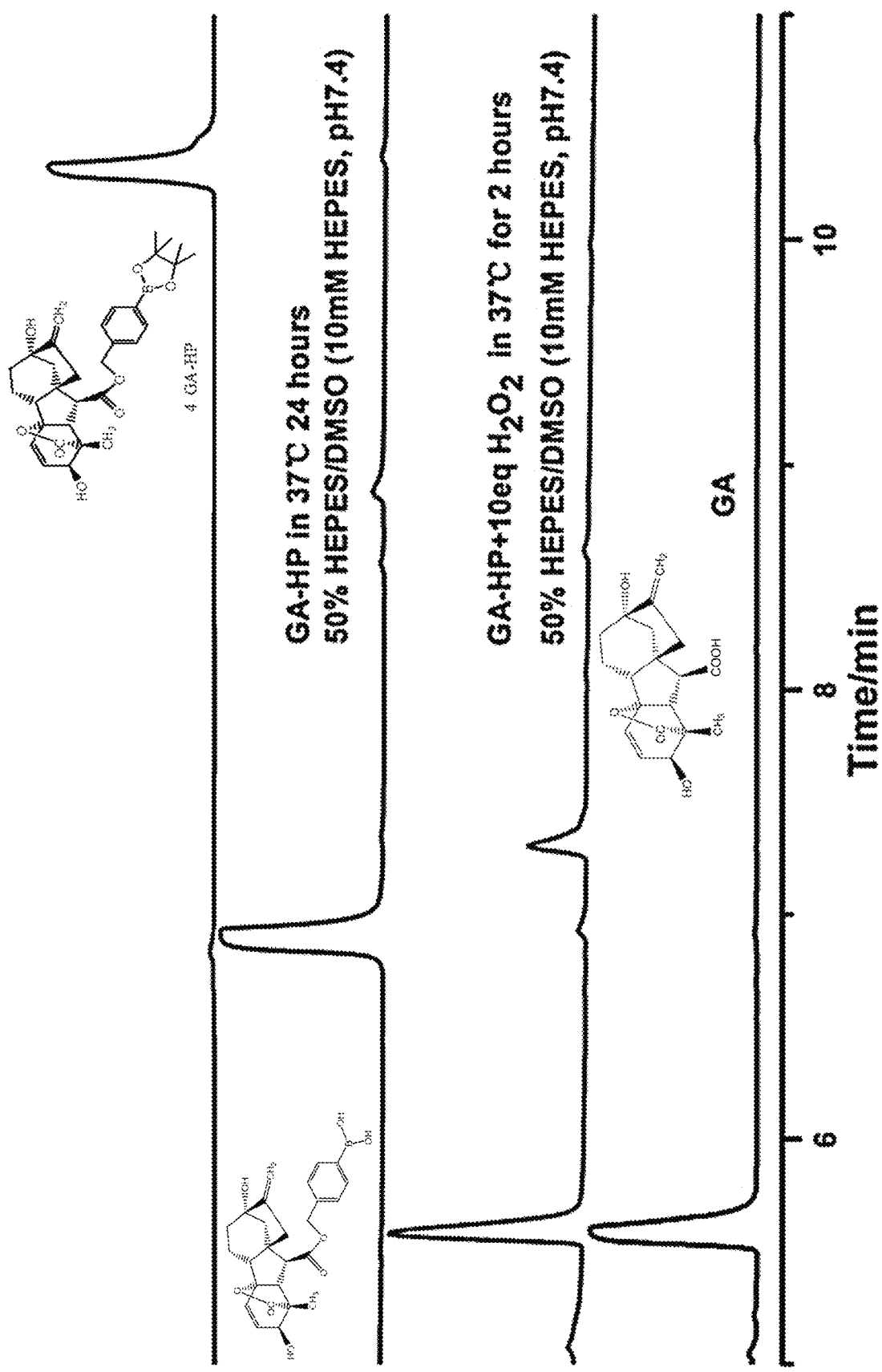

The same strategy can be applied to other chemical-induced proximity inducers such as, for example, gibberellin (gibberellic acid, GA). GA induces binding between GAI and GID1 proteins similar to the way in which ABA induced binding between PYL and ABA. GA is not cell permeable and has therefore been modified as the acetoxymethoxy ester (GA-AM) to cross the cell membrane and subsequently be cleaved by the esterase to regenerate GA. A carboxylate group on GA is involved in its native biological function, but a minor modification that converts the carboxylate into a nonhydrolyzable hydroxamate abolishes the native chemical-induced proximity activity of GA. Thus, modifying the carboxylate with the $H_2O_2$-sensitive boronic probe can render the resulting compound, GA-HP, inactive for chemical-induced proximity until GA is regenerated by exposure to $H_2O_2$. We synthesized GA-HP by coupling the boronic group to GA (FIG. 3a). We tested the chemical stability of GA-HP, and its conversion back to GA upon $H_2O_2$ addition, using HPLC (FIG. 3b and FIG. 9). GA-HP did not release GA when incubated in biological buffer for 24 hours even though the boronic group itself was partially hydrolyzed to give an inert product. GA was rapidly regenerated upon adding $H_2O_2$ (10 eq), and the conversion was completed in two hours.

To examine whether the regenerated GA is functional within the cell, we made DNA constructs to encode a nuclear exported GID1 (NES-GID1) and a pan-cellular eGFP-tagged GAI (eGFP-GAI) (FIG. 3c). CHO cells were transfected with these plasmids for 24 hours and then incubated for one hour without additive or with 10 µM of GA-AM, GA-HP or GA-HP plus 10 eq of $H_2O_2$ for one hour. The sub-cellular location of the PYL-eGFP protein was observed with a fluorescence microscope (FIG. 3d). Only cells treated with either GA-AM or the combination of GA-HP and $H_2O_2$, showed nuclear exportation, which indicated that the functional GA was regenerated upon $H_2O_2$ addition. Given that GA cannot cross the cell membrane, the observed intracellular effects suggested that the $H_2O_2$-induced cleavage of GA-HP occurred inside the cells. The successful implementation of this chemical-induced proximity modifying strategy with GA demonstrates the potential generality of this method.

The while occasionally described herein in the context of an exemplary embodiment in which inducer molecule is ABA, the methods described herein can be practiced using any suitable inducer molecule. Exemplary alternative inducer compounds include, for example, any compound that can dimerize proteins. Such compounds include, for example, rapamycin, auxins, FK506, or a protein dimerizing analog or derivative thereof.

The ABA-based dimerization system has many features, including rapid response kinetics, fast rate of reversibility, wide dose responsive range, no known toxicity issues and excellent bioavailability. Moreover, ABA and rapamycin systems are orthogonal and can be used simultaneously to control two independent cellular events. In an alternative exemplary application, one can use a light-inducible ABA-based CID system using a photocaged ABA that enables dose-dependent photo-control of cellular processes (FIG. 19).

As discussed above, ABA binds with the PYL protein to form a complex that subsequently recognizes ABI. Structural modifications of ABA, especially those that involve incorporating bulky groups, may disrupt its binding to PYL and, therefore, inhibit its ability to promote subsequent PYL-ABI dimerization. Consequently, incorporating a photo-removable group can result in an ABA derivative that would be incapable of binding to PYL. Furthermore, the carboxylic acid moiety in ABA, which forms hydrogen bonds with PYL, can be a site to which a chosen photo-removable group can be attached.

Figure 20A:
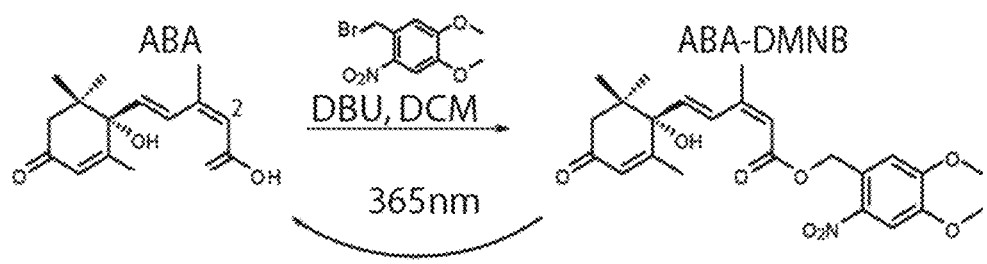
Figure 20B:
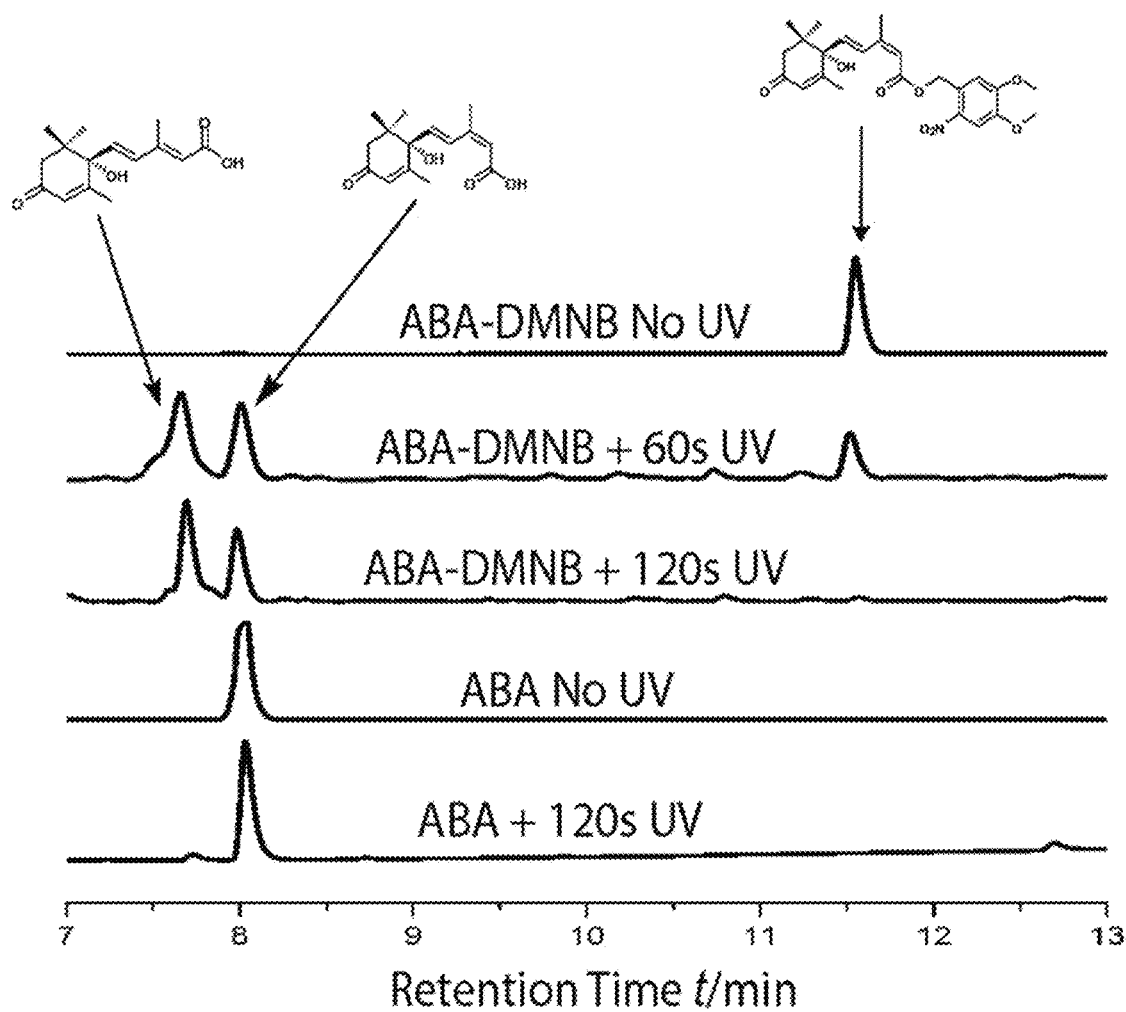

4,5-Dimethoxy-2-nitrobenzyl (DMNB) and other nitrobenzene groups have been used to cage small molecules because they can be removed by 365 nm light. In one exemplary embodiments, a light-inducible system can involve an ABA derivative, ABA-DMNB, that includes a DMNB ester group (FIG. 20A). HPLC analysis shows that ABA-DMNB is stable at 37° C. in biological buffer in the dark for 24 hours (FIG. 26). To examine the efficiency of the photo-uncaging process, solutions of ABA-DMNB (10 µM and 100 µM) were irradiated with 365 nm UV light emitted from a fluorescent microscope. HPLC analysis of the photolysate showed that the ABA-DMNB was cleaved to regenerate free ABA following irradiation for 120 seconds (FIG. 20B and FIG. 27). In addition to the ABA product, an additional product was generated at the same time in near equal amount during the photochemical process (FIG. 20B). We purified the by-product by HPLC and confirmed by mass spectrometry analysis that the by-product was indeed an ABA isomer, and the NMR data revealed the by-product to be the 2-trans isomer of ABA. Surprisingly, when uncaged ABA was subjected to the same photo-cleavage condition very little 2-trans isomer was produced, which suggests that the DMNB group may serve as a photosensitizing group to facilitate the isomerization of the ABA backbone under the applied irradiation condition (FIG. 20B).

The dimethoxynitrosobenzaldehyde released from the uncaging process of ABA-DMNB was not detected under the wavelength of 250 nm, which was used in the HPLC analysis. This is consistent with nitrosobenzene derivatives having low absorptivity at 250 nm. These results show that photo-uncaging of ABA-DMNB occurs rapidly to produce ABA in biologically relevant concentrations.

To confirm that the photo-regenerated ABA is biologically functional, we determined whether it can be employed to induce PYL-ABI dimerization in an ABA-inducible transcriptional activation system using an established HEK 293T inducible EGFP reporter cell line. The cell line was created with both the ABA-responsive split transcriptional activator DNA fragment (VP-PYL and GAL4DBD-ABI linked by IRES; Liang et al., 2011, *Sci. Signal.* 4, rs2) and an inducible EGFP DNA fragment (with 5×UAS and the IL-2 minimal promoter) inserted into the genome (FIG. 21A). EGFP expression was activated through the recruitment of VP16AD to the EGFP gene in the presence of ABA. 24 hours after plating the cells, 10 µM of ABA, pre-irradiated ABA-DMNB products, or non-irradiated ABA-DMNB were separately added to the cells and incubated for an additional eight hours. EGFP expression was then determined using a fluorescence microscopy. Both ABA and pre-photocleaved ABA-DMNB induced EGFP production (FIG. 21B), which indicate that the uncaging of ABA-DMNB gives biologically functional ABA. In contrast, 10 µM of non-irradiated ABA-DMNB did not induce EGFP expression (FIG. 21B). Thus, ABA-DMNB would be stable in cells under the experimental condition and unable to induce PYL-ABI dimerization in the absence of light.

The cellular stability of ABA-DMNB was explored further using a more sensitive and quantitative luciferase assay system, which employs an inducible luciferase construct (FIG. 21A). CHO cells were transfected with the ABA-inducible luciferase constructs for 24 hours and then 10 µM of ABA-DMNB was added and incubated in dark for 12 or 24 hours. Cells were then harvested and analyzed by using the luciferase assay. The results showed that very little luciferase expression took place after a 12-hour incubation period (FIG. 21C), an observation that is consistent ABA-DMNB not activating dimerization. Furthermore, only a minimal level of luciferase was induced following a 24-hour incubation, which demonstrates that ABA-DMNB is relatively stable under the cell culture condition despite possessing an ester that could potentially be hydrolyzed.

From the HPLC analysis of the ABA-DMNB photocleavage (FIG. 20B), a near equal amount of 2-trans ABA isomer was formed during the uncaging process. The 2-trans isomer exhibits measurably lower biological activity than the cis isomer. Based on the crystal structures of the ABA-PYL complex, it may be that the 2-trans isomer may not fit the PYL pocket as well as the cis isomer, which may result in a lower dimerization efficiency and, therefore, decreased downstream activity. To confirm that the generated 2-trans ABA isomer would not interfere with the dimerization induced by the regenerated cis-ABA, we tested the induced expression of luciferase by the cis-ABA isomer, the 2-trans ABA isomer, or a mixture of the ABA isomers. In this experiment, CHO cells were transfected with the ABA-inducible luciferase constructs for 24 hours and then 10 µM of the stock cis-ABA, photo-regenerated cis-ABA, photo-regenerated trans ABA isomer, or a mixture of regenerated cis-ABA and regenerated trans-ABA (10 µM each) was added and incubated for an additional 24 hours. Cells were then harvested and subjected to the luciferase assay. The regenerated cis-ABA gave a similar activity as the stock ABA and the 2-trans isomer exhibited reduced activity (FIG. 28). The mixture of the cis and trans isomers induced luciferase expression comparable to the cis-ABA alone, suggesting that the trans isomer does not attenuate the effects of the cis-ABA.

The ABA-inducible luciferase assay also was used to determine if ABA-DMNB is effectively photo-cleaved in cell culture. Different quantities of ABA and ABA-DMNB (FIG. 21D) were independently added to transfected CHO cells. The cells that received ABA-DMNB were either kept in the dark or irradiated using 365 nm UV light for 120 seconds. Twelve hours after either ABA or ABA-DMNB was added and the cells were irradiated, cells were harvested and subjected to the luciferase assay. Cells that were treated with ABA or those with ABA-DMNB followed by irradiation induced luciferase expression (FIG. 21D). Similarly, the HEK 293T-inducible EGFP reporter cell line showed EGFP expression when cultures containing ABA-DMNB were irradiated (FIG. 29). Thus, ABA-DMNB can be uncaged in cell culture to allow light-induced controls of transcriptional activation in live cells.

ABA gives dose-dependent induction of gene expression and ABA generated by irradiation of ABA-DMNB also displays this property. Irradiation of transfected cells with the addition of increasing concentrations of ABA-DMNB leads to corresponding increases in the level of luciferase expression (FIG. 21D). A concern of using UV-triggered reactions in cells is phototoxicity. However, based on cell morphology and the growth rate, no obvious cytotoxicity was observed under the irradiation conditions used to cleave ABA-DMNB. Finally, the DMNB-derived photoproduct does not cause observable toxicity at the concentrations used in the experiments described above.

The ability to use light to control protein translocation through ABA-DMNB uncaging was evaluated next. Plasmids expressing EGFP-tagged PYL and nuclear export sequence (NES) peptide-linked ABI (FIG. 22A) were transfected into CHO cells. The transfected cells were then either treated or not treated with ABA, ABA-DMNB, or ABA-DMNB and irradiated for 60 seconds. Fluorescence microscopy analysis was used to determine subcellular locations of EGFP fusion proteins. Cells treated with ABA or with ABA-DMNB followed by UV irradiation showed markedly decreased intensities of EGFP in the nuclei within 15 minutes (FIGS. 22B and 22C). On the other hand, cells that were either not treated with ABA-DMNB or with ABA-DMNB but not subjected to UV irradiation showed EGFP distribution throughout the whole cells. Furthermore, the observed nuclear export of EGFP fusion protein can be readily reversed by washing away the uncaged ABA using fresh media. Thus, protein translocation can be induced by light through photo-uncaged ABA and can be readily reversed.

To examine the reversibility of the photo-induced EGFP nuclear exportation process, cells that were treated with ABA or ABA-DMNB followed by UV irradiation were washed with fresh culture media not containing drugs and subjected to fluorescence analysis. Induced nuclear exportation of EGFP was reversed following three washes (within 30 minutes) (FIG. 22B, 22C).

Next, we examined the induction of ruffle formation through the activation of the Rac1 signaling pathway in order to determine if the light-activated ABA system can be used to regulate a complex biological process. The GTP exchange factor, Tiam1, when presents at the cell membrane, activates Rac1 to initiate a signaling pathway that leads to cytoskeletal remodeling that forms filopodia and/or lamellipodia. To activate Rac1 signaling and induce membrane ruffling, light and ABA-DMNB were used to control membrane localization of Tiam1 (FIG. 23A). A construct encoding a membrane localized ABI (myr-ABI) and one expressing a constitutively active Tiam1 fused to EGFP and PYL were employed for this purpose (FIG. 23A). Following the transfection of CHO cells with both plasmids for 24 hours, 10 μM of ABA-DMNB was added and the treated cell culture was irradiated with 365 nm light from a fluorescent microscope. Cells were then fixed on slides and analyzed under a fluorescence microscope. Cells were categorized as non-ruffled if they did not have observable cytoskeletal remodeling or as having ruffles if they displayed distinct lamellipodia and filopodia (FIG. 23B). The cultures that received ABA or ABA-DMNB with irradiation showed a greater percentage of cells displaying ruffling compared to the cultures that were incubated with ABA-DMNB without irradiation or were given no drug (FIG. 23C). Some background ruffling when overexpressing constitutively active Tiam1 was observed even when no drug was added. These observations demonstrate that the strategy of combining light and a caged ABA can be employed to control cytoskeletal remodeling through the initiation of Rac1 signaling.

A confocal microscope is often used to achieve greater precision in light-induced processes and could be used to cleave caged ABA more precisely. However, a confocal microscope is commonly equipped with a 405 nm laser, which cannot efficiently uncage ABA-DMNB (FIG. 30). To prepare another caged ABA that can be cleaved by 405 nm light, we conjugated ABA to the [7-(diethylamino)coumarin-4-yl]methyl (DEACM) group to give ABA-DEACM (FIG. 24A). The design of ABA-DEACM demonstrates the flexibility of the small molecule caging system, in which different caging groups can be easily installed as needed by using simple chemical processes rather than lengthy protein engineering steps that are otherwise needed in existing protein-based methods. Studies of photo-cleavage of ABA-DEACM using a 405 nm LED revealed that ABA-DEACM can be cleaved rapidly to give ABA within a few minutes (FIG. 24B, FIG. 30). As observed in the case of ABA-DMNB uncaging, the isomerized ABA was also produced, which suggested that the addition of a caging group may in general sensitized and promoted the isomerization of ABA, although the mechanism is unclear. The absorptivity of the coumarin photo-cleavage product at the detection wavelength (250 nm) was measured and was shown to be low ($\varepsilon=0.23$), and the coumarin by-product was therefore not seen in the HPLC analysis. Moreover, ABA-DEACM cannot be cleaved efficiently by 365 nm light (FIG. 31), which is employed to activate the ABA-DMNB caging system. This observation suggests that DMNB and DEACM can potentially be utilized as orthogonal caging groups on orthogonal CID inducers to independently control two cellular events.

An evaluation of the stability of ABA-DEACM using HPLC and the luciferase assay showed that it is stable chemically and in cell culture (FIG. 32 and FIG. 33). Photo-uncaged ABA-DEACM also showed the ability to induce EGFP-PYL nuclear export (FIG. 34) and Rac1 signaling activation/ruffle formation in cells (FIG. 35). To test the uncaging process in live cell experiments, EGFP nuclear export experiments were carried out by transfecting CHO cells with EGFP-PYL and NES-ABI constructs. The cells were then either treated with 10 μM ABA-DEACM and with or without 405 nm light irradiation under a confocal microscope, or with no drug but irradiated. The subcellular location of EGFP was followed for 20 minutes after irradiation. The nuclear export of EGFP fusion proteins was observed within a few minutes when treated with ABA-DEACM followed by irradiation, but not in the cases of no drug or no irradiation (FIG. 24C, 24D). We also tested the use of ABA-DEACM in live cell imaging to induce cell morphology changes. We transfected CHO cells in a culture chamber with myr-ABI and EGFP-PYLTiam1 constructs. Cells that were irradiated in the absence of ABA-DEACM did not show any cytoskeletal remodeling (FIG. 25A). On the other hand, cells that were incubated with ABA-DEACM and irradiated showed formation of filopodia and lamellipodia within 15 minutes (FIG. 25A, 25B). These results demonstrate that the local uncaging of ABA-DEACM produced a sufficient level of ABA, which rapidly dimerized PYL-fusion and ABI-fusion proteins before diffused away, to illicit desired biological responses.

Another exemplary embodiment involves an iron-responsive inducible system. To establish an $Fe^{2+}$-responsive gene inducible system, we developed a fluorescent $Fe^{2+}$-sensing unit that can be used to cage an inducer. The $Fe^{2+}$-sensor links an N-aryl-hydroxylamine moiety to a naphthalimide fluorophore. This $Fe^{2+}$-sensing unit is selectively responsive to $Fe^{2+}$ but is not responsive to other cell signals. This sensor can be used to report the endogenous labile $Fe^{2+}$ in, for example, astrocytes and in ischemic rat brain tissue samples.

Various N-phenyl-hydroxylamine moieties with different substitutions on the benzene ring were synthesized and are shown in FIG. 36. Exemplary benzene ring substitutions that can tune the reactivity towards $Fe^{2+}$ include, for example, p-$NO_2$, m-$NO_2$, o-$NO_2$, p-CN, p-Ac, o-Cl, o-I, or o-Me. HPLC analysis following iron-mediated cleavage in vitro revealed that, generally, substitutions that include an electron-withdrawing group facilitate cleavage while substitutions that include an electron-donating group increase the stability of the caged ABA against $Fe^{2+}$ (FIG. 37B). The differential electron-withdrawing/donating character and the position of each group can affect cleavage efficiency and/or the chemical stability of the caged compounds (FIG. 37A, FIG. 37C). Representative caged ABAs were selective for iron among other common abundant metals in cells (FIG. 37D). The caged ABAs also showed selectivity towards $Fe^{2+}$ vs $Fe^{3+}$ (FIG. 37B). One can include both an electron-withdrawing substitution and an electron-donating substitution on the same molecule at different positions to fine-tune the reactivity and selectivity.

Stability of the $Fe^{2+}$-sensing unit can be increased by increasing the steric hindrance near the ester in the $Fe^{2+}$-sensing unit to block esterase activity that can prematurely degrade the sensing unit. The o-Me substitution (FIG. 36, Compound 8) is stable in cells. Additional bulky groups can be installed to further increase the stability of the compound in cells. Moreover, one or more electron-withdrawing and/or electron-donating groups can be installed on the benzene ring to modulate the reactivity towards $Fe^{2+}$. For example, Compound 8 in FIG. 36 is chemically stable, exhibits $Fe^{2+}$ reactivity, and exhibits selectivity (FIG. 37A, FIG. 37B). Thus, this compound can be a suitable molecular scaffold to further develop alternative iron-sensing inducers.

Thus, this disclosure describes various exemplary embodiments of a stimulus-induced proximity strategy that can be customized to control different downstream cellular events. Stimulus-induced proximity inducers can be easily generated and respond to various stimuli (e.g., $H_2O_2$, light, and $Fe^{2+}$) rapidly and specifically at physiologically relevant concentrations. In various applications, a sensing unit for an endogenous cellular signaling molecule can be linked to ABA, GA, or another suitable chemical-induced proximity inducer to tailor their responding specificity toward a selected signal.

As discussed above, while certain exemplary embodiments have been described in detail in the context of a stimulus-induced proximity system in which the inducer includes abscisic acid (ABA) or gibberellic acid (GA), a stimulus-induced proximity system can be designed having an inducer that includes any polypeptide capable of heterodimerizing or homodimerizing a protein or proteins of interest. Accordingly, a stimulus-induced proximity system can include, as an inducer, an auxin, rapamycin, FK506, FK1012, cyclosporin A, coumermycin A1, methotrexate-SLF conjugate, trimethoprim-SLF conjugate, fusicoccin, or a protein dimerizing analog or derivative of any of the foregoing. As used herein, "SLF" refers to synthetic ligand for FKBP (FK506 binding protein).

Also, while certain exemplary embodiments have been described in detail in the context of a stimulus-induced proximity system in which the stimulus includes $H_2O_2$, $Fe^{2+}$, or light, the stimulus may be any chemical or physical stimulus for which a suitable sensing probe exists. Thus, alternative exemplary stimuli include, for example, $H_2S$, NO (or other cellular secondary messengers) HOCl, HOBr, $O_3$ (or other reactive oxygen species (ROSs)), $Hg^{2+}$, $Cu^+$, $Co^{2+}$, $Ca^{2+}$, $Zn^{2+}$ (or other cellular or environmental metal ions), or various proteases. The presence of the stimulus, whether chemical or physical, can induce bond cleavage that unmasks the inducer, producing the designed cellular activity. Exemplary sensing probes for $H_2S$ (Lippert et al., 2001, J. Am. Chem. Soc. 133:10078-10080; Peng et al., 2011, Angew. Chem. Int. Eng. 50:9672-9675; Xuan et al., 2012, Angew. Chem. Int. Eng. 51:2282-2284; Liu et al., 2011, Angew. Chem. Int. Eng. 50:10327-10329), HOCl (Setsukinai et al., 2003, J. Biol. Chem. 278:3170-3175), $O_3$ (Garner et al., 2009, Nat. Chem. 1:316-321), $Hg^{2+}$ (Song et al. 2008, J. Am. Chem. Soc. 130:16460-16461; Ando et al., 2011, J. Am. Chem. Soc. 133:2556-2566), $Cu^+$ (Taki et al., 2010, J. Am. Chem. Soc. 132:5938-5939), and $Co^{2+}$ (Au-Yeng et al., 2012, Chem. Commun. 48:5268-5270) are illustrated in FIG. 40. Exemplary sensing probes for various proteases are set forth in Table 1. Sensing activity can be tuned by chemically modifying the probing units to meet the targeted cellular signal concentrations.

TABLE 1

Caged ABA-based inducer compounds for proteases

| Protease | Constructs (SEQ ID NO:) | Drug | Disease |
|---|---|---|---|
| | Peptide-based prodrugs | | |
| Caspase-3 | Asp-Glu-Val-Asp-Pro-PABC-X (SEQ ID NO: 11) | DOX, | Cancer |
| | CAR-Lys-Gly-Ser-Gly-Asp-Val-Glu-Gly-X (SEQ ID NO: 12) | PH-A | |
| Cathepsin B | N-L-Leu-X (SEQ ID NO: 13) | DNR, DOX | Cancer, RA |
| CP | Arg-X, Ala-X, Asp-X (SEQ ID NO: 14) | MTX | Cancer |
| FAP | BHQ3-Lys-Gln-Glu-Gln-Asn-Pro-Gly-Ser-Thr-X (SEQ ID NO: 15) | PH-A | Cancer |
| Kallikrein 2 | Gly-Lys-Ala-Phe-Arg-Arg-X (SEQ ID NO: 16) | TPG | Cancer |
| MMP-2/-9/-14 | Glu-Pro-Cit-Gly-Hof-Tyr-Leu-X (SEQ ID NO: 17) | DOX | Cancer |
| MMP-7 | BHQ3-Lys-Arg-Ala-Leu-Gly-Leu-Pro-Gly-X (SEQ ID NO: 18) | PH-A | Cancer |
| | BHQ3-(D-Glu)$_8$-Arg-Pro-Leu-Ala-Leu-Trp-Arg-Ser-(D-Arg)$_8$-Lys-X (SEQ ID NO: 19) | | |
| Plasmin | D-Ala-Phe-Lys-X (SEQ ID NO: 20) | ara-C, | Cancer, RA |
| | D-Val-Leu-Lys-X (SEQ ID NO: 21) | AT-125, | |
| | D-Ala-Phe-Lys-(PABC)-X (SEQ ID NO: 22) | DOX, PM | |
| PSA | Mu-His-Ser-Ser-Lys-Leu-Gln-Leu-X (SEQ ID NO: 23) | DOX, | Cancer |
| | Mu-His-Ser-Ser-Lys-Leu-Gln-EDA-X (SEQ ID NO: 24) | 5-FudR, | |
| | 4-O-(Ac-Hyp-Ser-Ser-Chg-Gln-Ser-Ser-Pro)-X (SEQ ID NO: 25) | VNB, TPG, | |
| | HO$_2$C(CH$_2$)$_3$CO-Hyp-Ala-Ser-Chg-Ala-Ser-Leu-X (SEQ ID NO: 26) | L12ADT | |
| | N-gluaryl-(4-hydroxyprolyl)-Ala-Ser-chGly-Gln-Ser-Leu-X (SEQ ID NO: 27) | | |
| TOP | B-Ala-L-Leu-L-Ala-L-Leu-X (SEQ ID NO: 28) | DOX | Cancer |
| uPA | D-Ala-Phe-Lys-PABC-X (SEQ ID NO: 29) | DOX | Cancer |

TABLE 1 -continued

Caged ABA-based inducer compounds for proteases

| Protease | Constructs (SEQ ID NO:) | Drug | Disease |
|---|---|---|---|
| Macromolecular prodrugs | | | |
| Cathepsin B | PEG-L-Lys-X (SEQ ID NO: 30)<br>Poly-L-glutamic acid-X (SEQ ID NO: 31)<br>HPMAcp-Gly-Phe-Leu-Gly-X (SEQ ID NO: 32)<br>ALB-Lys-Lys-Phe-D-Ala-EMC-X (SEQ ID NO: 33)<br>ALB-EMC-D-Ala-Phe-Lys-Lys-X (SEQ ID NO: 34) | Ce6, DNR,<br>DOX, 5-FU,<br>MTX, PtD,<br>PTX,<br>SN-392,<br>TNP-470 | Cancer |
| Cathepsin K | HPMAcp-Gly-Gly-Pro-Nle-4AB-X (SEQ ID NO: 35) | ALN, PGE1 | Bone disease |
| MMP-2/-9 | DEX-Gly-Ile-Leu-Gly-Val-Pro-X (SEQ ID NO: 36)<br>ALB-Gly-Pro-Leu-Gly-Ile-Ala-Gly-Gln-X (SEQ ID NO: 37) | DOX, MTX | Cancer |
| Plasmin | ALB-EMC-D-Ala-Phe-Lys-Lys-X (SEQ ID NO: 38) | DOX | Cancer, RA |
| PSA | ALB-EMC-Arg-Arg-Ser-Ser-Tyr-Tyr-Ser-Gly-X (SEQ ID NO: 39)<br>HMPAcp-morpholinocarbonyl-Ser-Ser-Lys-Tyr-Gln-Leu-X (SEQ ID NO: 40) | DOX, TPG | Cancer |
| Thrombin | PEG-poly-L-Lys-X (SEQ ID NO: 41)<br>Poly-L-Lys-Gly-D-Phe-Pip-Arg-Ser-Gly-Gly-Gly-Gly-X (SEQ ID NO: 42) | Ce6, PH-A | Cancer, RA |
| Trypsin | Poly-L-Lys-X (SEQ ID NO: 43)<br>Poly-L-Lys-Gly-Ala-Ser-D-Arg-Phe-Thr-Gly-X (SEQ ID NO: 44) | PH-A | Cancer |
| uPA | ALB-EMC-Gly-Gly-Gly-Arg-Arg-X (SEQ ID NO: 45) | DOX | Cancer |
| Targeted prodrugs | | | |
| Cathepsin B | c1F6-Val-Cit-X (SEQ ID NO: 46)<br>cAC10-Val-Cit-X (SEQ ID NO: 47)<br>Pep42-Val-Cit-X (SEQ ID NO: 48)<br>GAL-HPMAcp-Gly-Phe-Leu-Gly-X (SEQ ID NO: 49) | DOX,<br>MMAE,<br>PTX | Cancer |
| Plasmin | RGD-4C-D-Ala-Phe-Lys-(PABC)-X (SEQ ID NO: 50) | MTX | Cancer, RA |

The sensing probe and inducer may be linked through a cleavable ester or amide linkage. The cellular stability of the linkages can be enhanced by chemically introducing a bulky substituent on the probes that can sterically interfere with access to the linkage.

The stimulus-induced proximity system described herein allows one to construct a novel cell signaling pathway by coupling a selected signal input to a chosen biological output. By networking these signaling pathways and applying desired computation algorithms (e.g., through Boolean logic gates), new cellular functions can be engineered to carry out sophisticated decision-making and to give proper biological outputs based on cellular microenvironments. FIG. 41 illustrates a more complex system in which a biological output occurs only after dual inputs—$H_2O_2$ and $Fe^{2+}$—are detected by the individual SIP sensor-inducer for each, ABA-$H_2O_2$ and GA-$Fe^{2+}$, respectively.

The stimulus-controlled systems described herein, whether controlled by a chemical stimulus based or a physical stimulus (e.g., light) can be used to regulate cellular processes such as, for example, transcription, protein translocation, signal transduction, and/or cytoskeletal remodeling. In particular, the light-controlled systems allow for dosage-dependent regulation and/or independently regulating multiple cellular events using light of different wavelengths. As a result, the strategy can be used to expand the repertoire of light-controlled methods that can be exploited to control and/or manipulate biological systems.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Chemical Synthesis.

Synthesis of compound 2: To 4-(bromomethyl)phenylboronic acid (200 mg, 0.93 mM, Sigma-Aldrich, St. Louis, Mo.) in 1 mL toluene was added pinacol (165 mg, 1.40 mM, Sigma-Aldrich, St. Louis, Mo.), then heated to reflux with Dean-Stark trap and stirred for three hours. The solvent was removed by rotavapor, and the product was purified through column chromatography and obtained as white solid (250 mg, 90.6%).

Synthesis of ABA-HP: To ABA (44 mg, 0.17 mM, Gold Biotechnology, Inc., St. Louis, Mo.) in 10 mL $CH_3CN$ was added compound 2 (55 mg, 0.19 mM) and DBU (55 µL, 0.37 mM, Sigma-Aldrich, St. Louis, Mo.), then stirred at room temperature for four hours. The solvent was removed by rotavapor, then the product was purified by column chromatography and obtained as white solid (50 mg, 62.5%).

Synthesis of GA-HP: To GA (100 mg, 0.29 mM, Alfa Aesar, Ward Hill, Mass.) in 20 mL $CH_3CN$ was added compound 2 (102.9 mg, 0.35 mM) and DBU (52 µL, 0.35 mM, Sigma-Aldrich, St. Louis, Mo.), then stirred at room temperature for four hours. The solvent was removed by rotavapor, and the product was purified by column chromatography, obtaining as white solid (97 mg, 60%).

Characterization data is shown in FIGS. 10-17.

Reverse-Phase HPLC Analysis.

Chemical stability and reactivity of ABA-HP towards $H_2O_2$: ABA-HP chemical stability: 1 mM ABA-HP (in DMSO) was incubated in 50% HEPES/DMSO (10 mM HEPES, pH 7.4) for 24 hours at 37° C. HPLC results were detected at 0 minutes, 20 minutes, 40 minutes, 60 minutes, 80 minutes, 100 minutes, 120 minutes, 240 minutes, and 24 hours. ABA-HP reactivity towards $H_2O_2$: 1 mM ABA-HP was incubated with 5 mM (5 eq) $H_2O_2$ in 50% HEPES/DMSO (10 mM HEPES, pH 7.4) at 37° C. HPLC results were detected at 0 minutes, 20 minutes, 40 minutes, 80 minutes, 100 minutes, 120 minutes, and 240 minutes (FIGS. 1c, 4a and 4b). 100 mM $H_2O_2$ was diluted with 11 µL of 30% (10 M) stock $H_2O_2$ (VWR) and 989 µL of $ddH_2O$. All showed concentrations were the final concentration. HPLC chromatograms were acquired using an ULTIMATE 3000 LC System (Thermo Fisher Scientific, Waltham, Mass.) with ACCLAIM 120 Å, C18, 3 µm analytical (4.6×100 mm) column (Thermo Fisher Scientific, Waltham, Mass.). Chromatographic conditions: eluent A: 0.1% v/v TFA in water; eluent B: 0.1% v/v TFA in acetonitrile. ABA in ethanol or ABA-HP in DMSO was eluted at a flow rate of 0.750 ml/min monitored at a wavelength of 260 nm. 0-12 min (linear): 95% A, 5% B to 5% A, 95% B; 12-15 min: 5% A, 95% B; 15-17 min (linear): 5% A, 95% B to 95% A, 5% B. Generation of ABA was quantified by the peak area of ABA out of the total peak area.

Reaction selectivity versus different molecules: 100 µM ABA-HP was incubated with 100 µM (1 eq) of different molecules in 50% HEPES/DMSO (pH 7.4) at 37° C. for 4 hours and detected by HPLC. $H_2S$ was generated by 100 µM $Na_2S$ solution in HEPES buffer, which can slowly release $H_2S$. .OH and .OtBu were generated by reaction of $Fe^{2+}$ with $H_2O_2$ or tert-butyl hydroperoxide (TBHP), respectively. HPLC condition was the same as the stability and reactivity test of ABA-HP.

Chemical stability and reactivity of GA-HP towards $H_2O_2$: GA-HP chemical stability: 5 mM GA-HP (in DMSO) was incubated in 50% HEPES/DMSO (10 mM HEPES, pH 7.4) for 24 hours at 37° C. and detected by HPLC. GA-HP reactivity towards $H_2O_2$: 5 mM GA-HP was incubated with 50 mM (10 eq) $H_2O_2$ in 50% HEPES/DMSO (10 mM HEPES, pH 7.4) at 37° C. HPLC results were detected at 5 minutes, 30 minutes, 60 minutes, 90 minutes, and 120 minutes. HPLC chromatograms were acquired using an ULTIMATE 3000 LC System (Thermo Fisher Scientific, Waltham, Mass.) with ACCLAIM 120 Å, C18, 3 µm analytical (4.6×100 mm) column (Thermo Fisher Scientific, Waltham, Mass.). Chromatographic conditions: eluent A: 0.1% v/v TFA in water; eluent B: 0.1% v/v TFA in acetonitrile. Solutions in DMSO were eluted at a flow rate of 1.000 ml/min monitored at a wavelength of 206 nm. 0-12 min (linear): 95% A, 5% B to 5% A, 95% B; 12-16 min: 5% A, 95% B; 16-18 min (linear): 5% A, 95% B to 95% A, 5% B.

Cloning and Plasmid Construction.

All DNA fragments were amplified by PCR (Polymerase chain reaction) from other intermediate constructs with the enzyme of Phusion DNA Polymerase (New England Biolabs, Ipswich, Mass.), or PfuUltra II Fusion HotStart DNA Polymerase (Agilent Technologies, Santa Clara, Calif.) under S1000 thermal cycler with Dual 48/48 Fast Reaction Module (Bio-Rad Laboratories, Inc., Hercules, Calif.). DNA fragments were inserted into the vector using T4 DNA Ligase (New England Biolabs, Ipswich, Mass.) or In-Fusion HD Enzyme Premix (Clontech Laboratories, Inc., Mountain View, Calif.). All the restriction enzymes used below are purchased from New England Biolabs.

PYL-eGFP-Tiam1 construct: Derived from pSV40-VP16-PYL-IRES-Gal4DBD-ABI (Liang et al., 2011, Sic. Signal. 4, rs2) by inserting a PYL fragment using EcoRI and AscI sites, a Tiam1-SG linker fragment using AscI and NotI sites, and an eGFP-SG-linker fragment using AscI site.

```
PYL Fragment: PCR amplified by primers
                                  (SEQ ID NO: 1)
CCGACAGAATTCGCCACCATGACCCAGGACGAGTTTACCCAG
and
                                  (SEQ ID NO: 2)
CCGACAGGCGCGCCGCTGCCGCCGTTCATAGCCTCAGTAATGCT Tiam1-SG linker fragment: PCR amplified by primers
                                  (SEQ ID NO: 3)
GCTATGAACGGCGCGCCAAGTGCTGGTGGTAGTGCTGGT
and
                                  (SEQ ID NO: 4)
CTAGAGTCGCGGCCGCTCAGATCTCAGTGTTCAGTTTC eGFP-SG-linker fragment: PCR amplified by primers
                                  (SEQ ID NO: 5)
CCGACAGGCGCGCCAGGTGGATCTGGAGGTTCAGGTGGATCTGGAGGTGT
GAGCAAGGGCGAGGAGCTG
and
                                  (SEQ ID NO: 6)
CCGACAGGCGCGCCCTTGTACAGCTCGTCCATGCC
```

NES-GID1 construct: generated from NES-ABI (Liang et al., 2011, Sic. Signal. 4, rs2) by inserting GID1 fragment using MluI and NotI sites.

```
GID1 fragment: PCR amplified by primers
                                  (SEQ ID NO: 7)
CCGACAACGCGTGGATCTGGTGGAGCTGCGAGCGATGAAGTTAAT
and
                                  (SEQ ID NO: 8)
CCGACAGCGGCCGCTCAACATTCCGCGTTTACAAACGC
```

EGFP-GAI construct: generated from eGFP-PYL (Liang et al., 2011, Sic. Signal. 4, rs2). GAI fragment was inserted by AscI and blunt end ligation into AscI and blunted NotI site on the vector.

```
GAI fragment: PCR amplified by primers
                                  (SEQ ID NO: 9)
CCGACAGGCGCGCCAGGATCTGGTGGAAAGAGAGATCATCATCATCAT
and
                                  (SEQ ID NO: 10)
CCGACAGGATCCTCAAGGATTAAGGTCGGTGAGCAT
```

Mammalian Cell Culture and Transfection.

All cells were cultured in DMEM medium (GIBCO, Life Technologies, Carlsbad, Calif.) supplemented with 10% FBS, 2 mM GlutaMAX (Life Technologies, Carlsbad, Calif.), 100 U/ml penicillin (Life Technologies, Carlsbad, Calif.) and 100 µg/ml streptomycin (Life Technologies, Carlsbad, Calif.) at 37° C. in a humidified atmosphere containing 5% $CO_2$.

EGFP expression experiments: HEK 293T (GFP) cells were seeded 24 hours prior to treatment in 24-well plates at 100 K/well. 10 µM ABA-HP was added to the cells 10 minutes prior to the addition of 10 µM ABA and 10, 50, or 100 µM of $H_2O_2$. Images were taken for living cells at 5 hours, 7 hours, 10 hours and 24 hours.

NES localization experiments: CHO cells were seeded in 24-well plates at 50 K/well with coverslip for 24 hours. 0.4 µg NES-ABI and 0.2 µg eGFP-PYL (FIG. 2a, ii) of DNA plasmid were used for each well, with 30 µL of Opti-MEM (Life Technologies, Carlsbad, Calif.) and 1.8 µL of PEI. After incubation at room temperature for 15 min, the mixture was added to the cells and cultured for 24 hours. Then, 10 µM ABA-HP was added to the cells 10 minutes prior to the addition of 10 µM ABA and 100 µM of $H_2O_2$, or 10 µM GA-HP was added to the cells 10 minutes prior to the addition of 10 µM GA-AM and 100 µM of $H_2O_2$. Slides were made 30 minutes after addition of compounds and images were taken the next day.

Ruffle generation experiment: CHO were seeded in 24-well plates at 50 K/well with coverslip for 24 hours. 0.1 µg PYL-eGFP-Tiam1 and 0.1 µg myr-ABI (FIG. 2a, iii) of DNA plasmid were used for each well, with 30 µL of Opti-MEM (Life Technologies, Carlsbad, Calif.) and 1.8 µL PEI. After incubation at room temperature for 15 min, the mixture was added to the cells and cultured for 24 hours. Then, 10 µM ABA-HP was added to the cells 10 minutes prior to the addition of 10 µM ABA and 100 µM of $H_2O_2$. Slides were made 30 minutes after addition of compounds and images were taken the next day.

Fluorescence Microscopy.

An Axio Observer D1 fluorescent microscope (Carl Zeiss AG, Oberkochen, Germany) outfitted with HBO 100 microscopy illumination system (Carl Zeiss AG, Oberkochen, Germany; GFP: excitation 470/40 and emission 525/50) was used to analyze GFP expression and NES localization. A 20× objective was used to analyze GFP expression. A 63× objective was used for NES localization.

A LSM 510 META Confocal Microscope (Carl Zeiss AG, Oberkochen, Germany) with 40× and 63× oil-immersion objectives to analyze ruffle formation. Fluorophore channels in all experiments were adjusted to the same intensity ranges. Acquisition times ranged from 100 to 1000 ms.

Example 2

HPLC analysis: Reversed-phase HPLC was performed on an ACCLAIM 120 (4.6×100 mm) C18 column (Thermo Fisher Scientific, Waltham, Mass.) with an ULTIMATE 3000 pump system, including a Variable Wavelength Detector 3100, Degasser 1210, and Autosampler SPS 3000 (Thermo Fisher Scientific, Waltham, Mass.). A mixture of water and acetonitrile containing 0.1% TFA was used as the eluent. Absorbance at 250 nm was used to monitor the elution of the molecules. The method used an increase in acetonitrile from 5% to 95% over 15 minutes to elute the molecules at a flow rate of 0.7 mL/min. The peaks for the molecules were integrated by using Chromeleon software (Thermo Fisher Scientific, Waltham, Mass.). The molar absorptivity of both free and caged ABA at 250 nm were measured, which was used to calculate the concentration of each species from the intensity of absorbance at 250 nm. The relative concentration of each compound was used to calculate the percent concentration of free ABA relative to the concentration of total ABA species (both caged and uncaged).

Cell culture and transfection: CHO cells and HEK 293T EGFP reporter cells (provided by Dr. Gerald R. Crabtree) were cultured in Dulbecco's modified Eagle's medium (DMEM; GIBCO, Life Technologies, Carlsbad, Calif.) with 10% FBS (Atlanta Biologicals, Inc., Norcross, Ga.), 1×GlutaMAX (GIBCO, Life Technologies, Carlsbad, Calif.), and 1× penicillin/streptomycin (Pen/Strep; GIBCO, Life Technologies, Carlsbad, Calif.). 15,000-50,000 ells were plated in a 24-well or 8-well plate for 24 hours before transfection. DNA constructs (0.1 µg-0.5 µg) were added to 50× (v/w) Opti-MEM (GIBCO, Life Technologies, Carlsbad, Calif.), and then 3× (v/w) PEI (Polysciences, Inc., Warrington, Pa.) was mixed with the DNA. The mixture was incubated for 20 minutes at room temperature before adding it to cell cultures. The cells were grown for one day after transfection before experiments were performed.

DNA plasmid construction: Construction of the 5FL, 5IG, SV-VPiGA, NES-ABI, GFP-PYL, and myr-ABI plasmids has been described previously. (Liang et al., 2011, *Sic. Signal.* 4, rs2) The PYL-eGFP-Tiam1 construct was constructed as described in Example 1.

Photo-irradiation: Irradiation at 365 nm was performed with an Axio Observer (Carl Zeiss AG, Oberkochen, Germany) microscope with an HBO103 W/2 mercury arc lamp (Carl Zeiss AG, Oberkochen, Germany). Irradiation was performed by using a DAPI filter (Carl Zeiss AG, Oberkochen, Germany), set with peak excitation at 365 nm (power density: 23 mW $cm^2$) and a spectral width of 50 nm. No objective lens was used for whole-well irradiation, which created an area of illumination that nearly completely covered one well of a 24-well plate. Light was transmitted through the bottom of the well of polystyrene plate. Irradiation at 405 nm was performed by using an adjustable focus violet purple laser pointer (LazerPoint SKU 0733579), with an excitation wavelength of 405 nm and 1000 mW intensity positioned 8 cm above the bottom of either a 96-well or 24-well plate and irradiated through the polystyrene lid. All samples for HPLC analysis were irradiated in DMSO to prevent evaporation of solvent and changes in sample concentration. Irradiation of cell cultures was performed in 24-well plates containing culture medium (500 µL).

Luciferase assay: Cells from 24-well plates were washed with PBS and lysed with Reporter lysis buffer (100 µL; Promega Corp., Madison, Wis.) by incubation and gentle shaking at room temperature for 10 minutes after a freeze/thaw cycle. Cell lysates were centrifuged at 15,000 rpm in an Eppendorf 5424 Centrifuge with lysate used for the luciferase assay (25 µL). Luciferase assay reagent (100 µL, 5 mg luciferin (Gold Biotechnology, Inc., St. Louis, Mo.) and coenzyme A (7 mg; Sigma-Aldrich, St. Louis, Mo.) in Luciferase Assay Buffer (33 mL, 20 mM tricine, 1.07 mM $(MgCO_3)_4Mg(OH)_2.5\ H_2O$, 2.67 mM $MgSO_4$, 0.1 mM EDTA, 33.3 mM dithiothreitol, and 0.53 mM ATP in water) was added to lysates. Luciferase assay reagent was added through the auto-injector of a GLOMAX-Multi Detection System (Promega Corp., Madison, Wis.), and the signal was detected by the instrument with a 1.5 s delay and 0.5 s integration time. All experiments were conducted in triplicate.

Slide preparation: Cells were grown on glass coverslips in 24-well plates. The coverslips were washed with phosphate-buffered saline (PBS) and fixed with 4% paraformaldehyde (PFA, 300 µL, prepared in PBS) at room temperature for 20 min. The cells were then washed twice with PBS and incubated with 1×DAPI in the dark at the room temperature for 5 min. After a final wash with PBS, the coverslips were mounted on a glass slide with VECTASHIELD (Vector Laboratories, Inc., Burlingame, Calif.) mounting media and allowed to stand for two hours in the dark before imaging.

Fluorescence microscopy imaging: Slides were imaged with an Axio Observer (Carl Zeiss AG, Oberkochen, Germany) microscope or with am LSM 510 Meta confocal microscope (Carl Zeiss AG, Oberkochen, Germany) mounted on an AxioObserver inverted microscope with a 63× oil objective. Images were taken with DAPI and GFP channels.

Live cell confocal microscopy irradiation and imaging: EGFP fluorescence of CHO cells was detected with an LSM 510 Meta confocal mounted on an AxioObserver inverted microscope (Carl Zeiss AG, Oberkochen, Germany). ABA-DEACM was uncaged by using a 405 nm UV laser (25 mW) set to 25% power for approximately three seconds. To image, fluorescence was excited with the 488 nm line of an argon laser (30 mW) with laser power attenuated to 50%. EGFP emission was collected with a FITC filter. Live cells were plated in 8-well coverslip-bottom culture chambers in medium (200 μL) and maintained at 37° C. with an objective lens heater (Bioptechs Inc., Butler, Pa.). Culture medium was exchanged with OptiMEM (GIBCO, Life Technologies, Carlsbad, Calif.) with caged ABA or no drug prior to imaging. Images were acquired every 10 to 20 seconds in different experiments with a 63×5/1.2 NA water objective.

Statistical analysis of cell population: Cell were categorized as displaying nuclear export of EGFP when the fluorescent intensity of the nucleus was less than 60% of the intensity of the cytoplasm. Cells were categorized as ruffled when they displayed broad extensions identifiable as lamellipodia or filopodia from the GFP fluorescence from membrane-localized EGFP-PYL-Tiam1. Cells were counted from three separate experiments, with N>50 for each experiment.

Image analysis of fluorescence intensity in nuclear export experiments: Generated images were analyzed for fluorescence intensity by using Slide Book v.6 software (Intelligent Imaging Innovations, Inc., Denver, Colo.). Equal sized regions of interest were analyzed from the cytoplasm and the nucleus to compare fluorescent intensity of EGFP in three cells for each condition from images taken every 20 seconds for a duration of 20 minutes.

Example 3

Mammalian Cell Culture: HEK 293 EGFP reporter cells were cultured in Dulbecco's modified Eagle's medium (DMEM, GIBCO, Life Technologies, Carlsbad, Calif.) with 10% Fetal Bovine Serum (FBS, GIBCO, Life Technologies, Carlsbad, Calif.), 1× Glutamate (100× from GIBCO, Life Technologies, Carlsbad, Calif.), and 1× Penicillin/Streptomycin (Pen/Strep, 100× from GIBCO, Life Technologies, Carlsbad, Calif.). Cells were plated with the starting concentration of 200,000 cells per well in a 24-well plate (Greiner Bio-One GmbH; Frickenhausen, Germany) for a day, and then were treated with either 10 μM of ABA-Fe and 20 μM of DFO, 10 μM of ABA-Fe only, or 10 μM of ABA-Fe and 100 μM of $Fe^{2+}$ aqueous solution.

Imagines for green fluorescence were taken for living cells every two hours after adding in those molecules by microscopy illumination system (Axio Observer; Carl Zeiss AG, Oberkochen, Germany). Each type of the experiment was carried out as duplex.

Reverse-Phase HPLC Analysis

Chemical stability of ABA-Fe molecules: 100 μM ABA-Fe (in 50% HEPES/DMSO buffer, pH=7.4) was incubated at 37° C. for one hour before HPLC detection. The percentages for molecule cleavage were quantified by the peak area of ABA out of the total peak area.

ABA-Fe reactivity and selectivity towards $Fe^{2+}$: 100 μM ABA-Fe with 1 mM $Fe^{2+}$ (in 50% HEPES/DMSO buffer, pH=7.4), and 100 μM ABA-Fe with 1 mM $Fe^{3+}$ (in 50% HEPES/DMSO buffer, pH=7.4) were incubated at 37° C. for one hour before HPLC detection. The percentages for molecule cleavage were quantified by the peak area of ABA out of the total peak area.

HPLC chromatograms were acquired using an ULTIMATE 3000 LC System (Thermo Fisher Scientific, Waltham, Mass.) with ACCLAIM 120 Å, C18, 3 μm analytical (4.6×100 mm) column (Thermo Fisher Scientific, Waltham, Mass.). Chromatographic conditions: eluent A: 0.1% v/v TFA in water; eluent B: 0.1% v/v TFA in acetonitrile. ABA in ethanol or ABA-HP in DMSO was eluted at a flow rate of 0.750 ml/min monitored at a wavelength of 260 nm. 0-12 min (linear): 95% A, 5% B to 5% A, 95% B; 12-15 min: 5% A, 95% B; 15-17 min (linear): 5% A, 95% B to 95% A, 5% B. Generation of ABA was quantified by the peak area of ABA out of the total peak area.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A chemical-induced proximity (CIP) composition comprising:
   a first modular component comprising a first target molecule coupled to a first dimerizing moiety;
   a second modular component comprising a second target molecule coupled to a second dimerizing moiety; and
   a caged CIP inducer comprising:
      a CIP inducer comprising abscisic acid (ABA) or gibberellic acid (GA); and
      a caging group covalently attached to the CIP inducer, but removable from the CIP inducer under the control of a signal comprising a signal molecule or light.

2. The composition of claim 1, wherein the signal comprises a signal molecule.

3. The composition of claim 2 wherein the signal molecule comprises $H_2O_2$ or $Fe^{2+}$.

4. An isolated cell comprising:
   a polynucleotide comprising a coding region of interest operationally linked to a regulatory region that controls expression of the coding region; and
   the chemical-induced proximity (CIP) composition of claim 1.

5. The cell of claim 4 wherein the polynucleotide comprises a polynucleotide endogenous to the cell.

6. The cell of claim 4 wherein the polynucleotide comprises a polynucleotide exogenous to the cell.

7. A method comprising:
   introducing the chemical-induced proximity (CIP) composition of claim 1 into a cell; and
   contacting the cell with the signal molecule.

8. The method of claim 7 wherein the cell further comprises a polynucleotide whose expression is modulated by a complex comprising the first modular component dimerized to the second modular component.

9. The method of claim 8 wherein the polynucleotide comprises a polynucleotide endogenous to the cell.

10. The method of claim 8 wherein the polynucleotide comprises a polynucleotide exogenous to the cell.

11. A method comprising:
    providing the cell of claim 4; and
    contacting the cell with the signal molecule.

12. The method of claim 11 wherein the cell further comprises a polynucleotide whose expression is modulated by a complex comprising the first modular component dimerized to the second modular component.

13. The method of claim 12 wherein the polynucleotide comprises a polynucleotide endogenous to the cell.

14. The method of claim 12 wherein the polynucleotide comprises a polynucleotide exogenous to the cell.

* * * * *

UNITED STATES PATENT AND TRADEMARK OFFICE
CERTIFICATE OF CORRECTION

| | | |
|---|---|---|
| PATENT NO. | : 10,907,219 B2 | Page 1 of 1 |
| APPLICATION NO. | : 15/119506 | |
| DATED | : February 2, 2021 | |
| INVENTOR(S) | : Liang et al. | |

It is certified that error appears in the above-identified patent and that said Letters Patent is hereby corrected as shown below:

On the Title Page

Item (71), Applicants, 'STC.UNM' should read -UNM Rainforest Innovations-

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 50

<210> SEQ ID NO 1
<211> LENGTH: 42
<212> TYPE: DNA
<213> ORGANISM: artificial
<220> FEATURE:
<223> OTHER INFORMATION: synthetic oligonucleotide primer

<400> SEQUENCE: 1
ccgacagaat tcgccaccat gacccaggac gagtttaccc ag                42

<210> SEQ ID NO 2
<211> LENGTH: 44
<212> TYPE: DNA
<213> ORGANISM: artificial
<220> FEATURE:
<223> OTHER INFORMATION: synthetic oligonucleotide primer

<400> SEQUENCE: 2
ccgacaggcg cgccgctgcc gccgttcata gcctcagtaa tgct              44

<210> SEQ ID NO 3
<211> LENGTH: 39
<212> TYPE: DNA
<213> ORGANISM: artificial
<220> FEATURE:
<223> OTHER INFORMATION: synthetic oligonucleotide primer

<400> SEQUENCE: 3
gctatgaacg gcgcgccaag tgctggtggt agtgctggt                   39

<210> SEQ ID NO 4
<211> LENGTH: 38
<212> TYPE: DNA
<213> ORGANISM: artificial
<220> FEATURE:
<223> OTHER INFORMATION: synthetic oligonucleotide primer

<400> SEQUENCE: 4
ctagagtcgc ggccgctcag atctcagtgt tcagtttc                    38

<210> SEQ ID NO 5
<211> LENGTH: 69
<212> TYPE: DNA
<213> ORGANISM: artificial
<220> FEATURE:
<223> OTHER INFORMATION: synthetic oligonucleotide primer

<400> SEQUENCE: 5
ccgacaggcg cgccaggtgg atctggaggt tcaggtggat ctggaggtgt gagcaagggc    60
gaggagctg                                                          69

<210> SEQ ID NO 6
<211> LENGTH: 35
<212> TYPE: DNA
<213> ORGANISM: artificial
<220> FEATURE:
<223> OTHER INFORMATION: synthetic oligonucleotide primer

<400> SEQUENCE: 6
ccgacaggcg cgcccttgta cagctcgtcc atgcc                       35

<210> SEQ ID NO 7
<211> LENGTH: 45

```
<212> TYPE: DNA
<213> ORGANISM: artificial
<220> FEATURE:
<223> OTHER INFORMATION: synthetic oligonucleotide primer

<400> SEQUENCE: 7
ccgacaacgc gtggatctgg tggagctgcg agcgatgaag ttaat          45

<210> SEQ ID NO 8
<211> LENGTH: 38
<212> TYPE: DNA
<213> ORGANISM: artificial
<220> FEATURE:
<223> OTHER INFORMATION: synthetic oligonucleotide primer

<400> SEQUENCE: 8
ccgacagcgg ccgctcaaca ttccgcgttt acaaacgc                  38

<210> SEQ ID NO 9
<211> LENGTH: 48
<212> TYPE: DNA
<213> ORGANISM: artificial
<220> FEATURE:
<223> OTHER INFORMATION: synthetic oligonucleotide primer

<400> SEQUENCE: 9
ccgacaggcg cgccaggatc tggtggaaag agagatcatc atcatcat       48

<210> SEQ ID NO 10
<211> LENGTH: 36
<212> TYPE: DNA
<213> ORGANISM: artificial
<220> FEATURE:
<223> OTHER INFORMATION: synthetic oligonucleotide primer

<400> SEQUENCE: 10
ccgacaggat cctcaaggat taaggtcggt gagcat                    36

<210> SEQ ID NO 11
<211> LENGTH: 5
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (5)..(5)
<223> OTHER INFORMATION: Pro at position 5 is conjugated to a PABC
      peptide

<400> SEQUENCE: 11

Asp Glu Val Asp Pro
1               5

<210> SEQ ID NO 12
<211> LENGTH: 8
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: CAR peptide is conjugated to Lys at position 1

<400> SEQUENCE: 12

Lys Gly Ser Gly Asp Val Glu Gly
1               5
```

```
<210> SEQ ID NO 13
<211> LENGTH: 1
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Leu at position 1 is N-L-Leu

<400> SEQUENCE: 13

Leu
1

<210> SEQ ID NO 14
<211> LENGTH: 1
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Xaa at position 1 may be Arg, Ala, or Asp

<400> SEQUENCE: 14

Xaa
1

<210> SEQ ID NO 15
<211> LENGTH: 9
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: BHQ3 fluorescent quencher is conjugated to Lys
      at position 1

<400> SEQUENCE: 15

Lys Gln Glu Gln Asn Pro Gly Ser Thr
1               5

<210> SEQ ID NO 16
<211> LENGTH: 6
<212> TYPE: PRT
<213> ORGANISM: artificial
<220> FEATURE:
<223> OTHER INFORMATION: synthetic sensing probe

<400> SEQUENCE: 16

Gly Lys Ala Phe Arg Arg
1               5

<210> SEQ ID NO 17
<211> LENGTH: 7
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (3)..(3)
<223> OTHER INFORMATION: Xaa at position 5 is citrulline (Cit)
<220> FEATURE:
<221> NAME/KEY: MISC_FEATURE
```

```
<222> LOCATION: (5)..(5)
<223> OTHER INFORMATION: Phe at position 5 is Homophenylalanine (Hof)

<400> SEQUENCE: 17

Glu Pro Xaa Gly Phe Tyr Leu
1               5

<210> SEQ ID NO 18
<211> LENGTH: 8
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: BHQ3 fluorescent quencher is conjugated to Lys
      at position 1

<400> SEQUENCE: 18

Lys Arg Ala Leu Gly Leu Pro Gly
1               5

<210> SEQ ID NO 19
<211> LENGTH: 25
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: BHQ3 fluorescent quencher is conjugated to Glu
      at position 1
<220> FEATURE:
<221> NAME/KEY: MISC_FEATURE
<222> LOCATION: (1)..(8)
<223> OTHER INFORMATION: Glu at each of positions 1-8 is D-Glu
<220> FEATURE:
<221> NAME/KEY: MISC_FEATURE
<222> LOCATION: (17)..(24)
<223> OTHER INFORMATION: Arg at each of positions 17-24 is D-Arg

<400> SEQUENCE: 19

Glu Glu Glu Glu Glu Glu Glu Glu Arg Pro Leu Ala Leu Trp Arg Ser
1               5                   10                  15
Arg Arg Arg Arg Arg Arg Arg Arg Lys
            20                  25

<210> SEQ ID NO 20
<211> LENGTH: 3
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Ala at position 1 is D-Ala

<400> SEQUENCE: 20

Ala Phe Lys
1

<210> SEQ ID NO 21
<211> LENGTH: 3
<212> TYPE: PRT
<213> ORGANISM: artificial
<220> FEATURE:
<223> OTHER INFORMATION: synthetic sensing probe
```

```
<220> FEATURE:
<221> NAME/KEY: MISC_FEATURE
<222> LOCATION: (1)..(1)
<223> OTHER INFORMATION: Val at position 1 is D-Val

<400> SEQUENCE: 21

Val Leu Lys
1

<210> SEQ ID NO 22
<211> LENGTH: 3
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Ala at position 1 is D-Ala
<220> FEATURE:
<221> NAME/KEY: MISC_FEATURE
<222> LOCATION: (3)..(3)
<223> OTHER INFORMATION: Lys at position 3 is conjugated to a PABC
      peptide

<400> SEQUENCE: 22

Ala Phe Lys
1

<210> SEQ ID NO 23
<211> LENGTH: 7
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Mu peptide is conjugated to His at position 1

<400> SEQUENCE: 23

His Ser Ser Lys Leu Gln Leu
1               5

<210> SEQ ID NO 24
<211> LENGTH: 6
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Mu peptide is conjugated to His at position 1
<220> FEATURE:
<221> NAME/KEY: MISC_FEATURE
<222> LOCATION: (6)..(6)
<223> OTHER INFORMATION: Gln at position 6 is conjugated to an EDA
      peptide

<400> SEQUENCE: 24

His Ser Ser Lys Leu Gln
1               5

<210> SEQ ID NO 25
<211> LENGTH: 8
<212> TYPE: PRT
<213> ORGANISM: artificial
<220> FEATURE:
<223> OTHER INFORMATION: synthetic sensing probe
<220> FEATURE:
```

```
<221> NAME/KEY: MOD_RES
<222> LOCATION: (1)..(1)
<223> OTHER INFORMATION: Pro at position 1 is hydroxyproline (Hyp)
<220> FEATURE:
<221> NAME/KEY: MISC_FEATURE
<222> LOCATION: (1)..(1)
<223> OTHER INFORMATION: 4-O is conjugated to Pro at position 1
<220> FEATURE:
<221> NAME/KEY: MISC_FEATURE
<222> LOCATION: (4)..(4)
<223> OTHER INFORMATION: Xaa at position 4 is 2-amino-2-cyclohexylacetic
      acid (Chg)

<400> SEQUENCE: 25

Pro Ser Ser Xaa Gln Ser Ser Pro
1               5

<210> SEQ ID NO 26
<211> LENGTH: 7
<212> TYPE: PRT
<213> ORGANISM: artificial
<220> FEATURE:
<223> OTHER INFORMATION: synthetic sensing probe
<220> FEATURE:
<221> NAME/KEY: MOD_RES
<222> LOCATION: (1)..(1)
<223> OTHER INFORMATION: Pro at position 1 is hydroxyproline (Hyp)
<220> FEATURE:
<221> NAME/KEY: MISC_FEATURE
<222> LOCATION: (1)..(1)
<223> OTHER INFORMATION: HO2C(CH2)3CO is conjugated to Pro at position 1
<220> FEATURE:
<221> NAME/KEY: MISC_FEATURE
<222> LOCATION: (4)..(4)

<400> SEQUENCE: 26

Pro Ala Ser Xaa Gln Ser Leu
1               5

<210> SEQ ID NO 27
<211> LENGTH: 6
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Ala at position 1 is conjugated to
      N-gluaryl-(4-hydroxyprolyl)
<220> FEATURE:
<221> NAME/KEY: MISC_FEATURE
<222> LOCATION: (3)..(3)
<223> OTHER INFORMATION: Gly at position 3 is cyclohexylglycine (chGly)

<400> SEQUENCE: 27

Ala Ser Gly Gln Ser Leu
1               5

<210> SEQ ID NO 28
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Ala at position 1 is beta (B)-Ala

<400> SEQUENCE: 28

Ala Leu Ala Leu
```

```
<210> SEQ ID NO 29
<211> LENGTH: 3
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Ala at position 1 is D-Ala
<220> FEATURE:
<221> NAME/KEY: MISC_FEATURE
<222> LOCATION: (3)..(3)
<223> OTHER INFORMATION: Lys at position 3 is conjugated to a PABC
      peptide

<400> SEQUENCE: 29

Ala Phe Lys
1

<210> SEQ ID NO 30
<211> LENGTH: 1
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Poly(ethylene glycol) (PEG) is conjugated to
      Lys at position 1

<400> SEQUENCE: 30

Lys
1

<210> SEQ ID NO 31
<211> LENGTH: 1
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Glu at position 1 is polyglutamic acid

<400> SEQUENCE: 31

Glu
1

<210> SEQ ID NO 32
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: N-(2-hydroxypropyl)methacrylamide copolymer is
      conjugated to Gly at position 1

<400> SEQUENCE: 32

Gly Phe Leu Gly
1

<210> SEQ ID NO 33
```

```
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: ALB peptide is conjugated to Lys at position 1
<220> FEATURE:
<221> NAME/KEY: MISC_FEATURE
<222> LOCATION: (4)..(4)
<223> OTHER INFORMATION: Ala at position 4 is D-Ala
<220> FEATURE:
<221> NAME/KEY: MISC_FEATURE
<222> LOCATION: (4)..(4)
<223> OTHER INFORMATION: Ala at position 4 is conjugated to an EMC
      peptide

<400> SEQUENCE: 33

Lys Lys Phe Ala
1

<210> SEQ ID NO 34
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: ALB peptide is conjugated to Ala at position 1
<220> FEATURE:
<221> NAME/KEY: MISC_FEATURE
<222> LOCATION: (1)..(1)
<223> OTHER INFORMATION: EMC peptide is conjugated to Ala at position 1
<220> FEATURE:
<221> NAME/KEY: MISC_FEATURE
<222> LOCATION: (1)..(1)
<223> OTHER INFORMATION: Ala at position 1 is D-Ala

<400> SEQUENCE: 34

Ala Phe Lys Lys
1

<210> SEQ ID NO 35
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: N-(2-hydroxypropyl)methacrylamide copolymer is
      conjugated to Gly at position 1
<220> FEATURE:
<221> NAME/KEY: MOD_RES
<222> LOCATION: (4)..(4)
<223> OTHER INFORMATION: Leu at position 4 is norleucine (Nle)
<220> FEATURE:
<221> NAME/KEY: MISC_FEATURE
<222> LOCATION: (4)..(4)
<223> OTHER INFORMATION: Leu at position 4 is conjugated to 4-AB

<400> SEQUENCE: 35

Gly Gly Pro Leu
1

<210> SEQ ID NO 36
<211> LENGTH: 6
<212> TYPE: PRT
```

```
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Dexamethasone is cnojugated to Gly at position
      1

<400> SEQUENCE: 36

Gly Ile Leu Gly Val Pro
1               5

<210> SEQ ID NO 37
<211> LENGTH: 8
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: ALB peptide is conjugated to Gly at position 1

<400> SEQUENCE: 37

Gly Pro Leu Gly Ile Ala Gly Gln
1               5

<210> SEQ ID NO 38
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: ALB peptide is conjugated to Ala at position 1
<220> FEATURE:
<221> NAME/KEY: MISC_FEATURE
<222> LOCATION: (1)..(1)
<223> OTHER INFORMATION: EMC peptide is conjugated to Ala at position 1
<220> FEATURE:
<221> NAME/KEY: MISC_FEATURE
<222> LOCATION: (1)..(1)
<223> OTHER INFORMATION: Ala at position 1 is D-Ala

<400> SEQUENCE: 38

Ala Phe Lys Lys
1

<210> SEQ ID NO 39
<211> LENGTH: 8
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: ALB peptide is conjugated to Arg at position 1
<220> FEATURE:
<221> NAME/KEY: MISC_FEATURE
<222> LOCATION: (1)..(1)
<223> OTHER INFORMATION: EMC peptide is conjugated to Arg at position 1

<400> SEQUENCE: 39

Arg Arg Ser Ser Tyr Tyr Ser Gly
1               5

<210> SEQ ID NO 40
```

```
<211> LENGTH: 6
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: N-(2-hydroxypropyl)methacrylamide copolymer is
      conjugated to Ser at position 1
<220> FEATURE:
<221> NAME/KEY: MISC_FEATURE
<222> LOCATION: (1)..(1)
<223> OTHER INFORMATION: morpholinocarbonyl is conjugated to Ser at
      position 1

<400> SEQUENCE: 40

Ser Ser Lys Tyr Gln Leu
1               5

<210> SEQ ID NO 41
<211> LENGTH: 1
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Poly(ethylene glycol) (PEG) is conjugated to
      Lys at position 1
<220> FEATURE:
<221> NAME/KEY: MISC_FEATURE
<222> LOCATION: (1)..(1)
<223> OTHER INFORMATION: Lys at position 1 is polylysine

<400> SEQUENCE: 41

Lys
1

<210> SEQ ID NO 42
<211> LENGTH: 11
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Lys at position 1 is polylysine
<220> FEATURE:
<221> NAME/KEY: MISC_FEATURE
<222> LOCATION: (3)..(3)
<223> OTHER INFORMATION: Phe at position 3 is D-Phe
<220> FEATURE:
<221> NAME/KEY: MISC_FEATURE
<222> LOCATION: (4)..(4)
<223> OTHER INFORMATION: Xaa at position 4 is piperidine

<400> SEQUENCE: 42

Lys Gly Phe Xaa Arg Ser Gly Gly Gly Gly
1               5                   10

<210> SEQ ID NO 43
<211> LENGTH: 1
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Lys at position 1 is polylysine
```

```
<400> SEQUENCE: 43

Lys
1

<210> SEQ ID NO 44
<211> LENGTH: 8
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Lys at position 1 is polylysine
<220> FEATURE:
<221> NAME/KEY: MISC_FEATURE
<222> LOCATION: (5)..(5)
<223> OTHER INFORMATION: Arg at position 5 is D-Arg

<400> SEQUENCE: 44

Lys Gly Ala Ser Arg Phe Thr Gly
1               5

<210> SEQ ID NO 45
<211> LENGTH: 5
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: ALB peptide is conjugated to Gly at position 1
<220> FEATURE:
<221> NAME/KEY: MISC_FEATURE
<222> LOCATION: (1)..(1)
<223> OTHER INFORMATION: EMC peptide is conjguated to Gly at position 1

<400> SEQUENCE: 45

Gly Gly Gly Arg Arg
1               5

<210> SEQ ID NO 46
<211> LENGTH: 2
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: c1F6 antibody is conjguated to Val at position
      1
<220> FEATURE:
<221> NAME/KEY: MISC_FEATURE
<222> LOCATION: (2)..(2)
<223> OTHER INFORMATION: Xaa at position 2 is citrulline (Cit)

<400> SEQUENCE: 46

Val Xaa
1

<210> SEQ ID NO 47
<211> LENGTH: 2
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
```

```
<222> LOCATION: (1)..(1)
<223> OTHER INFORMATION: cAC10 antibody is conjugated to Val at position
      1
<220> FEATURE:
<221> NAME/KEY: MISC_FEATURE
<222> LOCATION: (2)..(2)
<223> OTHER INFORMATION: Xaa at position 2 is citrulline (Cit)

<400> SEQUENCE: 47

Val Xaa
1

<210> SEQ ID NO 48
<211> LENGTH: 2
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: Pep42 peptide is conjugated to Val at position
      1
<220> FEATURE:
<221> NAME/KEY: MISC_FEATURE
<222> LOCATION: (2)..(2)
<223> OTHER INFORMATION: Xaa at position 2 is citrulline (Cit)

<400> SEQUENCE: 48

Val Xaa
1

<210> SEQ ID NO 49
<211> LENGTH: 4
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: GAL peptide is conjugated to Gly at position 1
<220> FEATURE:
<221> NAME/KEY: MISC_FEATURE
<222> LOCATION: (1)..(1)
<223> OTHER INFORMATION: N-(2-hydroxylpropyl)methacrylamide copolymer is
      conjugated to Gly at position 1

<400> SEQUENCE: 49

Gly Phe Leu Gly
1

<210> SEQ ID NO 50
<211> LENGTH: 3
<212> TYPE: PRT
<213> ORGANISM: artificial
<220> FEATURE:
<223> OTHER INFORMATION: synthetic sensing probe
<220> FEATURE:
<221> NAME/KEY: MISC_FEATURE
<222> LOCATION: (1)..(1)
<223> OTHER INFORMATION: RGD peptide is conjugated to Ala at position 1
<220> FEATURE:
<221> NAME/KEY: MISC_FEATURE
<222> LOCATION: (1)..(1)
<223> OTHER INFORMATION: Ala at position 1 is D-Ala
```

```
<220> FEATURE:
<221> NAME/KEY: MISC_FEATURE
<222> LOCATION: (3)..(3)
<223> OTHER INFORMATION: Lys at position 3 is conjugated to a PABC
      peptide

<400> SEQUENCE: 50

Ala Phe Lys
1
```